(12) United States Patent
Pfister et al.

(10) Patent No.: US 10,374,168 B2
(45) Date of Patent: Aug. 6, 2019

(54) MATERIALS FOR ELECTRONIC DEVICES

(71) Applicant: Merck Patent GmbH, Darmstadt (DE)

(72) Inventors: Jochen Pfister, Alsbach-Haehnlein (DE); Frank Voges, Bad Duerkheim (DE); Elvira Montenegro, Weinheim (DE); Teresa Mujica-Fernaud, Darmstadt (DE)

(73) Assignee: Merck Patent GmbH (DE)

( * ) Notice: Subject to any disclaimer, the term of this patent is extended or adjusted under 35 U.S.C. 154(b) by 69 days.

(21) Appl. No.: 15/303,390

(22) PCT Filed: Mar. 19, 2015

(86) PCT No.: PCT/EP2015/000603
§ 371 (c)(1),
(2) Date: Oct. 11, 2016

(87) PCT Pub. No.: WO2015/158411
PCT Pub. Date: Oct. 22, 2015

(65) Prior Publication Data
US 2017/0125701 A1    May 4, 2017

(30) Foreign Application Priority Data

Apr. 14, 2014   (EP) .................................... 14001344

(51) Int. Cl.
| H01L 51/50 | (2006.01) |
| --- | --- |
| H01L 51/00 | (2006.01) |
| C07D 471/10 | (2006.01) |
| C09K 11/06 | (2006.01) |
| C09K 11/02 | (2006.01) |

(52) U.S. Cl.
CPC ........ *H01L 51/0072* (2013.01); *C07D 471/10* (2013.01); *C09K 11/025* (2013.01); *C09K 11/06* (2013.01); *H01L 51/006* (2013.01); *H01L 51/0052* (2013.01); *H01L 51/0073* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/185* (2013.01); *H01L 51/0056* (2013.01); *H01L 51/506* (2013.01); *H01L 51/5016* (2013.01); *H01L 51/5056* (2013.01); *H01L 51/5088* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| 2011/0240979 A1* | 10/2011 | Kim et al. ............. | H01L 51/54 257/40 |
| --- | --- | --- | --- |
| 2014/0061548 A1 | 3/2014 | Montenegro et al. | |
| 2014/0316134 A1 | 10/2014 | Stoessel et al. | |

FOREIGN PATENT DOCUMENTS

| JP | 2002-265938 | * | 9/2002 | ............. C09K 11/06 |
| --- | --- | --- | --- | --- |
| JP | 2002265938 A | | 9/2002 | |
| WO | WO-2012150001 A1 | | 11/2012 | |
| WO | WO-2013083216 A1 | | 6/2013 | |

OTHER PUBLICATIONS

Vaeth and Tang; Light emitting diodes based on phosphorescent guest/polymeric host systems; 2002; Journal of Applied Physics; vol. 92, No. 7; pp. 3447-3453.*

Gilman, H., et al "Synthesis of Some 5,10-Dihydrophenazasiline Derivatives", Journal of Organic Chemistry, vol. 26, No. 6, (1961), pp. 2013-2017.

International Search Report for PCT/EP2015/000603 dated May 28, 2015.

* cited by examiner

*Primary Examiner* — Gregory D Clark
(74) *Attorney, Agent, or Firm* — Drinker Biddle & Reath LLP

(57) ABSTRACT

The present application relates to heterospirobifluorene compounds, to a process for the preparation thereof, and to electronic devices, in particular organic electroluminescent devices, comprising the heterospirobifluorene derivatives.

23 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2015/000603, filed Mar. 19, 2015, which claims benefit of European Application No. 14001344.2, filed Apr. 14, 2014, both of which are incorporated herein by reference in their entirety.

The present application relates to a heterospirobifluorene compound of a formula (I) defined in greater detail below. The compound is preferably used in an electronic device, particularly preferably in an organic electroluminescent device (OLED).

Electronic devices in the sense of this application are taken to mean so-called organic electronic devices, which comprise organic semiconductor materials as functional materials. In particular, they are taken to mean OLEDs.

The structure of OLEDs in which organic compounds are employed as functional materials is described, for example, in U.S. Pat. Nos. 4,539,507, 5,151,629, EP 0676461 and WO 98/27136. In general, the term OLEDs is taken to mean electronic devices which comprise one or more layers comprising organic compounds and emit light on application of electrical voltage.

Layers having a hole-transporting function (hole-transporting layers), such as, for example, hole-injection layers, hole-transport layers, electron-blocking layers and emitting layers, have a great influence on the performance data of electronic devices.

It is known in the prior art to employ triarylamines as materials having hole-transporting properties in the above-mentioned layers. These may be monotriarylamines, as described, for example, in JP 1995/053955, WO 2006/123667 and JP 2010/222268, or bis- or other oligoamines, as described, for example, in U.S. Pat. No. 7,504,163 or US 2005/0184657. Known examples of triarylamine compounds as materials having hole-transporting properties for OLEDs are, inter alia, tris-p-biphenylamine, N,N'-di-1-naphthyl-N,N'-diphenyl-1,1'-biphenyl-4,4'-diamine (NPB) and 4,4',4"-tris-3-methylphenylphenylamino)triphenylamine (MTDATA).

It is known in the prior art, for example from WO 2012/150001, to use acridine derivatives in OLEDs. However, spirobisacridine derivatives are not proposed in this published specification.

Furthermore, the prior art, for example JP 2002-265938, discloses the use of spirobisacridine compounds in OLEDs. The compounds described in this published specification either contain no substituents on the benzene rings of the spirobisacridine skeleton or contain phenyl groups on the nitrogen atoms of the spirobisacridine skeleton.

A further published specification which describes the use of spirobisacridine compounds In OLEDs is KR 2011-0120075. The compounds described in this published specification contain no substituents on the benzene rings of the spirobisacridine skeleton.

Although the compounds disclosed in the above-mentioned documents are highly suitable for use in electronic devices, there continues to be a demand for novel compounds for this use. In particular, there is a demand for compounds which result in an improvement in the performance data of the electronic device, in particular in an improvement of lifetime, efficiency and operating voltage. In particular for use in hole-transporting layers of the electronic devices, novel materials having corresponding properties are continuously being sought.

In the course of investigations on novel materials for this use, it has now been found, surprisingly, that spirobisacridine compounds which conform to the formula (I) defined below and are characterised in that, in particular, they have an extended aromatic or heteroaromatic system on at least one of the nitrogen atoms and have an aromatic or heteroaromatic ring system on at least one of the benzene rings of the spirobisacrdine skeleton are highly suitable for use in OLEDs. They are suitable, in particular, for use in a hole-transporting layer.

The compounds found have one or more properties selected from very good hole-conducting properties, very good electron-blocking properties, high oxidation stability, good solubility, and high temperature stability. On use in OLEDs, they result in one or more advantageous properties of the OLEDs selected from long lifetime, high quantum efficiency and low operating voltage.

The present invention relates to a compound of the formula (I)

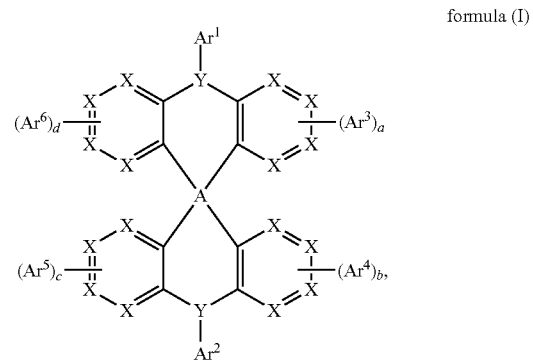

formula (I)

where the following applies to the symbols and indices occurring:

A is C or Si;
Y is on each occurrence, identically or differently, N or P;
X is on each occurrence, identically or differently, $CR^1$ or N;
$Ar^1$, $Ar^2$ are on each occurrence, identically or differently, an aromatic ring system having 6 to 40 aromatic ring atoms, which may be substituted by one or more radicals $R^2$, or a heteroaromatic ring system having 5 to 40 aromatic ring atoms, which may be substituted by one or more radicals $R^2$;
$Ar^3$, $Ar^4$, $Ar^5$, $Ar^6$ are on each occurrence, identically or differently, an aromatic ring system having 6 to 40 aromatic ring atoms, which may be substituted by one or more radicals $R^2$, or a heteroaromatic ring system having 5 to 40 aromatic ring atoms, which may be substituted by one or more radicals $R^2$;
$R^1$, $R^2$ are selected on each occurrence, identically or differently, from H, D, F, $C(=O)R^3$, $CF_3$, $OCF_3$, CN, $Si(R^3)_3$, $N(R^3)_2$, $P(=O)(R^3)_2$, $OR^3$, $S(=O)R^3$, $S(=O)_2R^3$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms and heteroaromatic ring systems having 5 to 40 aromatic ring atoms; where two or more radicals $R^1$ or $R^2$ may be linked to one another and may form a ring; where the said alkyl, alkoxy, alkenyl and alkynyl groups and the said aromatic ring systems and heteroaromatic ring systems may each be substituted by one or more radicals $R^3$; and where one or more $CH_2$ groups in the said alkyl, alkoxy, alkenyl and alkynyl groups may be replaced by —$R^3C$=$CR^3$—, —C≡C—, $Si(R^3)_2$, C=O, C=$NR^3$, —C(=O)O—, —C(=O)$NR^3$—, $NR^3$, P(=O)($R^3$), —O—, —S—, SO or $SO_2$;

$R^3$ is selected on each occurrence, identically or differently, from H, D, F, C(=O)$R^4$, $CF_3$, $OCF_3$, CN, $Si(R^4)_3$, $N(R^4)_2$, P(=O)($R^4$)$_2$, $OR^4$, S(=O)$R^4$, S(=O)$_2R^4$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms and heteroaromatic ring systems having 5 to 40 aromatic ring atoms; where two or more radicals $R^3$ may be linked to one another and may form a ring; where the said alkyl, alkoxy, alkenyl and alkynyl groups and the said aromatic ring systems and heteroaromatic ring systems may each be substituted by one or more radicals $R^4$; and where one or more $CH_2$ groups in the said alkyl, alkoxy, alkenyl and alkynyl groups may be replaced by —$R^4C$=$CR^4$—, —C≡C—, $Si(R^4)_2$, C=O, C=$NR^4$, —C(=O)O—, —C(=O)$NR^4$—, $NR^4$, P(=O)($R^4$), —O—, —S—, SO or $SO_2$;

$R^4$ is selected on each occurrence, identically or differently, from H, D, F, CN, alkyl groups having 1 to 20 C atoms, aromatic ring systems having 6 to 40 aromatic ring atoms and heteroaromatic ring systems having 5 to 40 aromatic ring atoms; where two or more radicals $R^4$ may be linked to one another and may form a ring; and where the said alkyl groups, aromatic ring systems and heteroaromatic ring systems may be substituted by F or CN;

a, b, c, d are on each occurrence, identically or differently, 0 or 1;

where at least one of the two groups $Ar^1$ and $Ar^2$ is an aromatic ring system having 12 to 40 aromatic ring atoms, which may be substituted by one or more radicals $R^2$, or a heteroaromatic ring system having 12 to 40 aromatic ring atoms, which may be substituted by one or more radicals $R^2$; and where at least one of the indices a, b, c and d is equal to 1.

If an index a, b, c or d is equal to 0, the corresponding group $Ar^2$, $Ar^4$, $Ar^5$ or $Ar^6$ is not present.

If an index a, b, c or d is equal to 1, the corresponding group $Ar^3$, $Ar^4$, $Ar^5$ or $Ar^6$ is bonded to one of the groups X of the ring. This group X is then equal to C, corresponding to the tetravalence of carbon.

An aryl group in the sense of this invention contains 6 to 60 aromatic ring atoms, none of which is a heteroatom. An aryl group in the sense of this Invention is taken to mean either a simple aromatic ring, i.e. benzene, or a condensed aromatic polycyclic ring system, for example naphthalene, phenanthrene or anthracene. A condensed aromatic polycyclic ring system in the sense of the present application consists of two or more simple aromatic rings condensed with one another. Condensation between rings here is taken to mean that the rings share at least one edge with one another.

A heteroaryl group in the sense of this invention contains 5 to 60 aromatic ring atoms, at least one of which is a heteroatom. The heteroatoms of the heteroaryl group are preferably selected from N, O and S. A heteroaryl group in the sense of this invention is taken to mean either a simple aromatic ring, i.e. benzene, or a simple heteroaromatic ring, for example pyridine, pyrimidine or thiophene, or a condensed heteroaromatic polycyclic ring system, for example quinoline or carbazole. A condensed heteroaromatic polycyclic ring system in the sense of the present application consists of two or more simple heteroaromatic rings condensed with one another. Condensation between rings here is taken to mean that the rings share at least one edge with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxallne, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system and includes no heteroatoms as aromatic ring atoms. An aromatic ring system in the sense of this invention therefore contains no heteroaryl groups. An aromatic ring system in the sense of this invention is intended to be taken to mean a system which does not necessarily contain only aryl groups, but instead in which, in addition, a plurality of aryl groups may be connected by a single bond or by a non-aromatic unit, such as, for example, one or more optionally substituted C, Si, N, O or S atoms. The non-aromatic unit here preferably contains less than 10% of the atoms other than H, based on the total number of atoms other than H in the system. Thus, for example, systems such as 9,9'-spirobifluorene, 9,9'-diarylfluorene, triarylamine, diaryl ether and stilbene are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl groups are linked to one another via single bonds are also taken to be aromatic ring systems in the sense of this invention, such as, for example, systems such as biphenyl and terphenyl.

A heteroaromatic ring system in the sense of this invention contains 5 to 60 aromatic ring atoms, at least one of which is a heteroatom. The heteroatoms of the heteroaromatic ring system are preferably selected from N, O and/or S. A heteroaromatic ring system corresponds to the above-mentioned definition of an aromatic ring system, but contains at least one heteroatom as one of the aromatic ring atoms. It consequently differs from an aromatic ring system in the sense of the definition of the present application, which, in accordance with this definition, cannot contain a heteroatom as aromatic ring atoms.

An aromatic ring system having 6 to 60 aromatic ring atoms or a heteroaromatic ring system having 5 to 60 aromatic ring atoms are taken to mean, in particular, groups derived from the groups mentioned above under aryl groups and heteroaryl groups and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cydopentyl, neopentyl, n-hexyl, cyclohexyl, neohexyl, n-heptyl, cydoheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cydoheptenyl, octenyl, cyclooctenyl, ethynyl, propynyl, butynyl, pentynyl, hexynyl or octynyl.

An alkoxy or thioalkyl group having 1 to 40 C atoms, in which, in addition, individual H atoms or $CH_2$ groups may be substituted by the groups mentioned above in the definition of the radicals, is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyl-oxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cydohexylthio, n-heptyl-thio, cycloheptylthio, n-octylthio, cyclooctytthio, 2-ethylhexylthio, trifluoro-methylthio, pentafluoroethylthio, 2,2,2-trifluoroethylthio, ethenylthio, propenylthio, butenylthio, pentenylthio, cydopentenylthio, hexenylthio, cydco-hexenylthio, heptenylthio, cydoheptenylthio, octenylthio, cydooctenylthio, ethynylthio, propynylthio, butynylthio, pentynylthio, hexynylthio, heptynyl-thio or octynylthio.

The formulation that two or more radicals may form a ring with one another is, for the purposes of the present application, intended to be taken to mean, inter alia, that the two radicals are linked to one another by a chemical bond. Furthermore, however, the above-mentioned formulation is also intended to be taken to mean that, in the case where one of the two radicals represents hydrogen, the second radical is bonded at the position to which the hydrogen atom was bonded, with formation of a ring.

According to a preferred embodiment, the compound of the formula (I) contains no arylamino group as substituent. An arylamino group in the sense of the present application is taken to mean a group in which one or more aryl or heteroaryl groups, preferably three aryl or heteroaryl groups, are bonded to a nitrogen atom.

According to a further preferred embodiment of the invention, the compound of the formula (I) contains no condensed aryl group having more than 10 aromatic ring atoms and no condensed heteroaryl group having more than 14 aromatic ring atoms.

Preferably, precisely 1, 2 or 3 indices selected from the indices a, b, c and d are equal to 1, particularly preferably precisely 1 or 2 indices selected from the indices a, b, c and d are equal to 1.

According to a preferred embodiment of the invention, the index a is equal to 1, and the indices b, c and d are equal to 0.

According to an alternative preferred embodiment, the indices a and b are equal to 1, and the indices c and d are equal to 0.

According to an alternative preferred embodiment, the indices a and c are equal to 1, and the indices b and d are equal to 0.

A is preferably a carbon atom.

Y is preferably a nitrogen atom.

Preferably at most three groups X, particularly preferably at most two groups X, and very particularly preferably at most one group X, per six-membered ring in the compound of the formula (I) are equal to N.

Preferably, not more than 2 directly adjacent groups X in a ring are equal to N.

X is preferably equal to $CR^1$.

$Ar^1$ and $Ar^2$ are preferably selected on each occurrence, identically or differently, from aromatic ring systems having 6 to 24 aromatic ring atoms, which may be substituted by one or more radicals $R^2$, or from heteroaromatic ring systems having 5 to 24 aromatic ring atoms, which may be substituted by one or more radicals $R^2$. It is thus preferred in combination that at least one of the two groups $Ar^1$ and $Ar^2$ is an aromatic ring system having 12 to 24 aromatic ring atoms, which may be substituted by one or more radicals $R^2$, or a heteroaromatic ring system having 12 to 24 aromatic ring atoms, which may be substituted by one or more radicals $R^2$. Particularly preferably, both of the groups $Ar^1$ and $Ar^2$ are selected on each occurrence, identically or differently, from aromatic ring systems having 12 to 24 aromatic ring atoms, which may be substituted by one or more radicals $R^2$, and heteroaromatic ring systems having 12 to 24 aromatic ring atoms, which may be substituted by one or more radicals $R^2$.

$Ar^1$, $Ar^2$, $Ar^3$, $Ar^4$, $Ar^5$ and $Ar^6$ preferably each contain at least one group selected from benzene, naphthalene, phenanthrene, fluoranthene, biphenyl, terphenyl, quaterphenyl, fluorene, indenofluorene, spirobifluorene, furan, benzofuran, isobenzofuran, dibenzofuran, thiophene, benzothiophene, isobenzothiophene, dibenzothiophene, indole, isoindole, carbazole, indolocarbazole, indenocarbazole, pyridine, quinoline, isoquinoline, acridine, phenanthridine, benzimidazole, pyrimidine, pyrazine and triazine, where the said groups may each be substituted by one or more radicals $R^2$.

$Ar^3$, $Ar^4$, $Ar^5$, $Ar^6$ are preferably selected on each occurrence, identically or differently, from aromatic ring systems having 6 to 24 aromatic ring atoms, which may be substituted by one or more radicals $R^2$, or from heteroaromatic ring systems having 5 to 24 aromatic ring atoms, which may be substituted by one or more radicals $R^2$.

The groups $Ar^3$, $Ar^4$, $Ar^5$, $Ar^6$ occurring in the compound of the formula (I) are preferably selected identically.

Preferred embodiments of the groups $Ar^1$, $Ar^2$, $Ar^3$, $Ar^4$, $Ar^5$ and $Ar^6$ are the groups indicated below:

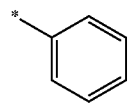

formula (Ar-1)

-continued
formula (Ar-2)
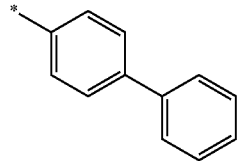
formula (Ar-3)
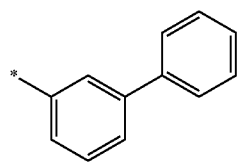
formula (Ar-4)
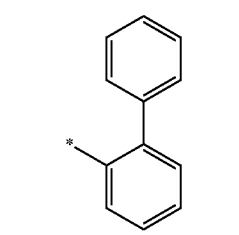
formula (Ar-5)
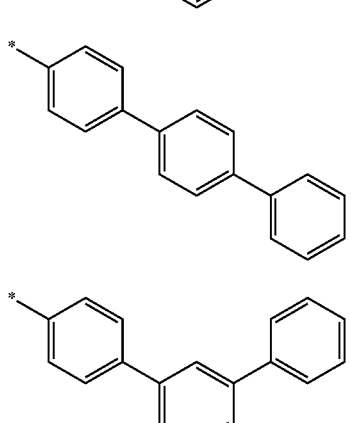
formula (Ar-6)
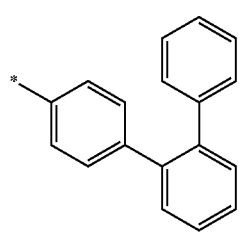
formula (Ar-7)
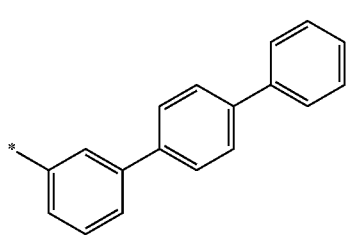
formula (Ar-8)
formula (Ar-9)
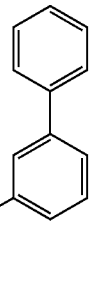
formula (Ar-10)
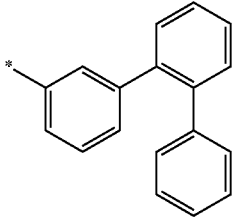
formula (Ar-11)
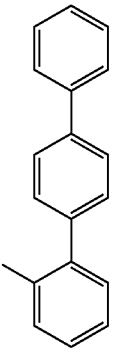
formula (Ar-12)
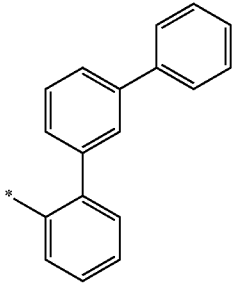
formula (Ar-13)
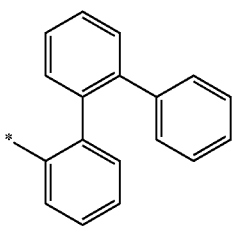

formula (Ar-14)
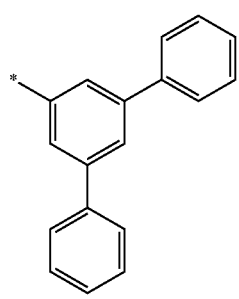
formula (Ar-15)
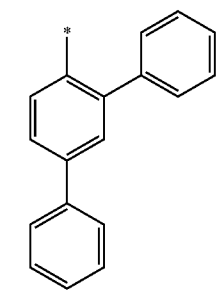
formula (Ar-16)
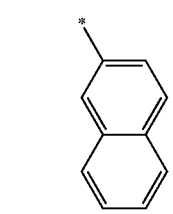
formula (Ar-17)
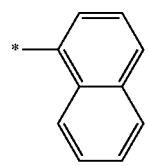
formula (Ar-18)
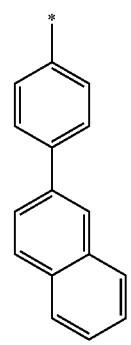
formula (Ar-19)
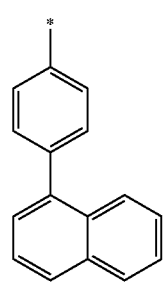
formula (Ar-20)
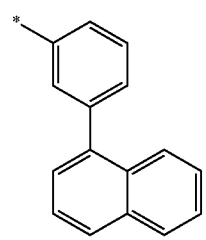
formula (Ar-21)
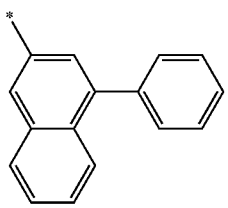
formula (Ar-22)
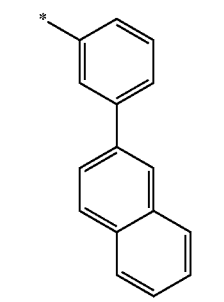
formula (Ar-23)
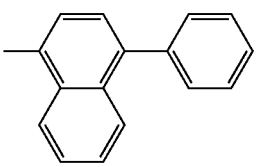
formula (Ar-24)
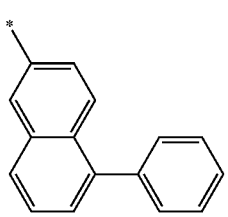
formula (Ar-25)
formula (Ar-26)
formula (Ar-27)
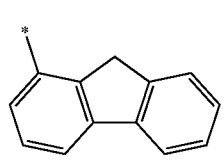

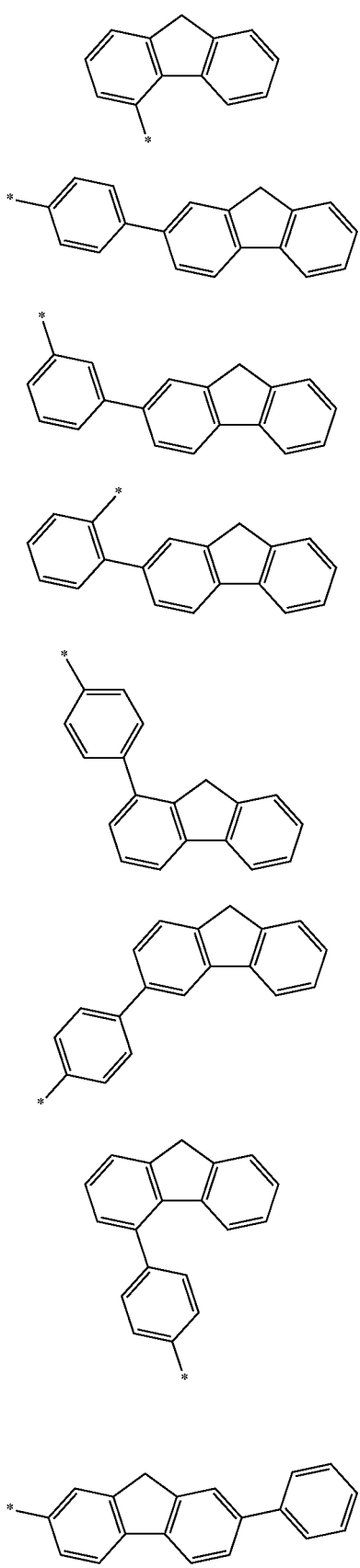
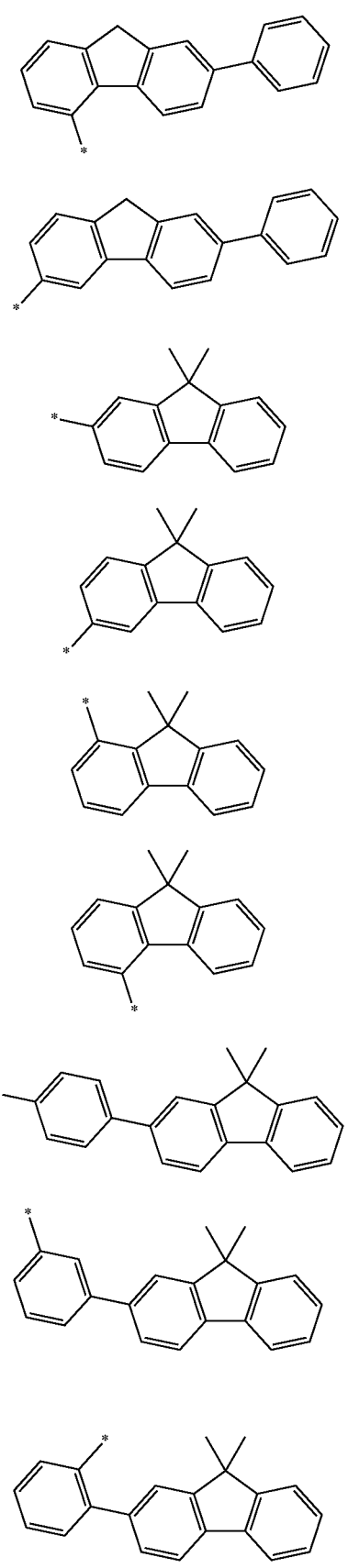

formula (Ar-32-1)
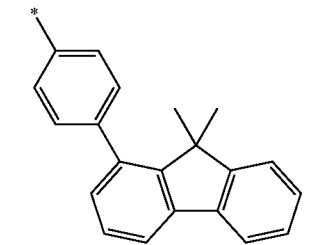
formula (Ar-33-1)
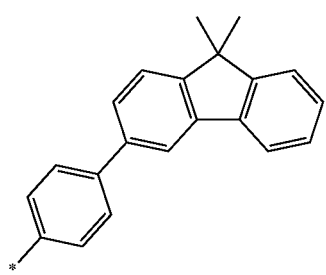
formula (Ar-34-1)
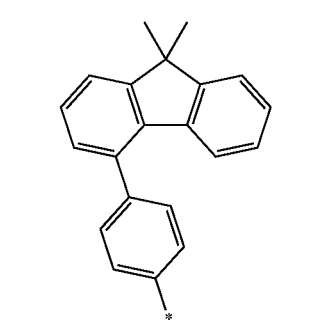
formula (Ar-35-1)
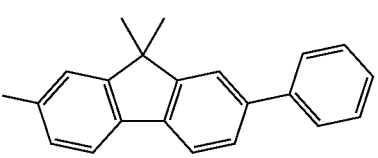
formula (Ar-36-1)
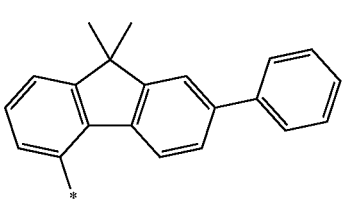
formula (Ar-37-1)
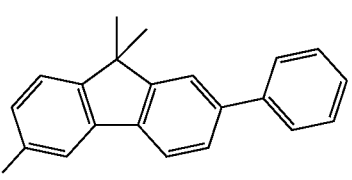
formula (Ar-25-2)
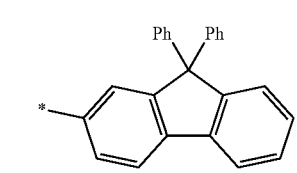
formula (Ar-26-2)
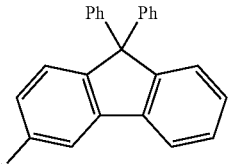
formula (Ar-27-2)
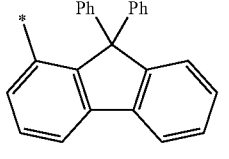
formula (Ar-28-2)
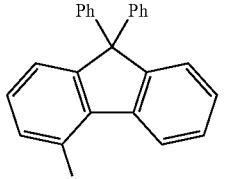
formula (Ar-29-2)
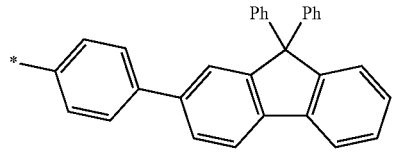
formula (Ar-30-2)
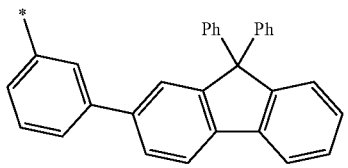
formula (Ar-31-2)
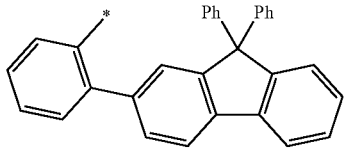
formula (Ar-32-2)
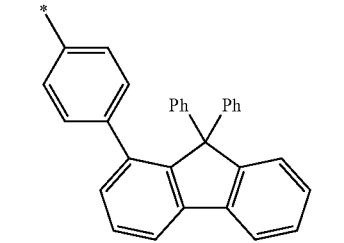
formula (Ar-33-2)
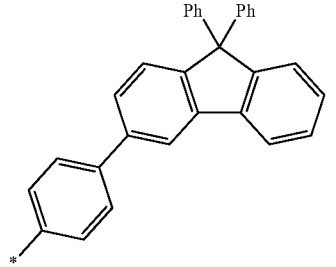

-continued
formula (Ar-34-2)
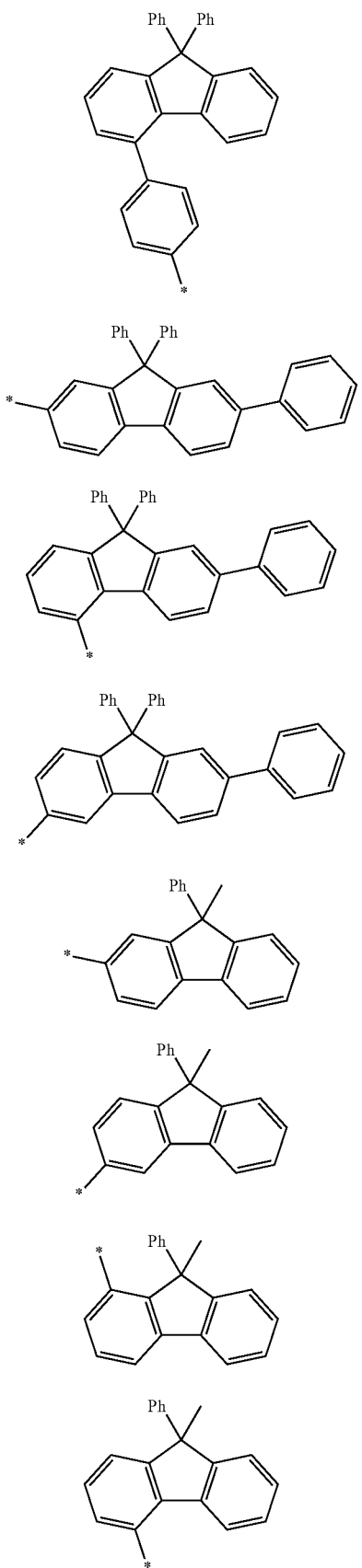
formula (Ar-35-2)
formula (Ar-36-2)
formula (Ar-37-2)
formula (Ar-25-3)
formula (Ar-26-3)
formula (Ar-27-3)
formula (Ar-28-3)
-continued
formula (Ar-29-3)
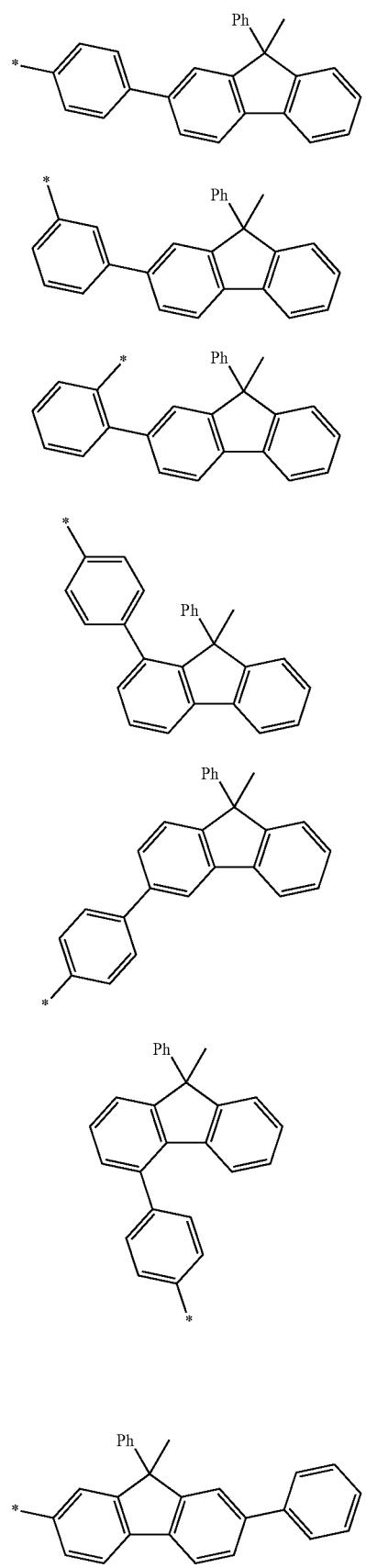
formula (Ar-30-3)
formula (Ar-31-3)
formula (Ar-32-3)
formula (Ar-33-3)
formula (Ar-34-3)
formula (Ar-35-3)

formula (Ar-36-3)
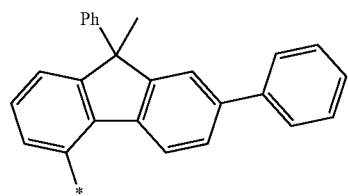
formula (Ar-37-3)
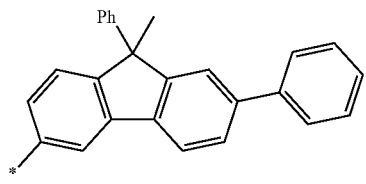
formula (Ar-25-4)
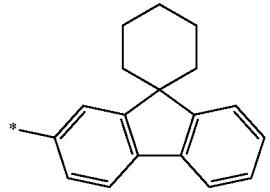
formula (Ar-26-4)
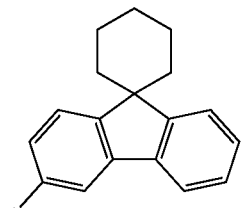
formula (Ar-27-4)
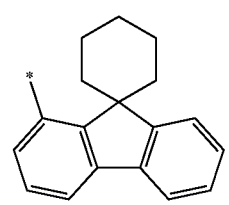
formula (Ar-28-4)
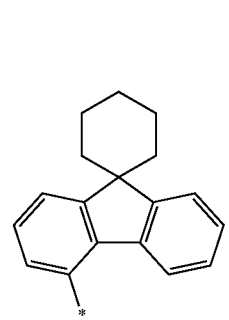
formula (Ar-29-4)
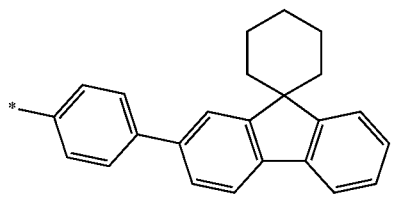
formula (Ar-30-4)
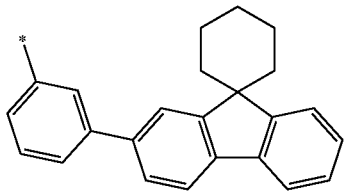
formula (Ar-31-4)
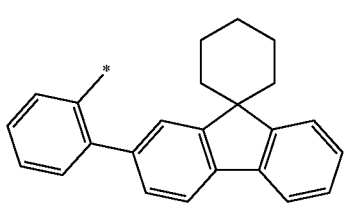
formula (Ar-32-4)
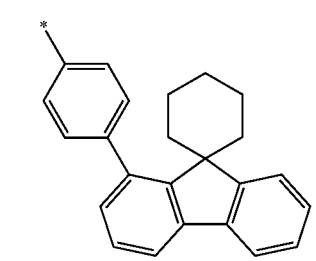
formula (Ar-33-4)
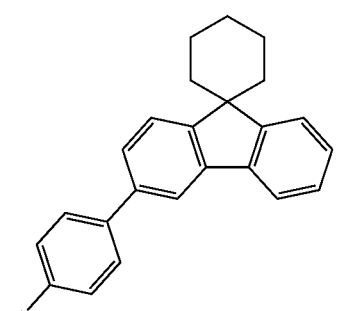
formula (Ar-34-4)
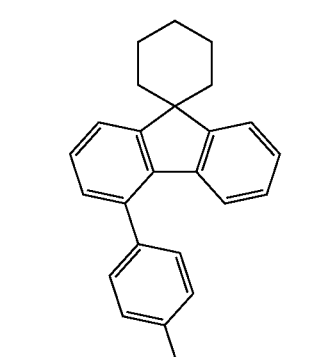
formula (Ar-35-4)
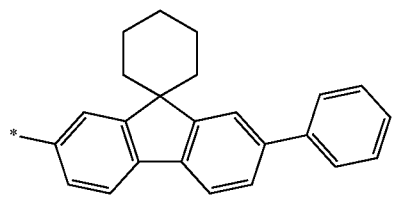

-continued
formula (Ar-36-4)
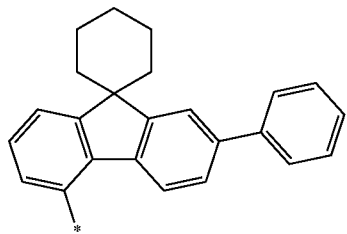
formula (Ar-37-4)
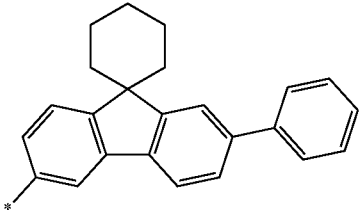
formula (Ar-25-5)
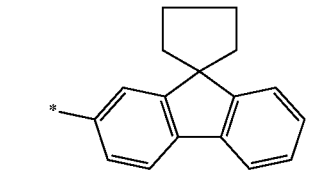
formula (Ar-26-5)
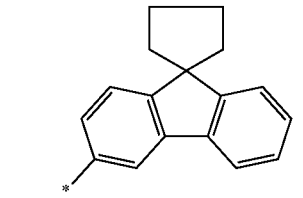
formula (Ar-27-5)
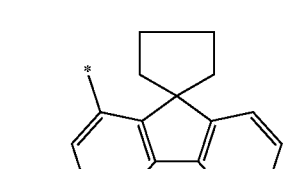
formula (Ar-28-5)
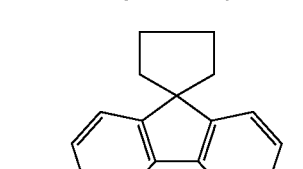
formula (Ar-29-5)
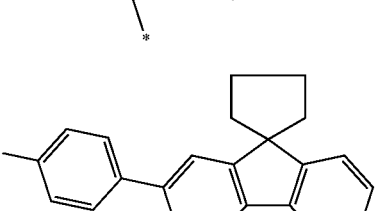
formula (Ar-30-5)
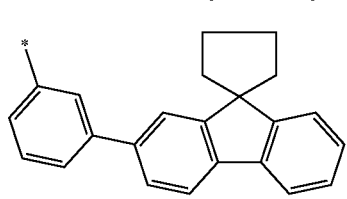
-continued
formula (Ar-31-5)
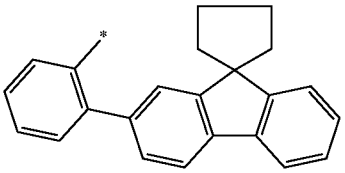
formula (Ar-32-5)
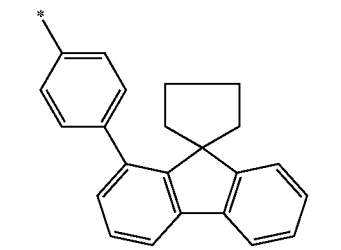
formula (Ar-33-5)
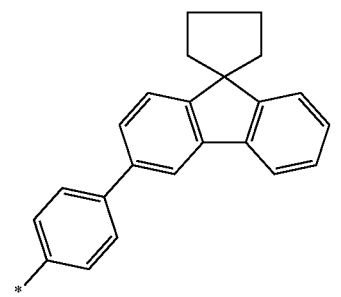
formula (Ar-34-5)
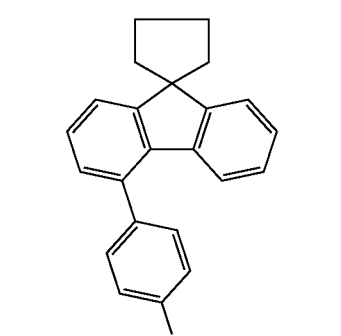
formula (Ar-35-5)
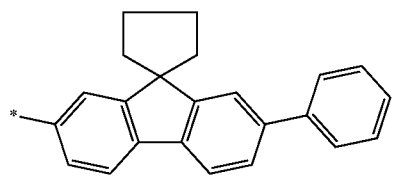
formula (Ar-36-5)
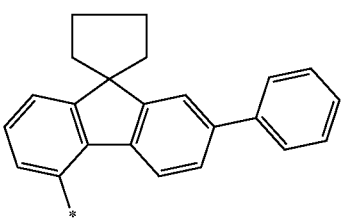

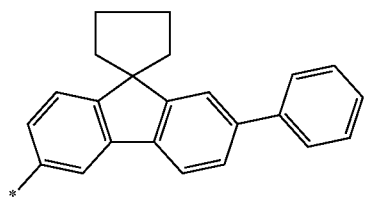
formula (Ar-37-5)
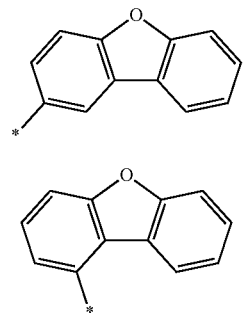
formula (Ar-38)
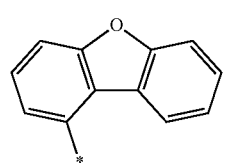
formula (Ar-39)
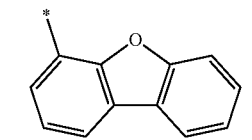
formula (Ar-40)
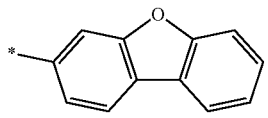
formula (Ar-41)
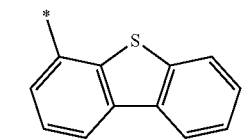
formula (Ar-42)
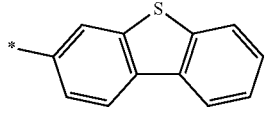
formula (Ar-43)
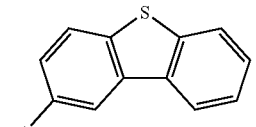
formula (Ar-44)
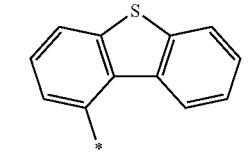
formula (Ar-45)
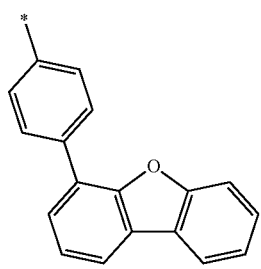
formula (Ar-46)
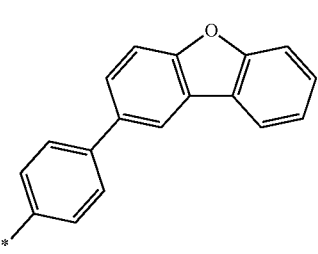
formula (Ar-47)
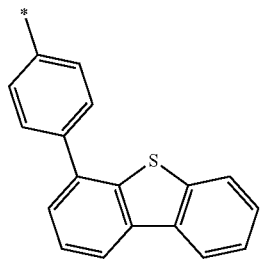
formula (Ar-48)
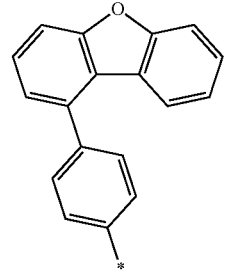
formula (Ar-49)
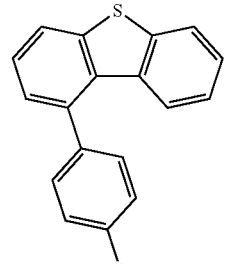
formula (Ar-50)
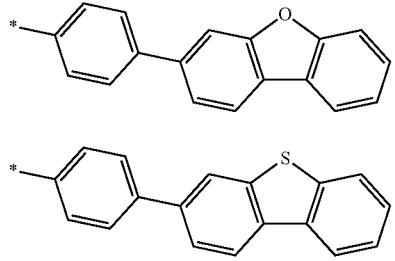
formula (Ar-51)
formula (Ar-52)

formula (Ar-53)
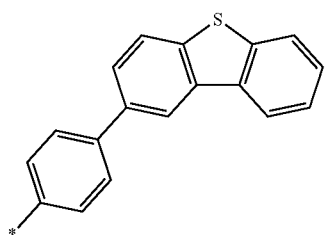
formula (Ar-54)
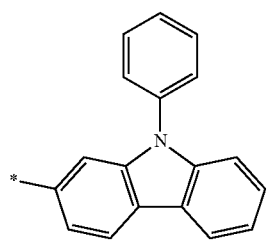
formula (Ar-55)
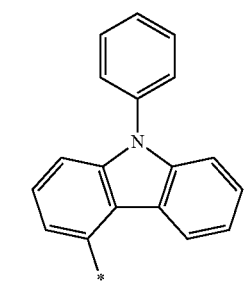
formula (Ar-56)
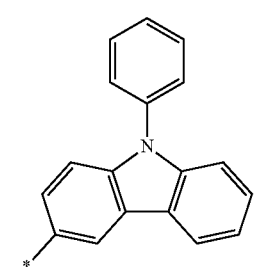
formula (Ar-57)
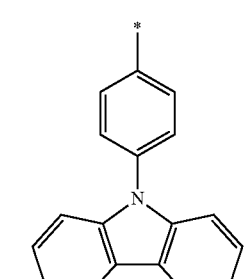
formula (Ar-58)
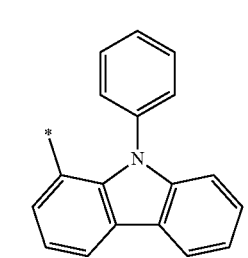
formula (Ar-59)
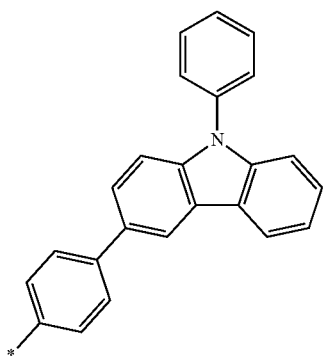
formula (Ar-60)
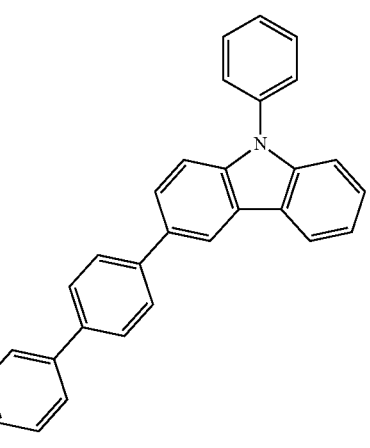
formula (Ar-61)
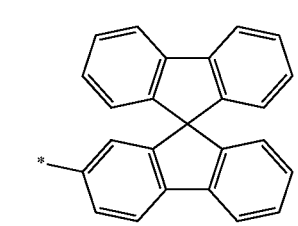
formula (Ar-62)
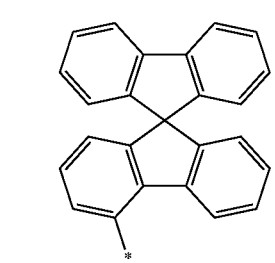
formula (Ar-63)
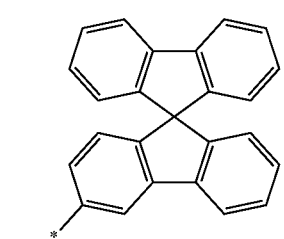

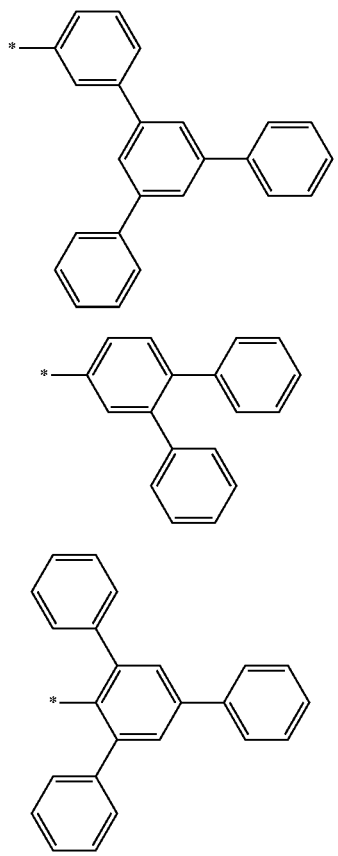

formula (Ar-64)

formula (Ar-65)

formula (Ar-66)

where the groups indicated may each be substituted by radicals R² at one or more of the free positions, and where the bond denoted by * represents the bonding position of the respective group.

Preferably, at least one of the groups Ar¹ and Ar² is selected from one of the above-mentioned groups of the formulae (Ar-2) to (Ar-15) and (Ar-18) to (Ar-66). Particularly preferably, both groups Ar¹ and Ar² are selected from one of the above-mentioned groups of the formulae (Ar-2) to (Ar-15) and (Ar-18) to (Ar-66).

Preferably, at least one of the groups $Ar^1$, $Ar^2$, $Ar^3$, $Ar^4$, $Ar^5$ and $Ar^6$ contains at least one heteroaryl group, as defined above. The at least one heteroaryl group preferably has 5 to 20 aromatic ring atoms, particularly preferably 6 to 14 aromatic ring atoms.

The radical $R^1$ is preferably selected on each occurrence, identically or differently, from H, D, F, CN, $Si(R^3)_3$, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^3$; and where one or more $CH_2$ groups in the said alkyl or alkoxy groups may be replaced by —C≡C—, $—R^3C=CR^3—$, $Si(R^3)_2$, C=O, $C=NR^3$, $—NR^3—$, —O—, —S—, —C(=O)O— or $—C(=O)NR^3—$. The radical $R^1$ is particularly preferably selected on each occurrence, identically or differently, from H, F, CN, $Si(R^3)_3$, aromatic ring systems having 6 to 24 aromatic ring atoms and heteroaromatic ring systems having 5 to 24 aromatic ring atoms; where the said aromatic ring systems and the said heteroaromatic ring systems may each be substituted by one or more radicals $R^3$. The radical $R^1$ is very particularly preferably equal to H.

The radical $R^2$ is preferably selected on each occurrence, identically or differently, from H, D, F, CN, $Si(R^3)_3$, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^3$; and where one or more $CH_2$ groups in the said alkyl or alkoxy groups may be replaced by —C≡C—, $—R^3C=CR^3—$, $Si(R^3)_2$, C=O, $C=NR^3$, $—NR^3—$, —O—, —S—, —C(=O)O— or $—C(=O)NR^3—$. The radical $R^2$ is particularly preferably selected on each occurrence, identically or differently, from H, F, CN, $Si(R^3)_3$, straight-chain alkyl groups having 1 to 10 C atoms, branched or cyclic alkyl groups having 3 to 10 C atoms, aromatic ring systems having 6 to 24 aromatic ring atoms and heteroaromatic ring systems having 5 to 24 aromatic ring atoms; where the said alkyl groups, the said aromatic ring systems and the said heteroaromatic ring systems may each be substituted by one or more radicals $R^3$.

The radical $R^3$ is preferably selected on each occurrence, identically or differently, from H, D, F, CN, $Si(R^4)_3$, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^4$; and where one or more $CH_2$ groups in the said alkyl or alkoxy groups may be replaced by —C≡C—, $—R^4C=CR^4—$, $Si(R^4)_2$, C=O, $C=NR^4$, $—NR^4—$, —O—, —S—, —C(=O)O— or $—C(=O)NR^4—$. The radical $R^3$ is particularly preferably selected on each occurrence, identically or differently, from H, F, CN, $Si(R^4)_3$, straight-chain alkyl groups having 1 to 10 C atoms, branched or cyclic alkyl groups having 3 to 10 C atoms, aromatic ring systems having 6 to 24 aromatic ring atoms and heteroaromatic ring systems having 5 to 24 aromatic ring atoms; where the said alkyl groups, the said aromatic ring systems and the said heteroaromatic ring systems may each be substituted by one or more radicals $R^4$.

The compound of the formula (I) preferably conforms to one of the formulae (I-1) to (I-3)

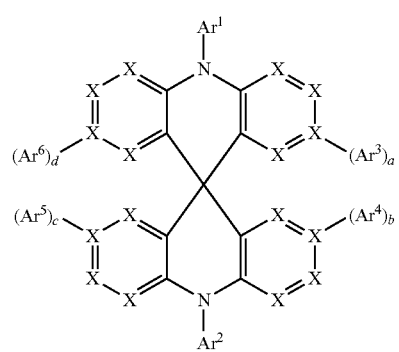

formula (I-1)

formula (I-2)

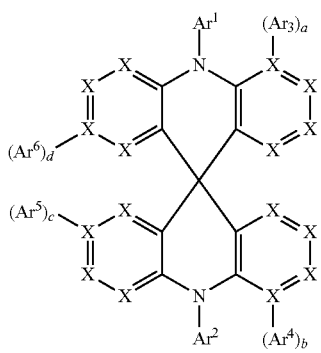

formula (I-1-2)

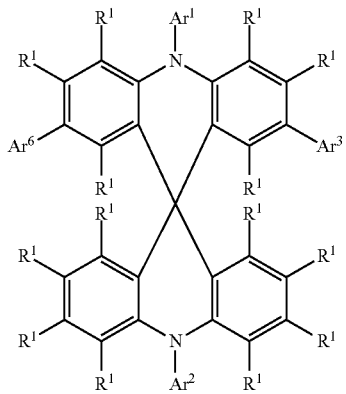

formula (I-3)

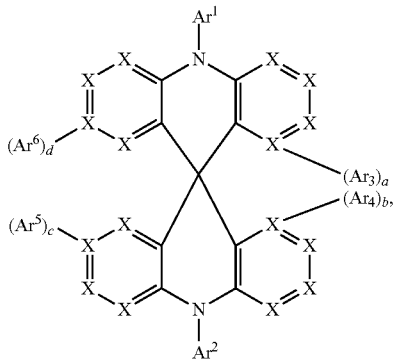

formula (I-1-3)

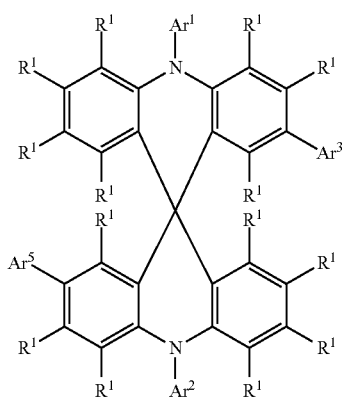

where the symbols and indices occurring are defined as above.

In particular, it is preferred for the compounds of the formulae (I-1) to (I-3) that X is equal to $CR^1$, and that precisely 1, precisely 2 or precisely 3 indices selected from the indices a, b, c and d are equal to 1.

Of the formulae (I-1) to (I-3), preference is given to formula (I-1).

The compound of the formula (I) particularly preferably conforms to one of the formulae (I-1-1) to (I-1-4)

formula (I-1-1)

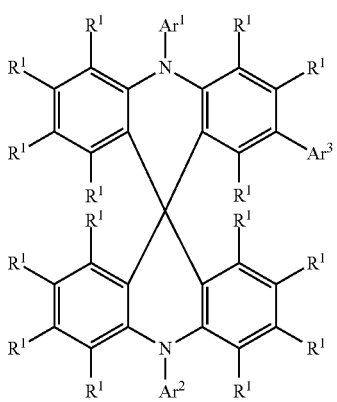

formula (I-1-4)

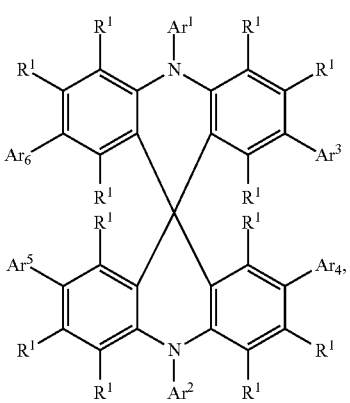

where the symbols occurring are defined as above.

Especial preference is given to the combination of the preferred embodiments of the formulae (I-1-1) to (I-1-4) with the above-mentioned preferred embodiments of the groups $R^1$, $Ar^1$, $Ar^2$, $Ar^3$, $Ar^4$, $Ar^5$ and AP.

Examples of compounds of the formula (I) are depicted in the following table:

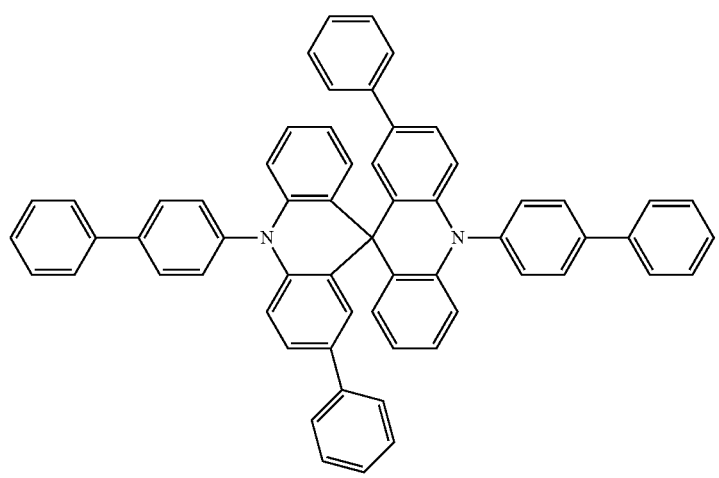 [SMILES: c1ccc(-c2ccc(N3c4ccccc4C4(c5ccccc5N(c5ccc(-c6ccccc6)cc5)c5ccc(-c6ccccc6)cc54)c4cc(-c5ccccc5)ccc43)cc2)cc1]
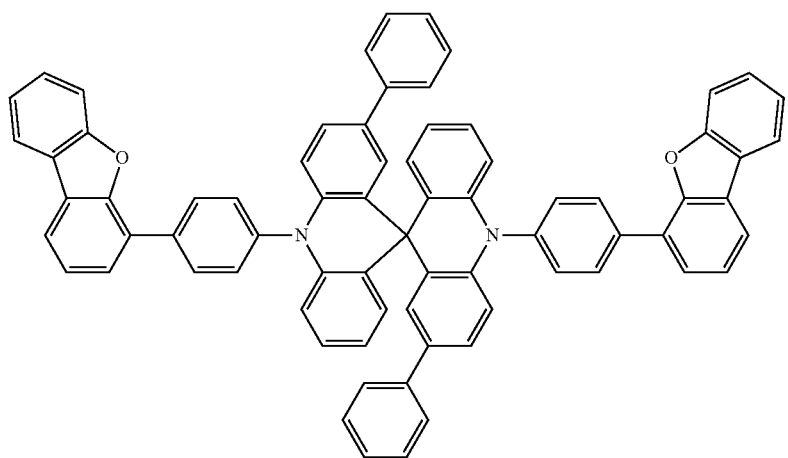
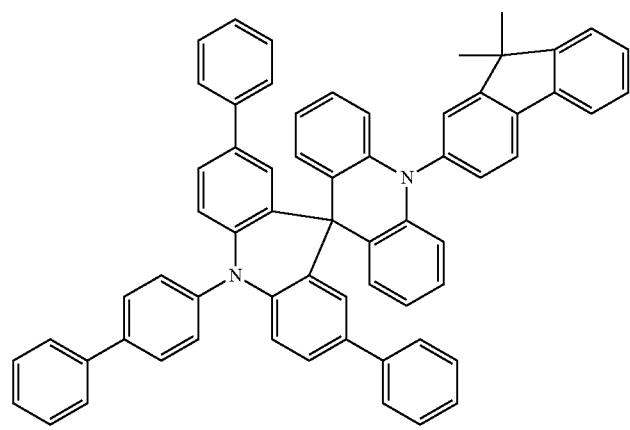 [SMILES: CC1(C)c2ccccc2-c2ccc(N3c4ccccc4C4(c5ccccc53)c3cc(-c5ccccc5)ccc3N(c3ccc(-c5ccccc5)cc3)c3ccc(-c5ccccc5)cc34)cc21]

-continued
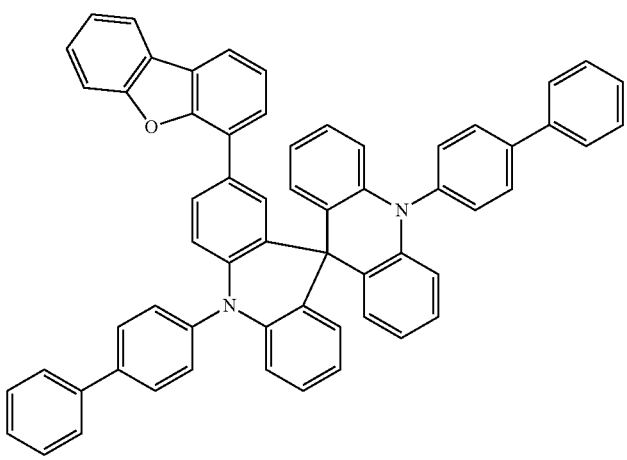 [SMILES: c1ccc(-c2ccc(N3c4ccccc4C4(c5ccccc53)c3ccccc3N(c3ccc(-c5ccccc5)cc3)c3ccc(-c5cccc6c5oc5ccccc56)cc34)cc2)cc1]
4
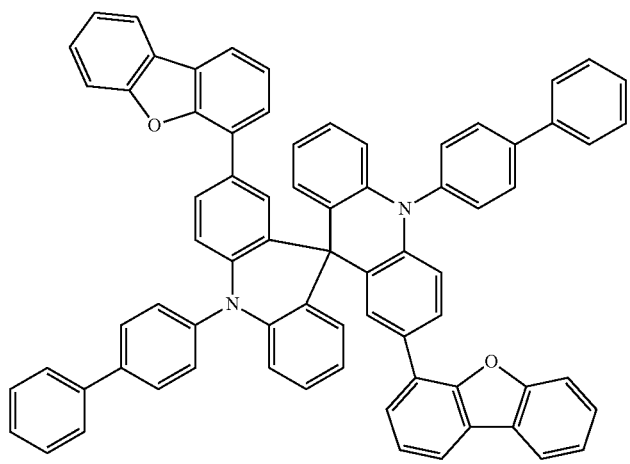 [SMILES: c1ccc(-c2ccc(N3c4ccccc4C4(c5ccccc5N(c5ccc(-c6ccccc6)cc5)c5ccc(-c6cccc7c6oc6ccccc67)cc54)c4cc(-c5cccc6c5oc5ccccc56)ccc43)cc2)cc1]
5
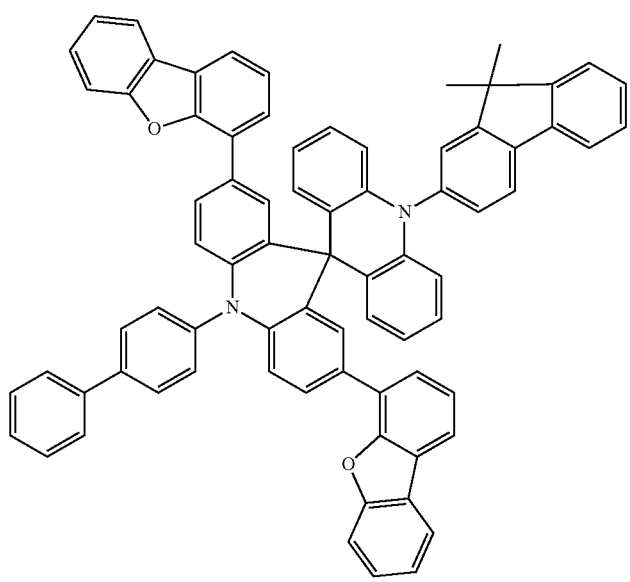 [SMILES: CC1(C)c2ccccc2-c2ccc(N3c4ccccc4C4(c5ccccc53)c3cc(-c5cccc6c5oc5ccccc56)ccc3N(c3ccc(-c5ccccc5)cc3)c3ccc(-c5cccc6c5oc5ccccc56)cc34)cc21]
6

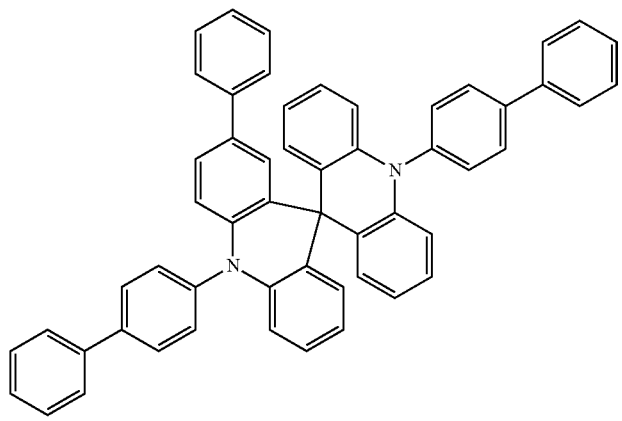 [SMILES: c1ccc(-c2ccc(N3c4ccccc4C4(c5ccccc53)c3ccccc3N(c3ccc(-c5ccccc5)cc3)c3ccc(-c5ccccc5)cc34)cc2)cc1]
7
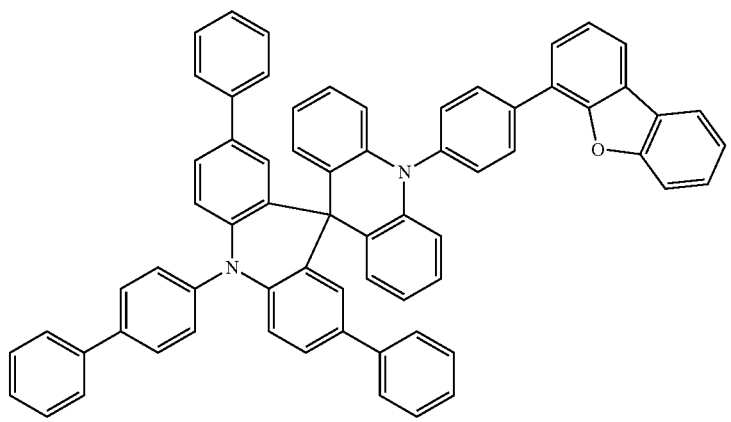 [SMILES: c1ccc(-c2ccc(N3c4ccc(-c5ccccc5)cc4C4(c5ccccc5N(c5ccc(-c6cccc7c6oc6ccccc67)cc5)c5ccccc54)c4cc(-c5ccccc5)ccc43)cc2)cc1]
8
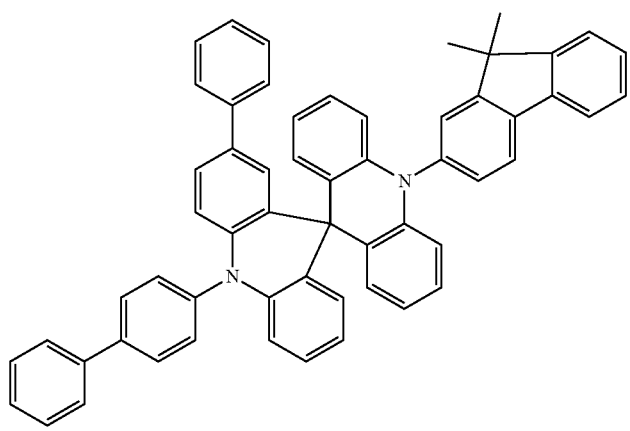 [SMILES: CC1(C)c2ccccc2-c2ccc(N3c4ccccc4C4(c5ccccc53)c3ccccc3N(c3ccc(-c5ccccc5)cc3)c3ccc(-c5ccccc5)cc34)cc21]
9

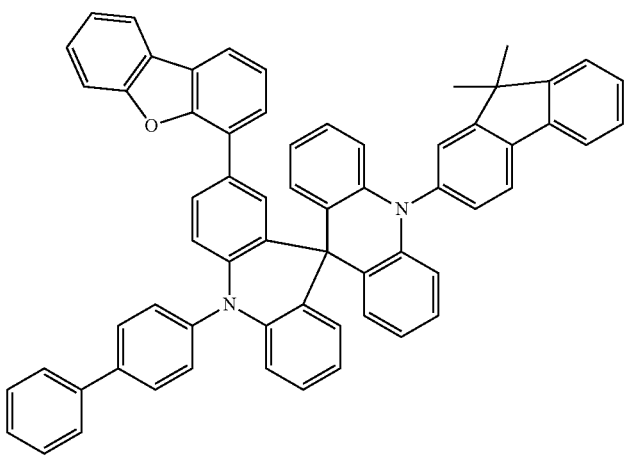 [SMILES: CC1(C)c2ccccc2-c2ccc(N3c4ccccc4C4(c5ccccc53)c3ccccc3N(c3ccc(-c5ccccc5)cc3)c3ccc(-c5cccc6c5oc5ccccc56)cc34)cc21]
10
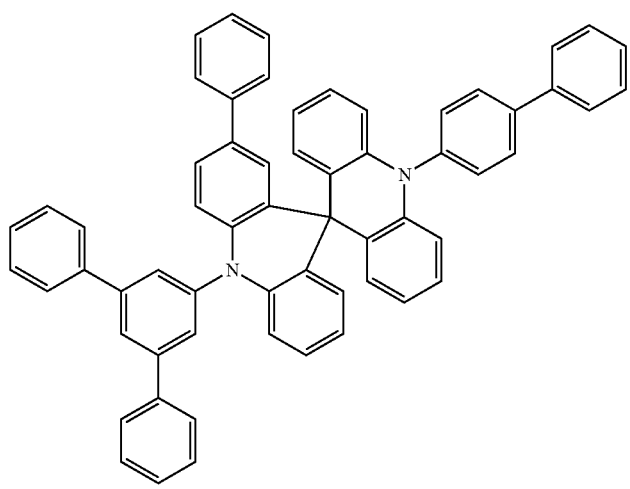 [SMILES: c1ccc(-c2ccc(N3c4ccccc4C4(c5ccccc53)c3ccccc3N(c3cc(-c5ccccc5)cc(-c5ccccc5)c3)c3ccc(-c5ccccc5)cc34)cc2)cc1]
11
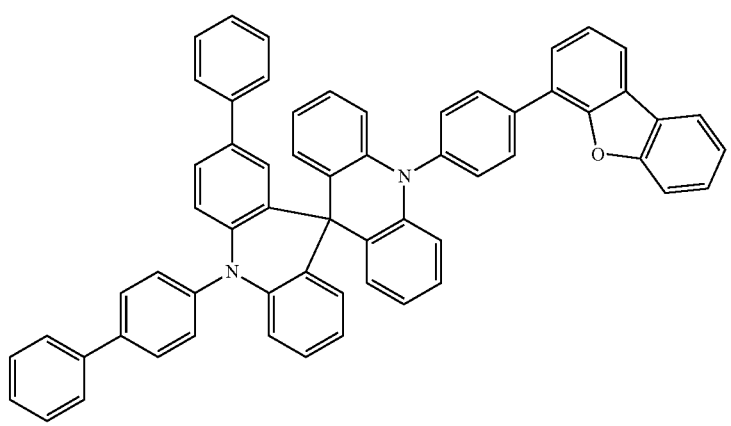 [SMILES: c1ccc(-c2ccc(N3c4ccccc4C4(c5ccccc5N(c5ccc(-c6cccc7c6oc6ccccc67)cc5)c5ccccc54)c4cc(-c5ccccc5)ccc43)cc2)cc1]
12

-continued
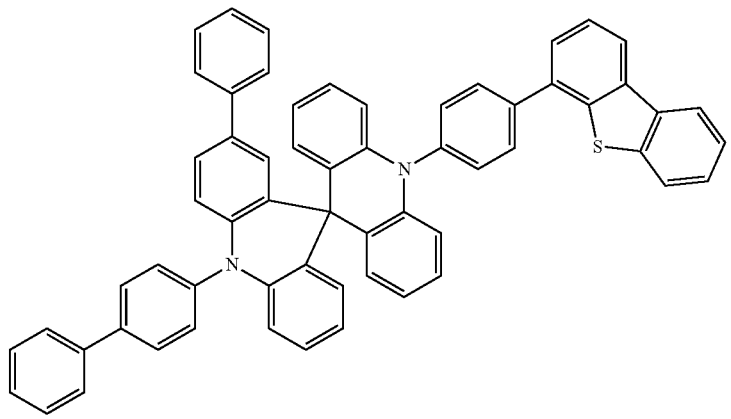
13
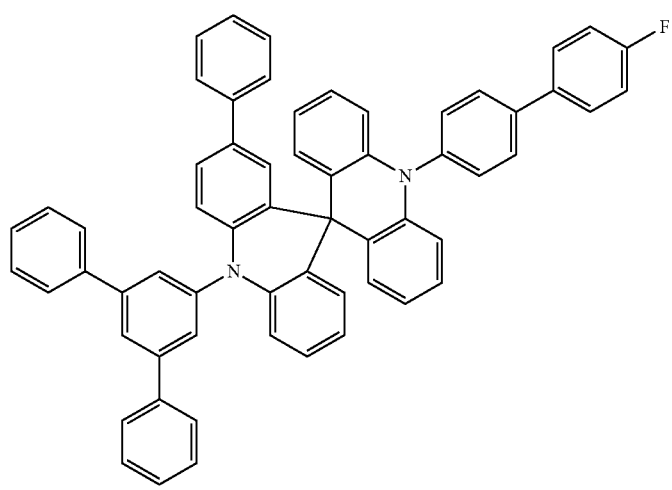 [SMILES: Fc1ccc(-c2ccc(N3c4ccccc4C4(c5ccccc53)c3ccccc3N(c3cc(-c5ccccc5)cc(-c5ccccc5)c3)c3ccc(-c5ccccc5)cc34)cc2)cc1]
14
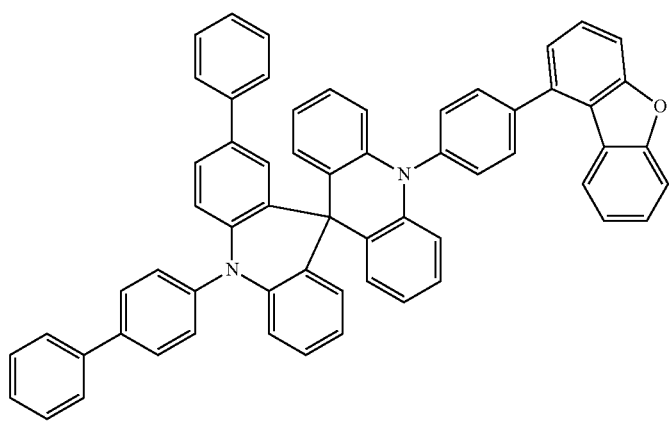 [SMILES: c1ccc(-c2ccc(N3c4ccccc4C4(c5ccccc5N(c5ccc(-c6cccc7sc8ccccc8c67)cc5)c5ccccc54)c4cc(-c5ccccc5)ccc43)cc2)cc1]
15

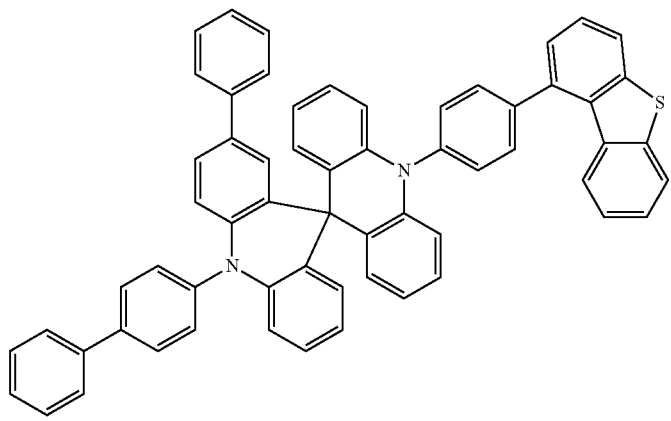
16
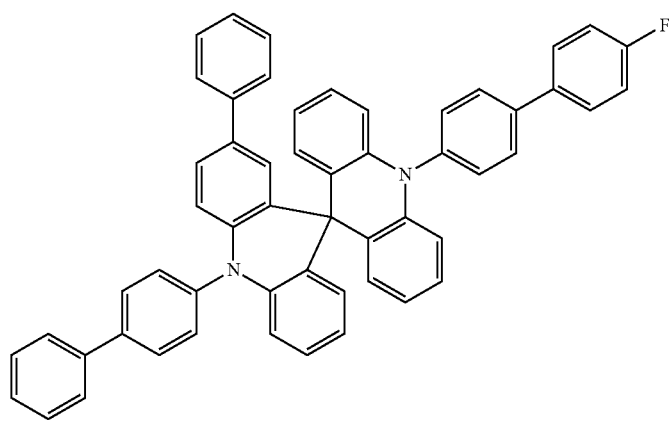 [SMILES: Fc1ccc(-c2ccc(N3c4ccccc4C4(c5ccccc53)c3ccccc3N(c3ccc(-c5ccccc5)cc3)c3ccc(-c5ccccc5)cc34)cc2)cc1]
17
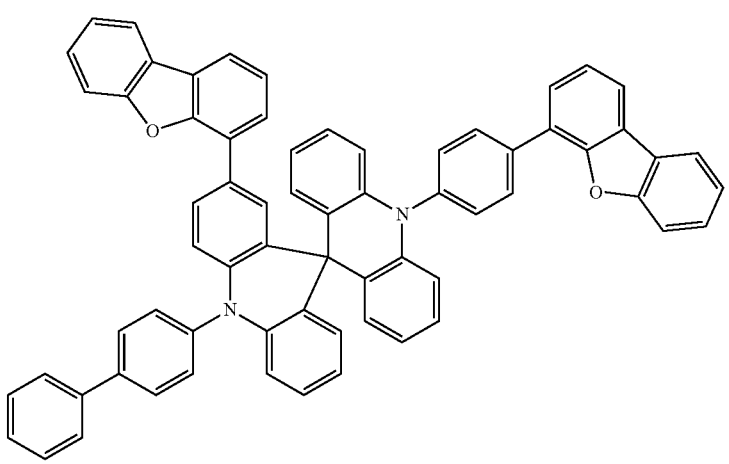 [SMILES: c1ccc(-c2ccc(N3c4ccccc4C4(c5ccccc5N(c5ccc(-c6cccc7c6oc6ccccc67)cc5)c5ccccc54)c4cc(-c5cccc6c5oc5ccccc56)ccc43)cc2)cc1]
18

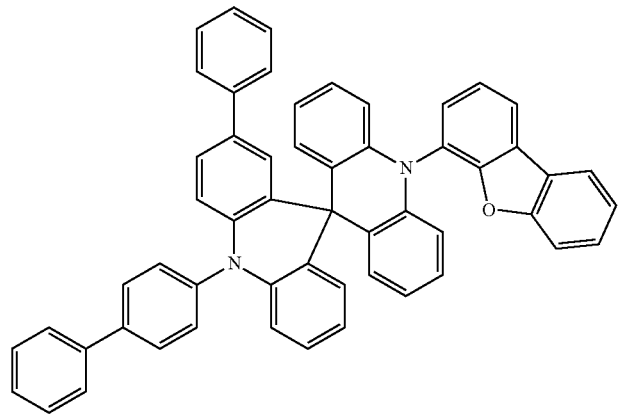 [SMILES: c1ccc(-c2ccc(N3c4ccccc4C4(c5cc(-c6ccccc6)ccc53)c3ccccc3N(c3cccc5c3oc3ccccc35)c3ccccc34)cc2)cc1]
19
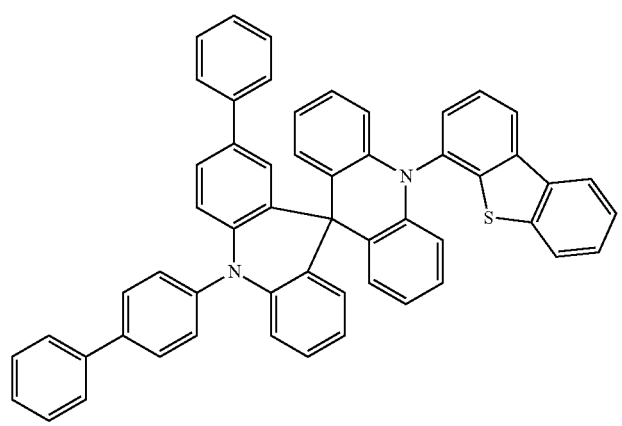
20
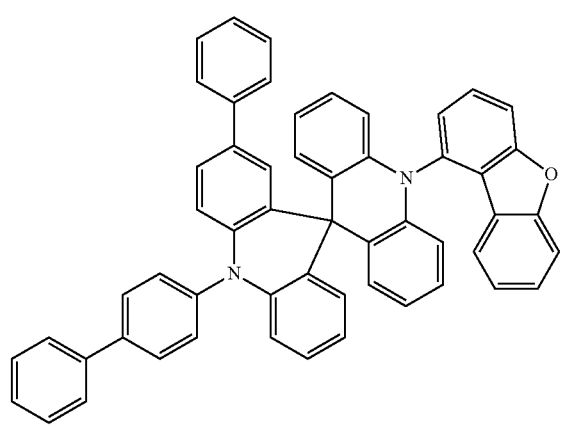 [SMILES: c1ccc(-c2ccc(N3c4ccccc4C4(c5cc(-c6ccccc6)ccc53)c3ccccc3N(c3cccc5oc6ccccc6c35)c3ccccc34)cc2)cc1]
21

22
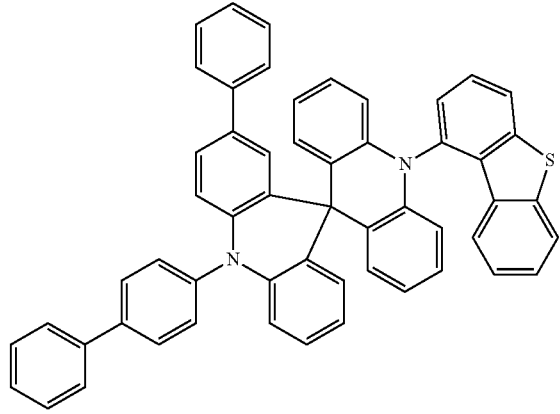 [SMILES: c1ccc(-c2ccc(N3c4ccccc4C4(c5cc(-c6ccccc6)ccc53)c3ccccc3N(c3cccc5sc6ccccc6c35)c3ccccc34)cc2)cc1]
23
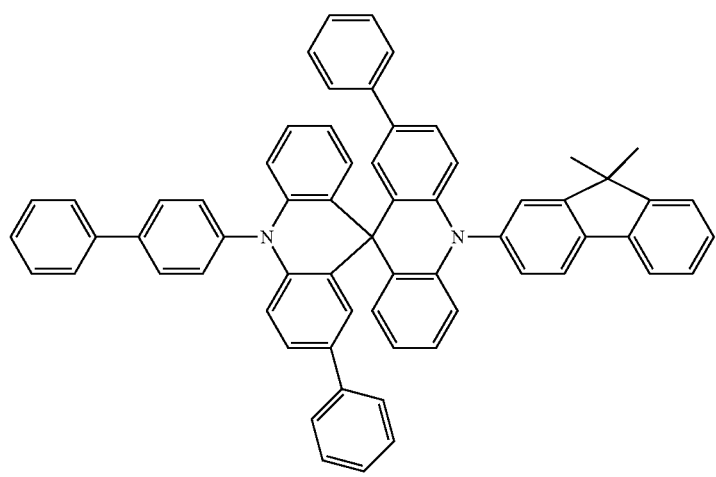 [SMILES: CC1(C)c2ccccc2-c2ccc(N3c4ccccc4C4(c5ccccc5N(c5ccc(-c6ccccc6)cc5)c5ccc(-c6ccccc6)cc54)c4cc(-c5ccccc5)ccc43)cc21]
24
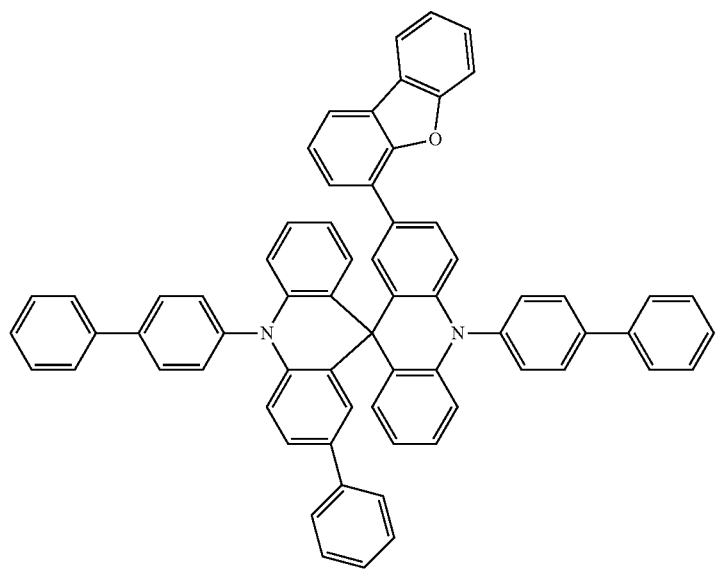 [SMILES: c1ccc(-c2ccc(N3c4ccccc4C4(c5ccccc5N(c5ccc(-c6ccccc6)cc5)c5ccc(-c6cccc7c6oc6ccccc67)cc54)c4cc(-c5ccccc5)ccc43)cc2)cc1]

-continued
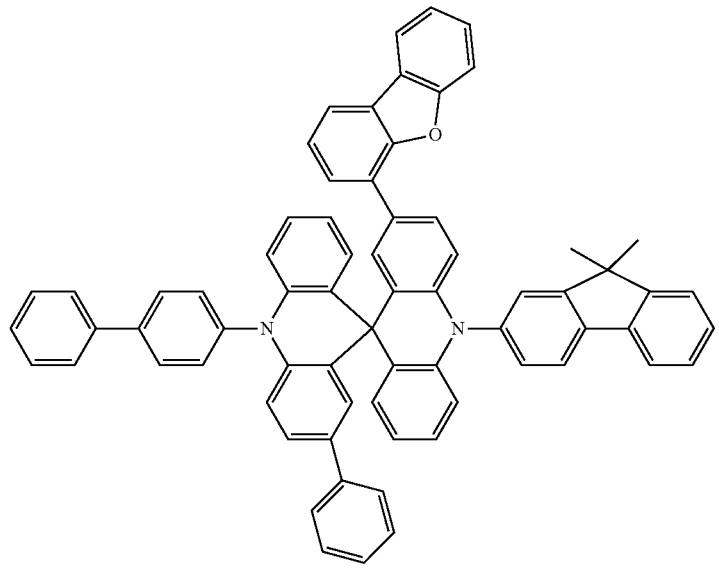 [SMILES: CC1(C)c2ccccc2-c2ccc(N3c4ccccc4C4(c5ccccc5N(c5ccc(-c6ccccc6)cc5)c5ccc(-c6ccccc6)cc54)c4cc(-c5cccc6c5oc5ccccc56)ccc43)cc21]
25
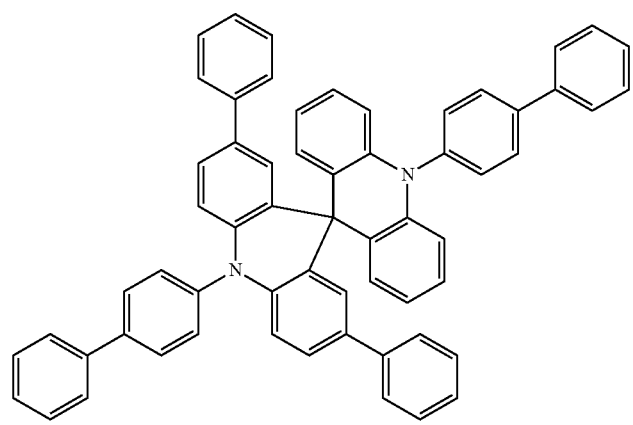 [SMILES: c1ccc(-c2ccc(N3c4ccccc4C4(c5ccccc53)c3cc(-c5ccccc5)ccc3N(c3ccc(-c5ccccc5)cc3)c3ccc(-c5ccccc5)cc34)cc2)cc1]
26
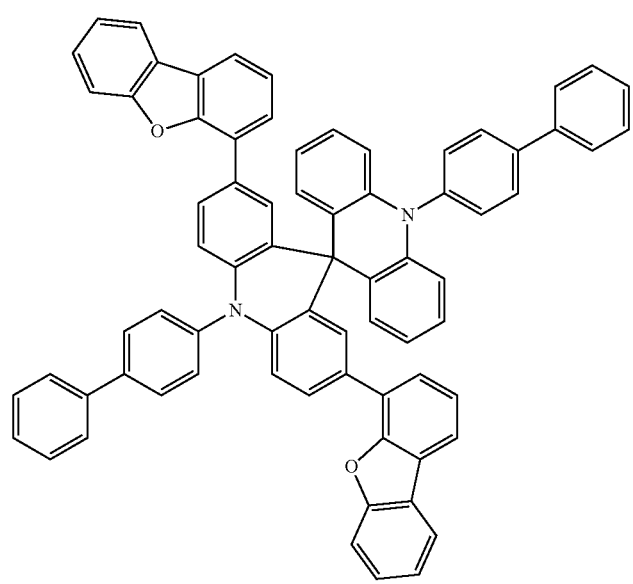 [SMILES: c1ccc(-c2ccc(N3c4ccccc4C4(c5ccccc53)c3cc(-c5cccc6c5oc5ccccc56)ccc3N(c3ccc(-c5ccccc5)cc3)c3ccc(-c5cccc6c5oc5ccccc56)cc34)cc2)cc1]
27

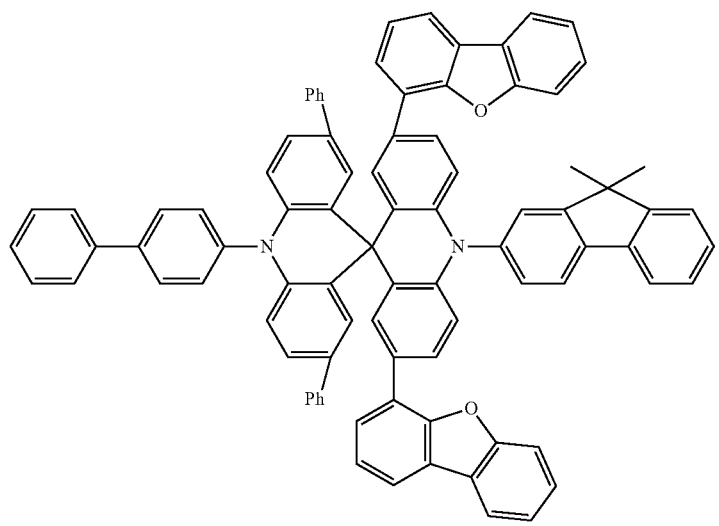 [SMILES: CC1(C)c2ccccc2-c2ccc(N3c4ccc(-c5cccc6c5oc5ccccc56)cc4C4(c5cc(-c6ccccc6)ccc5N(c5ccc(-c6ccccc6)cc5)c5ccc(-c6ccccc6)cc54)c4cc(-c5cccc6c5oc5ccccc56)ccc43)cc21]
28
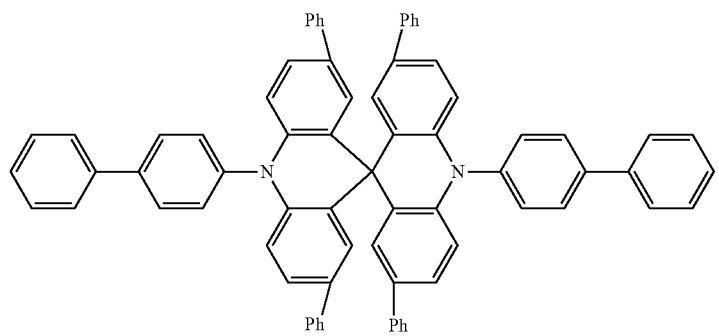 [SMILES: c1ccc(-c2ccc(N3c4ccc(-c5ccccc5)cc4C4(c5cc(-c6ccccc6)ccc53)c3cc(-c5ccccc5)ccc3N(c3ccc(-c5ccccc5)cc3)c3ccc(-c5ccccc5)cc34)cc2)cc1]
29
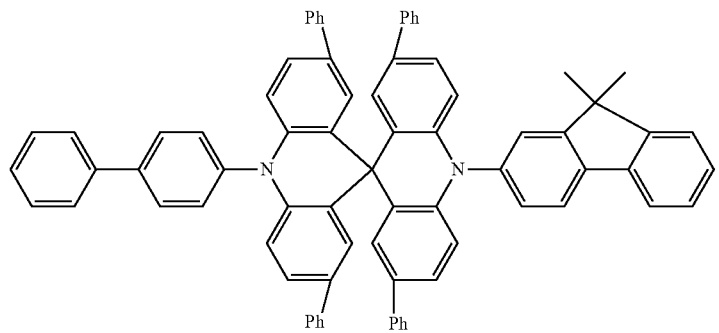 [SMILES: CC1(C)c2ccccc2-c2ccc(N3c4ccc(-c5ccccc5)cc4C4(c5cc(-c6ccccc6)ccc5N(c5ccc(-c6ccccc6)cc5)c5ccc(-c6ccccc6)cc54)c4cc(-c5ccccc5)ccc43)cc21]
30

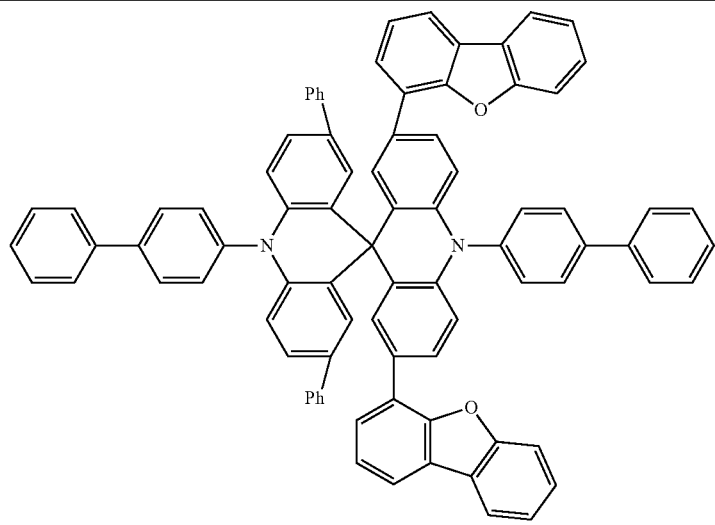
31
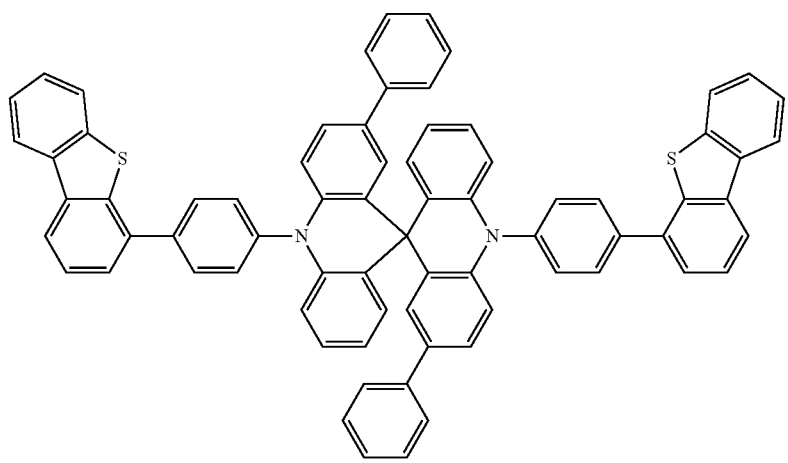
32
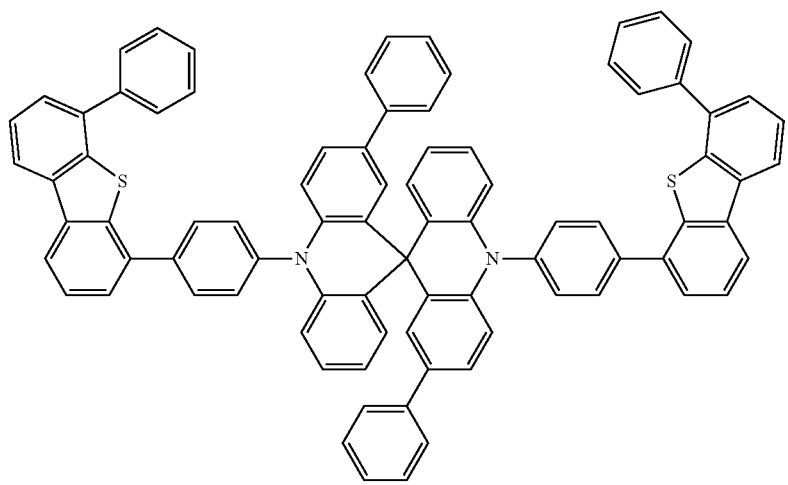
33

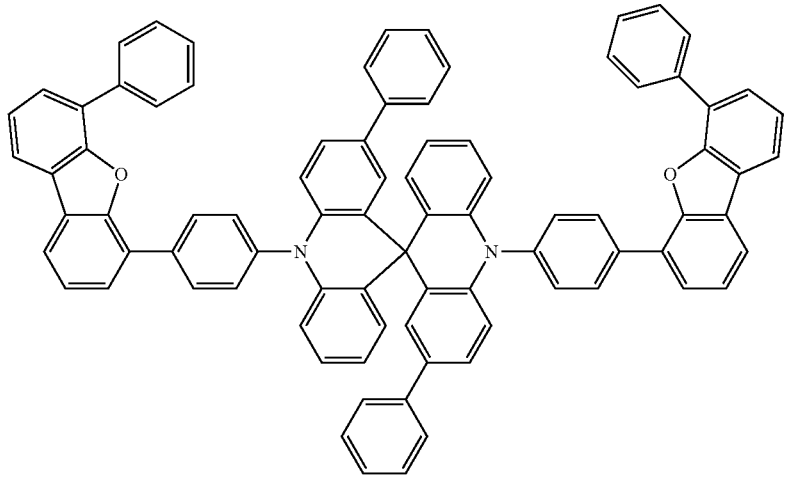 [SMILES: c1ccc(-c2ccc3c(c2)C2(c4ccccc4N3c3ccc(-c4cccc5c4oc4c(-c6ccccc6)cccc45)cc3)c3ccccc3N(c3ccc(-c4cccc5c4oc4c(-c6ccccc6)cccc45)cc3)c3ccc(-c4ccccc4)cc32)cc1]
34
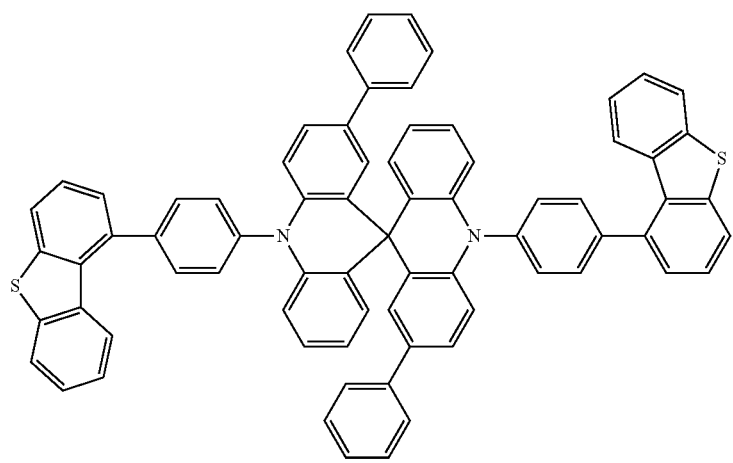 [SMILES: c1ccc(-c2ccc3c(c2)C2(c4ccccc4N3c3ccc(-c4cccc5sc6ccccc6c45)cc3)c3ccccc3N(c3ccc(-c4cccc5sc6ccccc6c45)cc3)c3ccc(-c4ccccc4)cc32)cc1]
35
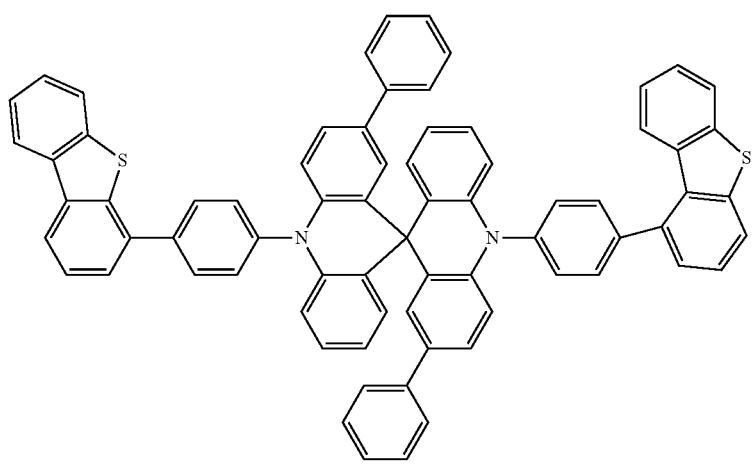 [SMILES: c1ccc(-c2ccc3c(c2)C2(c4ccccc4N3c3ccc(-c4cccc5c4sc4ccccc45)cc3)c3ccccc3N(c3ccc(-c4cccc5sc6ccccc6c45)cc3)c3ccc(-c4ccccc4)cc32)cc1]
36

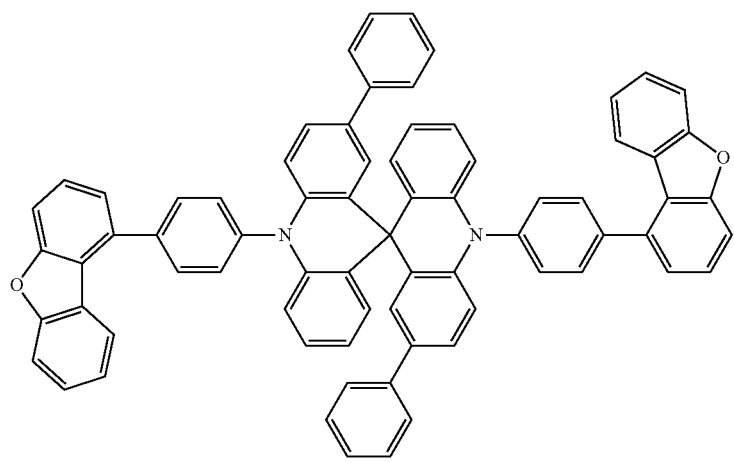
37
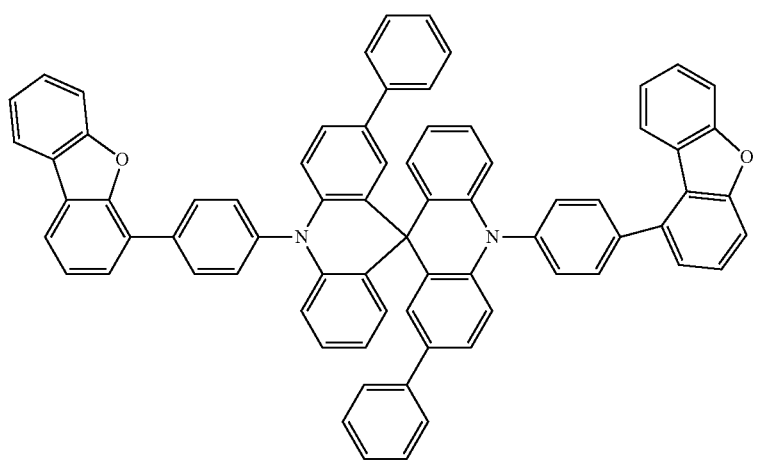 [SMILES: c1ccc(-c2ccc3c(c2)C2(c4ccccc4N3c3ccc(-c4cccc5c4oc4ccccc45)cc3)c3ccccc3N(c3ccc(-c4cccc5oc6ccccc6c45)cc3)c3ccc(-c4ccccc4)cc32)cc1]
38
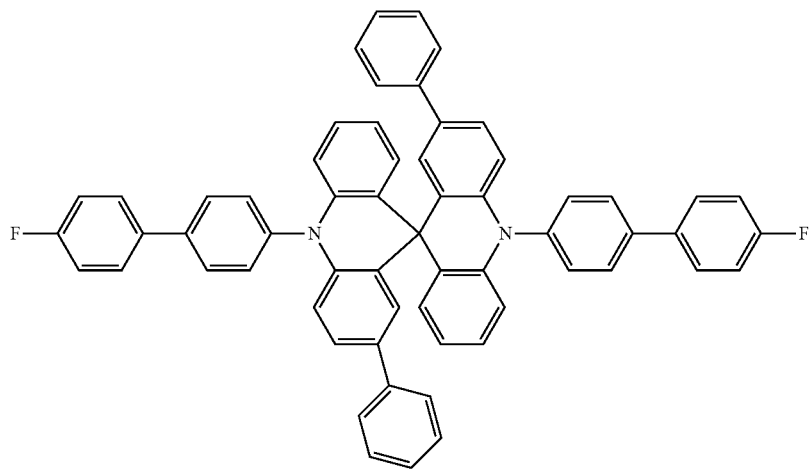 [SMILES: Fc1ccc(-c2ccc(N3c4ccccc4C4(c5ccccc5N(c5ccc(-c6ccc(F)cc6)cc5)c5ccc(-c6ccccc6)cc54)c4cc(-c5ccccc5)ccc43)cc2)cc1]
39

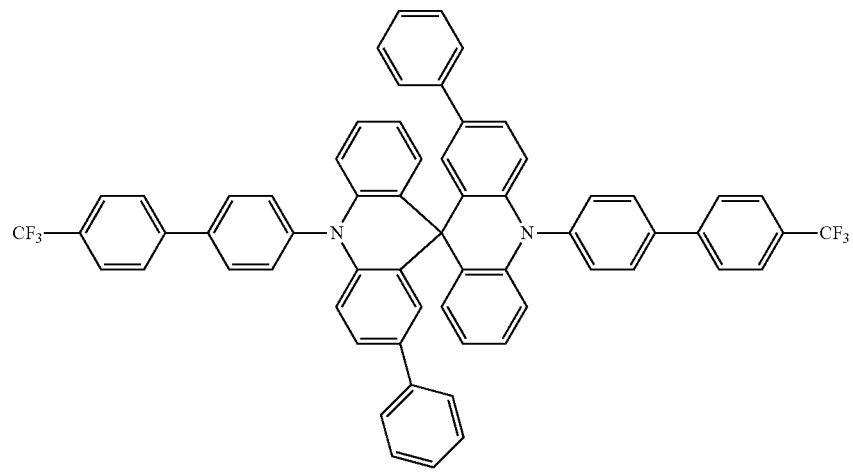 [SMILES: FC(F)(F)c1ccc(-c2ccc(N3c4ccccc4C4(c5ccccc5N(c5ccc(-c6ccc(C(F)(F)F)cc6)cc5)c5ccc(-c6ccccc6)cc54)c4cc(-c5ccccc5)ccc43)cc2)cc1]
40
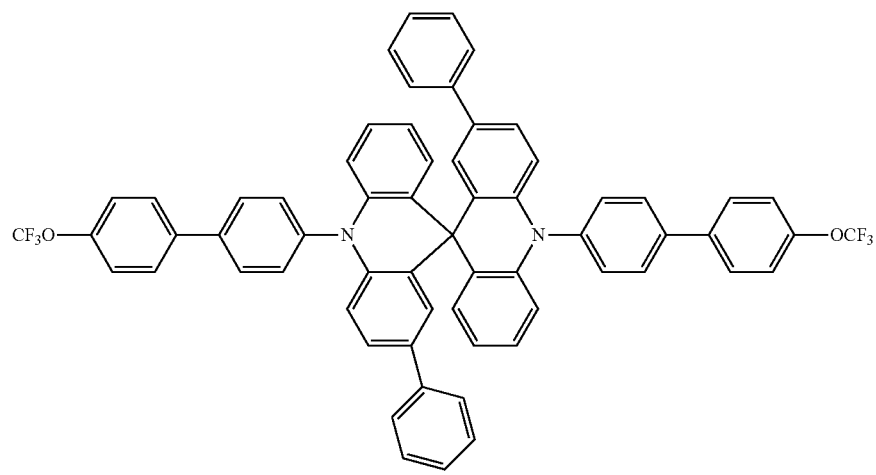
41
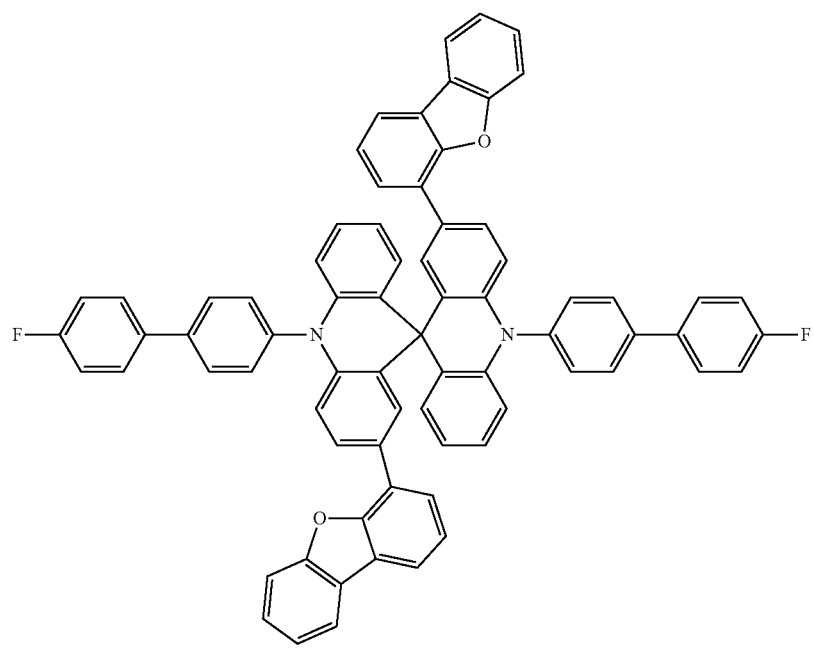 [SMILES: Fc1ccc(-c2ccc(N3c4ccccc4C4(c5ccccc5N(c5ccc(-c6ccc(F)cc6)cc5)c5ccc(-c6cccc7c6oc6ccccc67)cc54)c4cc(-c5cccc6c5oc5ccccc56)ccc43)cc2)cc1]
42

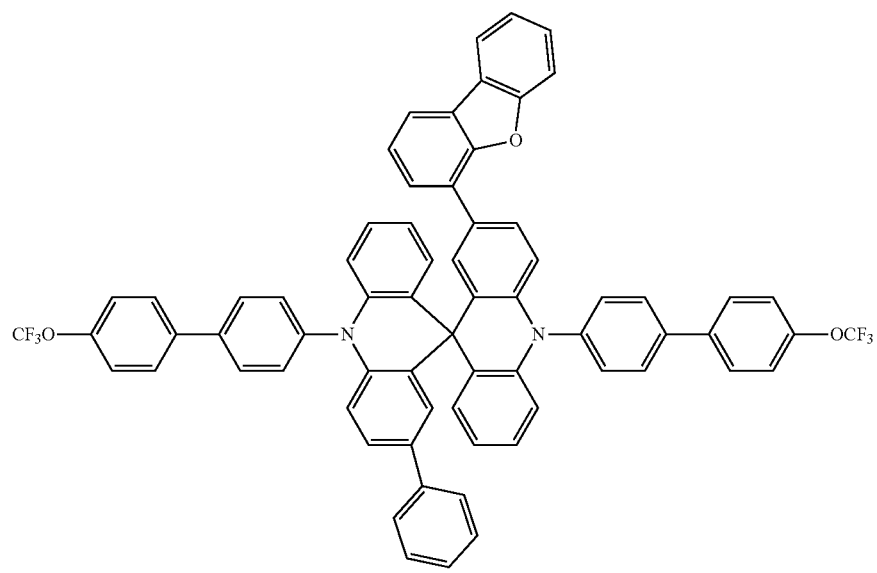
43
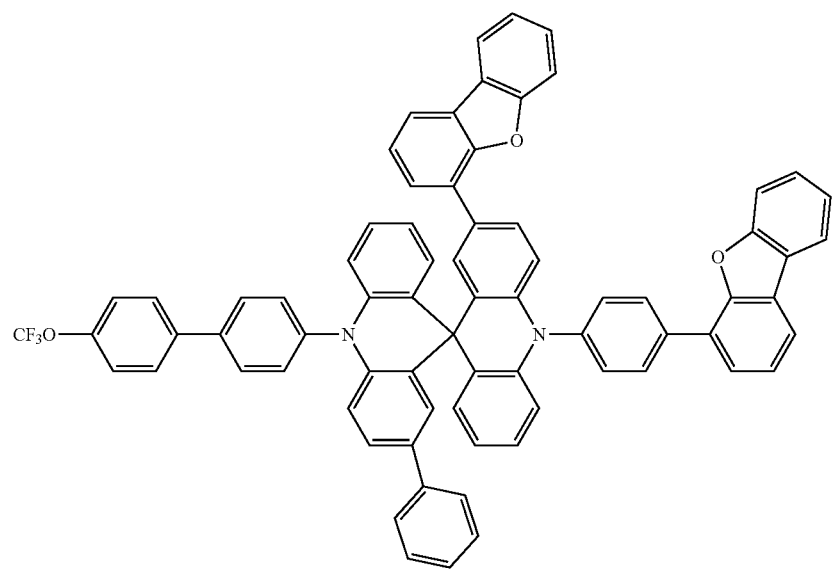
44
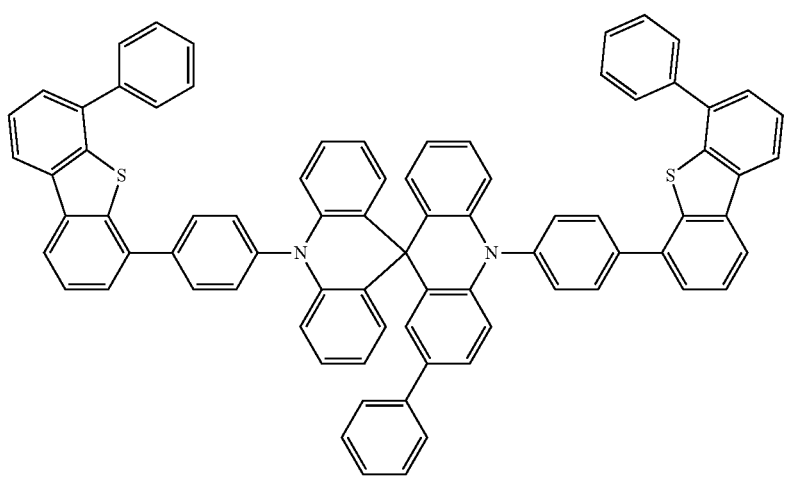 [SMILES: c1ccc(-c2ccc3c(c2)C2(c4ccccc4N(c4ccc(-c5cccc6c5sc5c(-c7ccccc7)cccc56)cc4)c4ccccc42)c2ccccc2N3c2ccc(-c3cccc4c3sc3c(-c5ccccc5)cccc34)cc2)cc1]
45

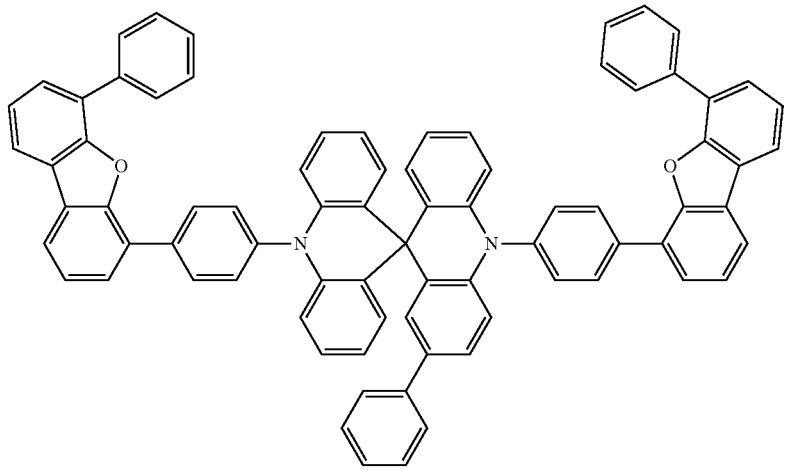
46
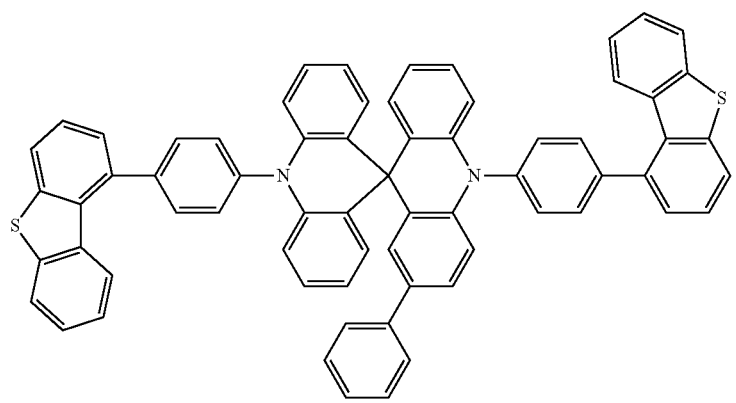 [SMILES: c1ccc(-c2ccc3c(c2)C2(c4ccccc4N(c4ccc(-c5cccc6sc7ccccc7c56)cc4)c4ccccc42)c2ccccc2N3c2ccc(-c3cccc4sc5ccccc5c34)cc2)cc1]
47
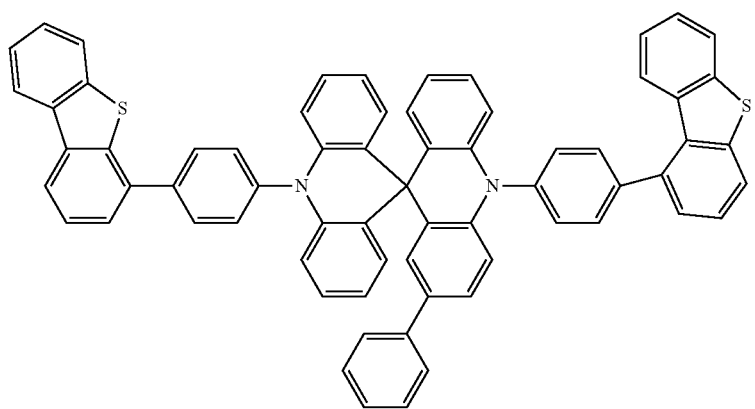 [SMILES: c1ccc(-c2ccc3c(c2)C2(c4ccccc4N(c4ccc(-c5cccc6c5sc5ccccc56)cc4)c4ccccc42)c2ccccc2N3c2ccc(-c3cccc4sc5ccccc5c34)cc2)cc1]
48

-continued
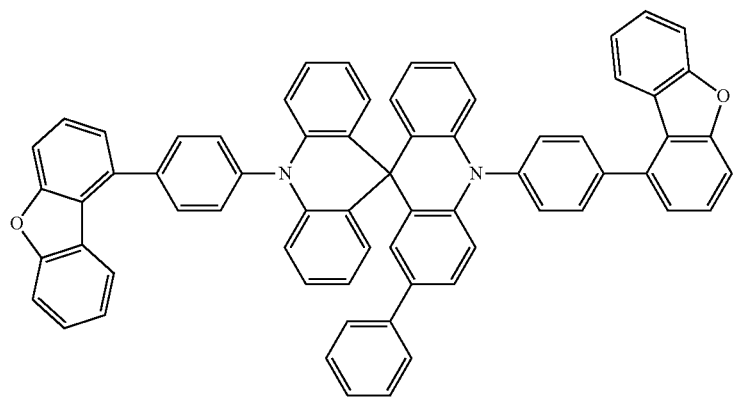 [SMILES: c1ccc(-c2ccc3c(c2)C2(c4ccccc4N(c4ccc(-c5cccc6oc7ccccc7c56)cc4)c4ccccc42)c2ccccc2N3c2ccc(-c3cccc4oc5ccccc5c34)cc2)cc1]
49
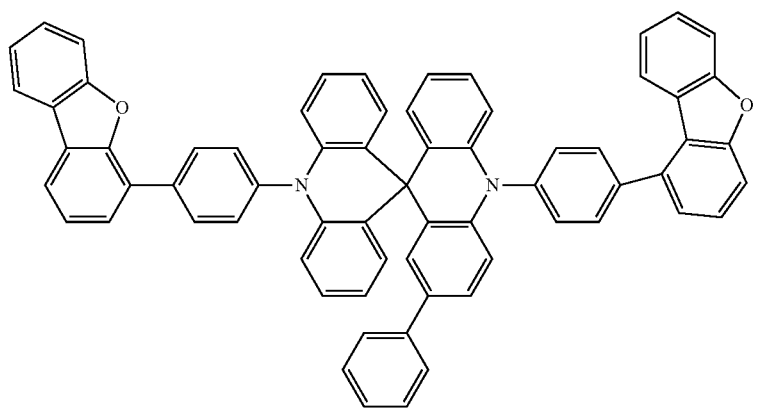 [SMILES: c1ccc(-c2ccc3c(c2)C2(c4ccccc4N(c4ccc(-c5cccc6c5oc5ccccc56)cc4)c4ccccc42)c2ccccc2N3c2ccc(-c3cccc4oc5ccccc5c34)cc2)cc1]
50
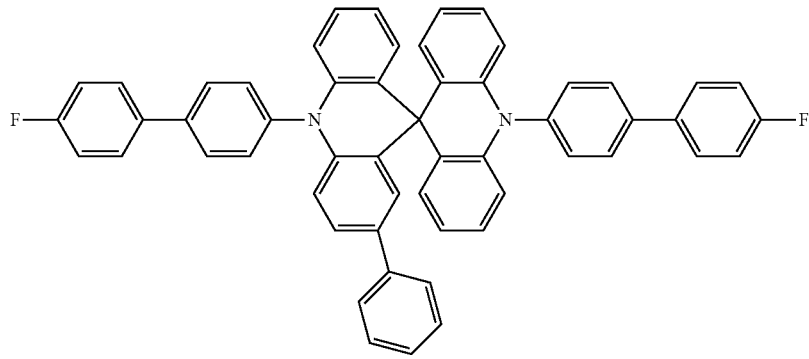 [SMILES: Fc1ccc(-c2ccc(N3c4ccccc4C4(c5ccccc53)c3ccccc3N(c3ccc(-c5ccc(F)cc5)cc3)c3ccc(-c5ccccc5)cc34)cc2)cc1]
51
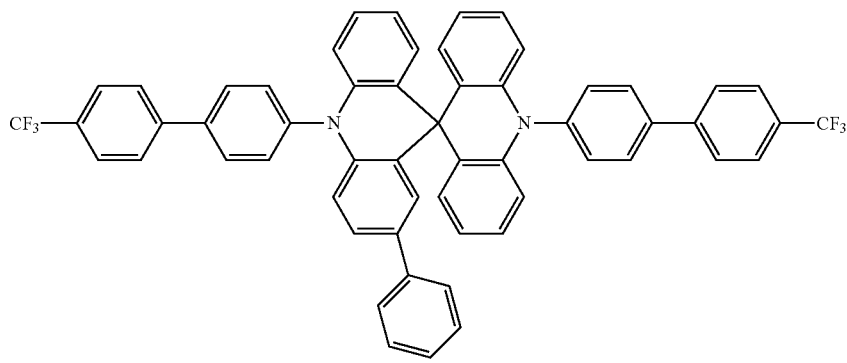 [SMILES: FC(F)(F)c1ccc(-c2ccc(N3c4ccccc4C4(c5ccccc53)c3ccccc3N(c3ccc(-c5ccc(C(F)(F)F)cc5)cc3)c3ccc(-c5ccccc5)cc34)cc2)cc1]
52

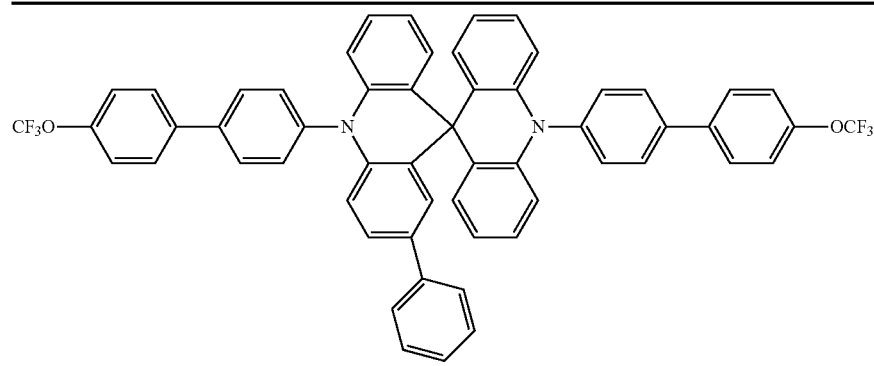
53
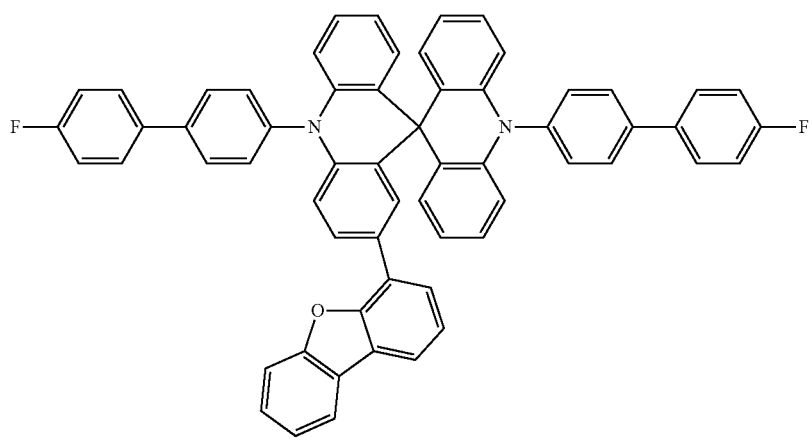 [SMILES: Fc1ccc(-c2ccc(N3c4ccccc4C4(c5ccccc53)c3ccccc3N(c3ccc(-c5ccc(F)cc5)cc3)c3ccc(-c5cccc6c5oc5ccccc56)cc34)cc2)cc1]
54
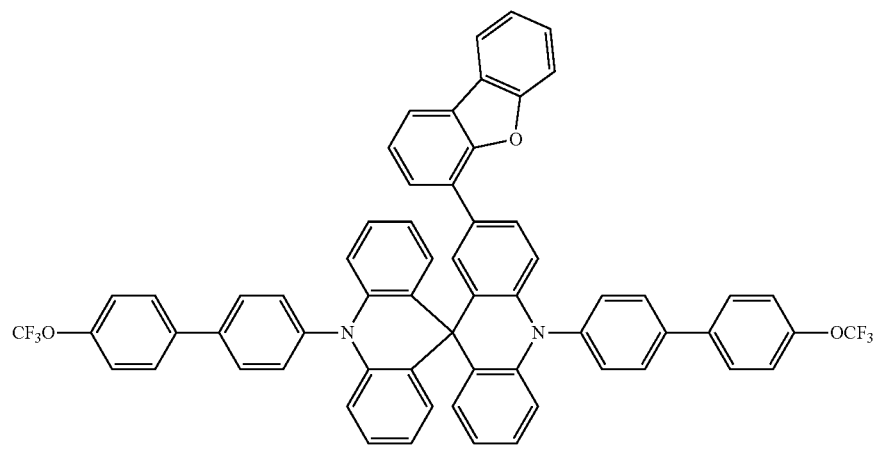
55
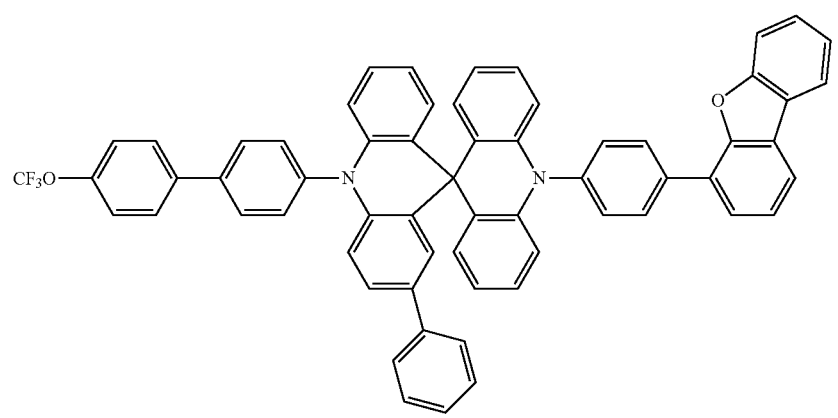
56

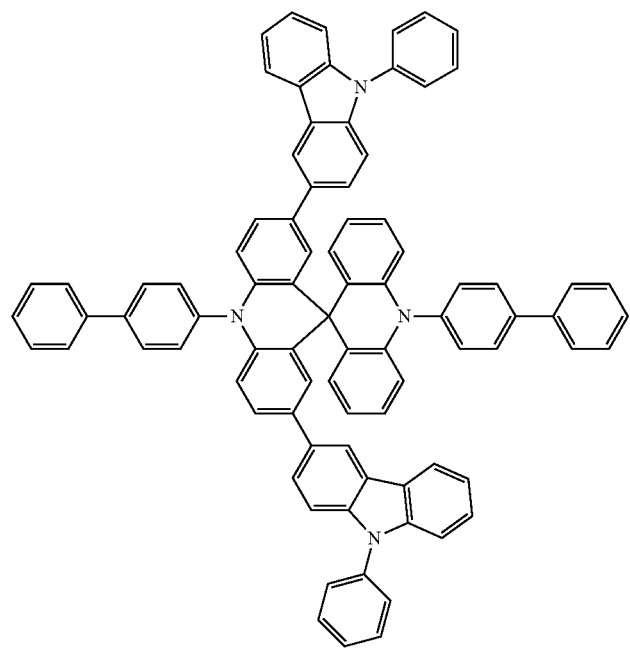 [SMILES: c1ccc(-c2ccc(N3c4ccccc4C4(c5ccccc53)c3cc(-c5ccc6c(c5)c5ccccc5n6-c5ccccc5)ccc3N(c3ccc(-c5ccccc5)cc3)c3ccc(-c5ccc6c(c5)c5ccccc5n6-c5ccccc5)cc34)cc2)cc1]
57
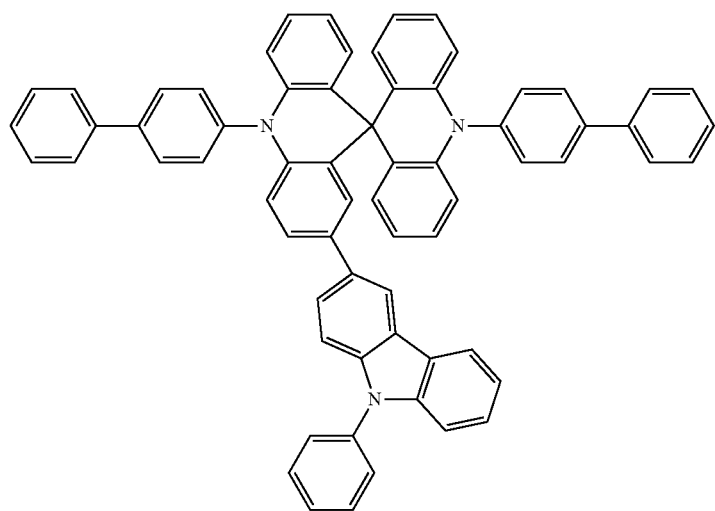 [SMILES: c1ccc(-c2ccc(N3c4ccccc4C4(c5ccccc53)c3ccccc3N(c3ccc(-c5ccccc5)cc3)c3ccc(-c5ccc6c(c5)c5ccccc5n6-c5ccccc5)cc34)cc2)cc1]
58

-continued
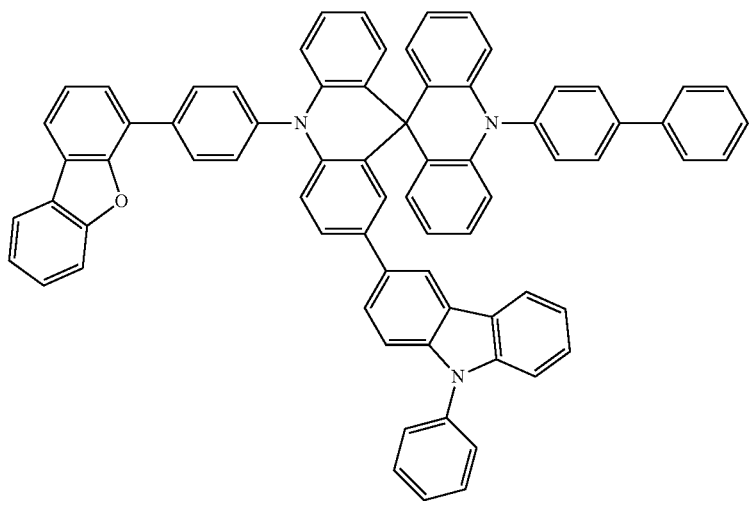 [SMILES: c1ccc(-c2ccc(N3c4ccccc4C4(c5ccccc53)c3ccccc3N(c3ccc(-c5cccc6c5oc5ccccc56)cc3)c3ccc(-c5ccc6c(c5)c5ccccc5n6-c5ccccc5)cc34)cc2)cc1]
59
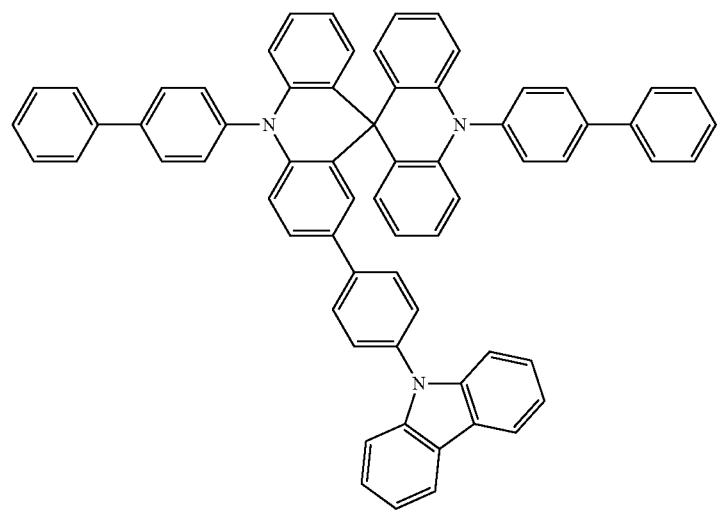 [SMILES: c1ccc(-c2ccc(N3c4ccccc4C4(c5ccccc53)c3ccccc3N(c3ccc(-c5ccccc5)cc3)c3ccc(-c5ccc(-n6c7ccccc7c7ccccc76)cc5)cc34)cc2)cc1]
60
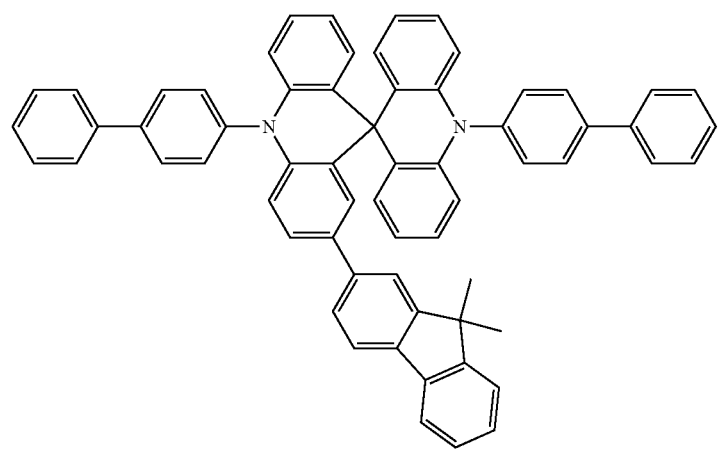 [SMILES: CC1(C)c2ccccc2-c2ccc(-c3ccc4c(c3)C3(c5ccccc5N(c5ccc(-c6ccccc6)cc5)c5ccccc53)c3ccccc3N4c3ccc(-c4ccccc4)cc3)cc21]
61

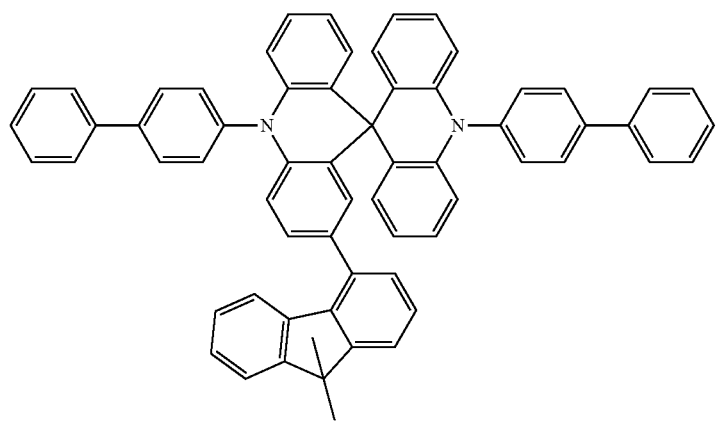
62
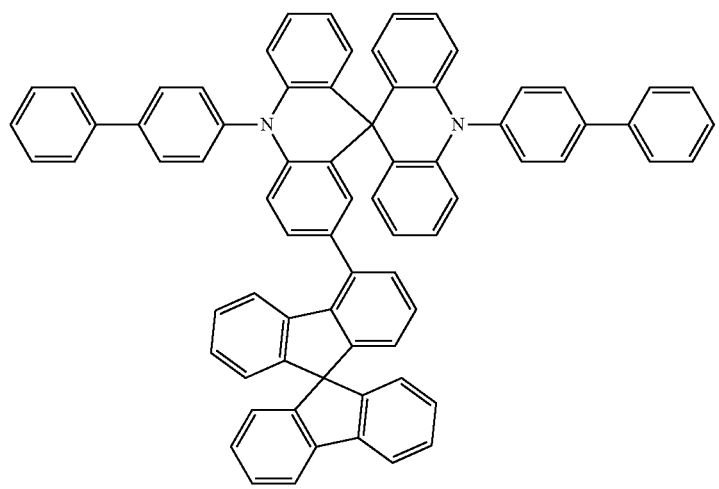 [SMILES: c1ccc(-c2ccc(N3c4ccccc4C4(c5ccccc53)c3ccccc3N(c3ccc(-c5ccccc5)cc3)c3ccc(-c5cccc6c5-c5ccccc5C65c6ccccc6-c6ccccc65)cc34)cc2)cc1]
63
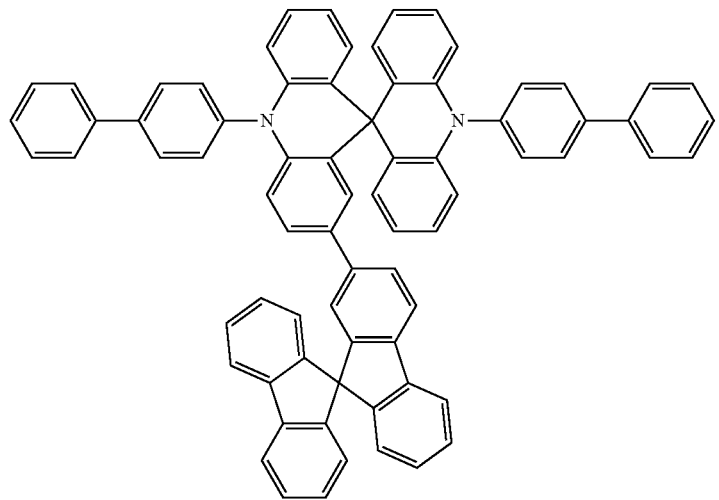 [SMILES: c1ccc(-c2ccc(N3c4ccccc4C4(c5ccccc53)c3ccccc3N(c3ccc(-c5ccccc5)cc3)c3ccc(-c5ccc6c(c5)C5(c7ccccc7-c7ccccc75)c5ccccc5-6)cc34)cc2)cc1]
64

-continued
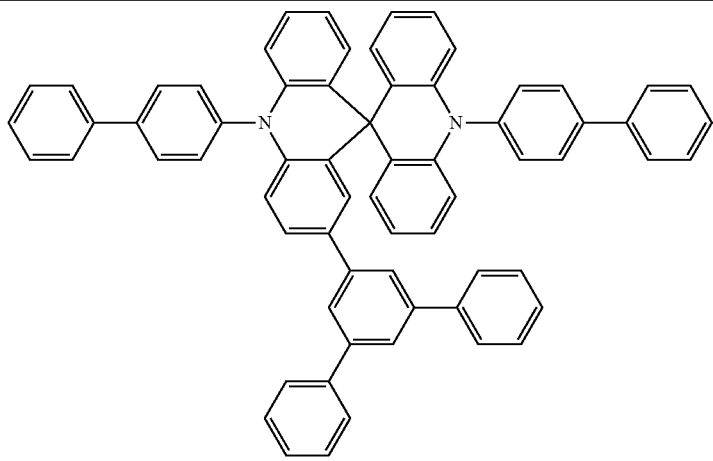
65
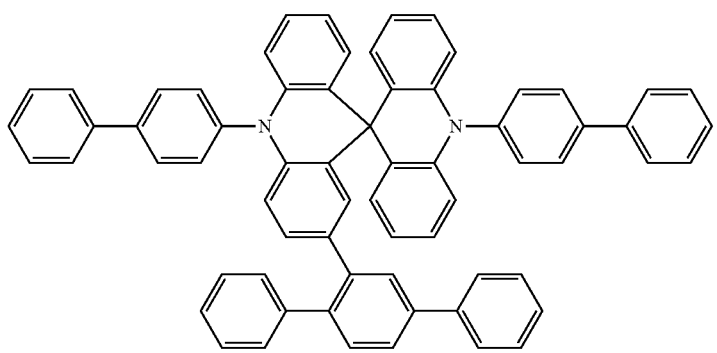 [SMILES: c1ccc(-c2ccc(N3c4ccccc4C4(c5ccccc53)c3ccccc3N(c3ccc(-c5ccccc5)cc3)c3ccc(-c5cc(-c6ccccc6)ccc5-c5ccccc5)cc34)cc2)cc1]
66
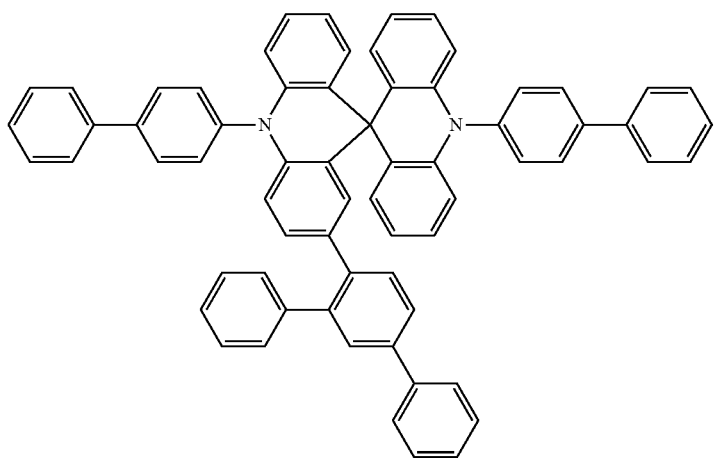 [SMILES: c1ccc(-c2ccc(N3c4ccccc4C4(c5ccccc53)c3ccccc3N(c3ccc(-c5ccccc5)cc3)c3ccc(-c5ccc(-c6ccccc6)cc5-c5ccccc5)cc34)cc2)cc1]
67
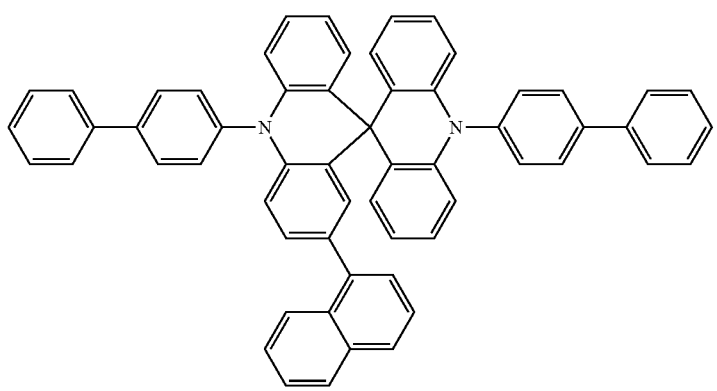 [SMILES: c1ccc(-c2ccc(N3c4ccccc4C4(c5ccccc53)c3ccccc3N(c3ccc(-c5ccccc5)cc3)c3ccc(-c5cccc6ccccc56)cc34)cc2)cc1]
68

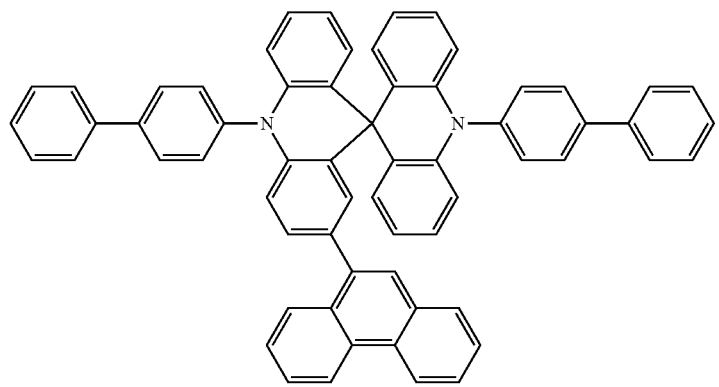 [SMILES: c1ccc(-c2ccc(N3c4ccccc4C4(c5ccccc53)c3ccccc3N(c3ccc(-c5ccccc5)cc3)c3ccc(-c5cc6ccccc6c6ccccc56)cc34)cc2)cc1]
69
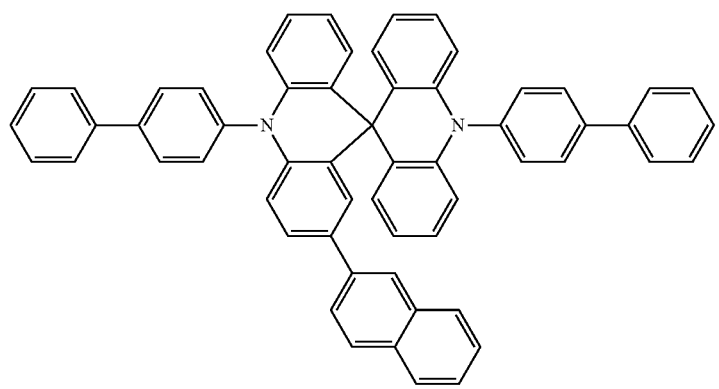 [SMILES: c1ccc(-c2ccc(N3c4ccccc4C4(c5ccccc53)c3ccccc3N(c3ccc(-c5ccccc5)cc3)c3ccc(-c5ccc6ccccc6c5)cc34)cc2)cc1]
70
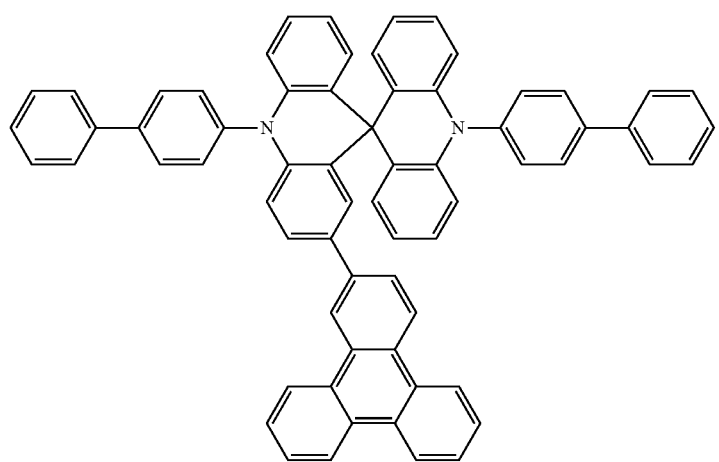 [SMILES: c1ccc(-c2ccc(N3c4ccccc4C4(c5ccccc53)c3ccccc3N(c3ccc(-c5ccccc5)cc3)c3ccc(-c5ccc6c7ccccc7c7ccccc7c6c5)cc34)cc2)cc1]
71

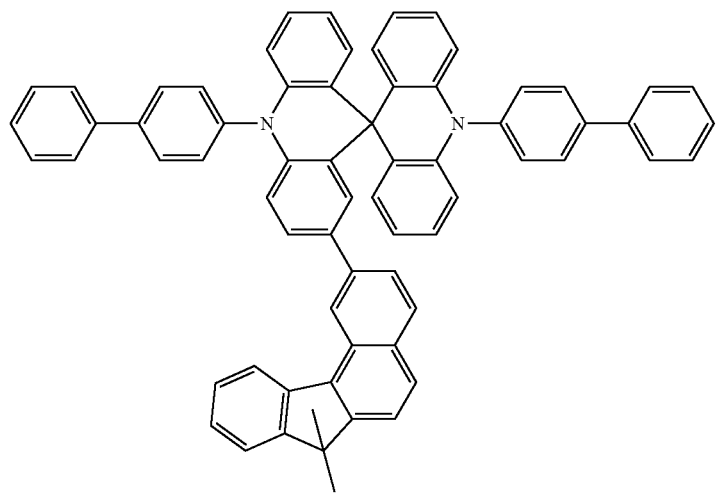
72
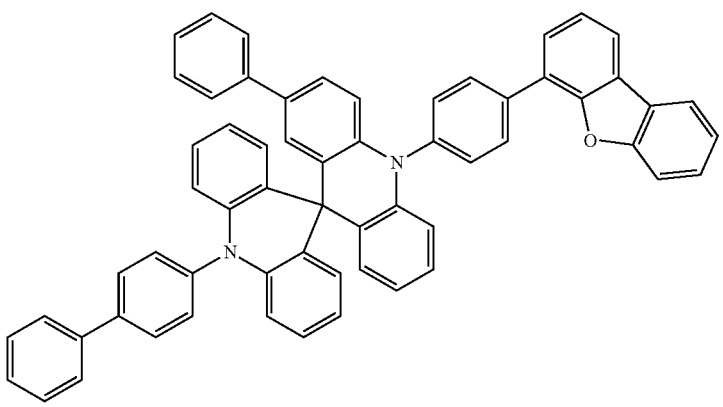 [SMILES: c1ccc(-c2ccc(N3c4ccccc4C4(c5ccccc53)c3ccccc3N(c3ccc(-c5cccc6c5oc5ccccc56)cc3)c3ccc(-c5ccccc5)cc34)cc2)cc1]
73
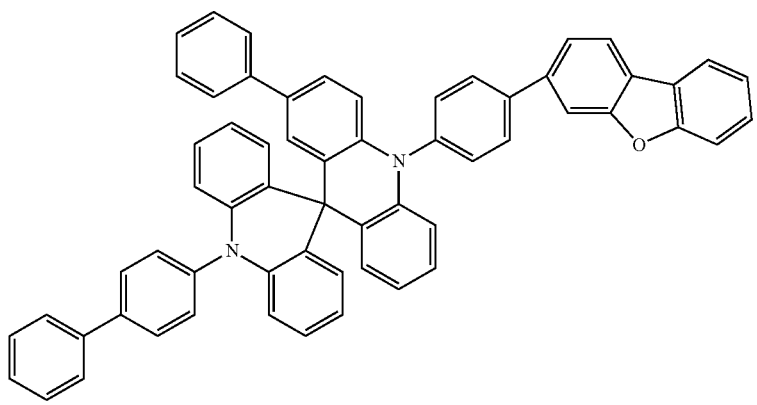 [SMILES: c1ccc(-c2ccc(N3c4ccccc4C4(c5ccccc53)c3ccccc3N(c3ccc(-c5ccc6c(c5)oc5ccccc56)cc3)c3ccc(-c5ccccc5)cc34)cc2)cc1]
74

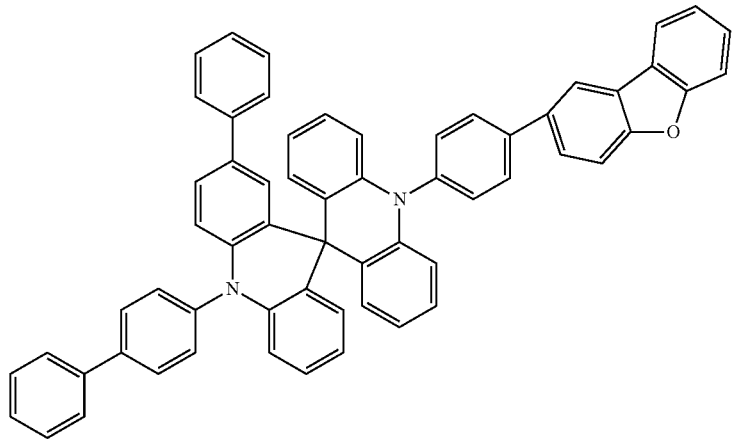 [SMILES: c1ccc(-c2ccc(N3c4ccccc4C4(c5ccccc5N(c5ccc(-c6ccc7oc8ccccc8c7c6)cc5)c5ccccc54)c4cc(-c5ccccc5)ccc43)cc2)cc1]
75
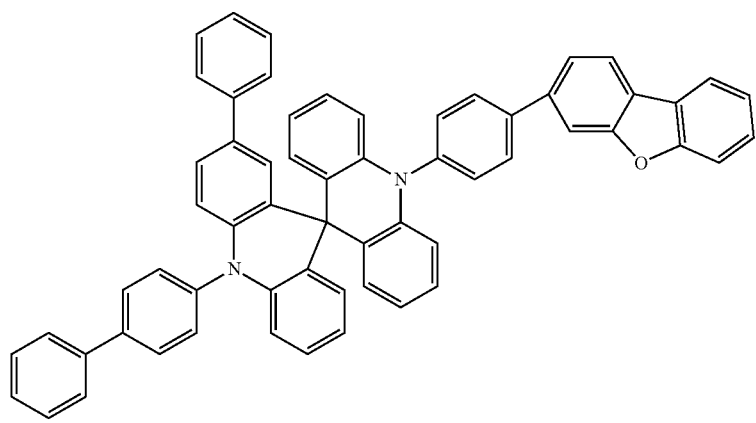 [SMILES: c1ccc(-c2ccc(N3c4ccccc4C4(c5ccccc5N(c5ccc(-c6ccc7c(c6)oc6ccccc67)cc5)c5ccccc54)c4cc(-c5ccccc5)ccc43)cc2)cc1]
76
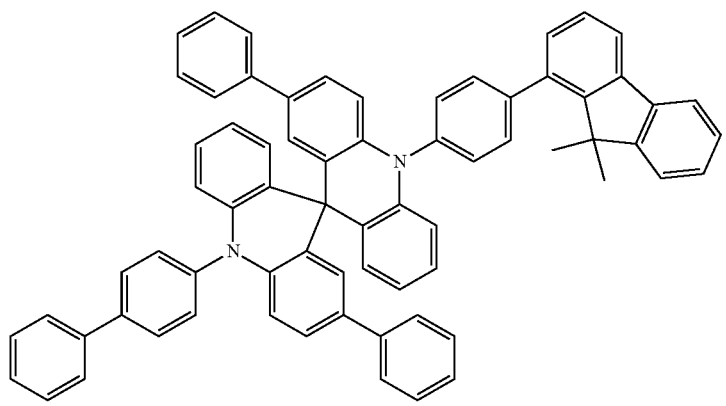 [SMILES: CC1(C)c2ccccc2-c2cccc(-c3ccc(N4c5ccccc5C5(c6ccccc6N(c6ccc(-c7ccccc7)cc6)c6ccc(-c7ccccc7)cc65)c5cc(-c6ccccc6)ccc54)cc3)c21]
77

78
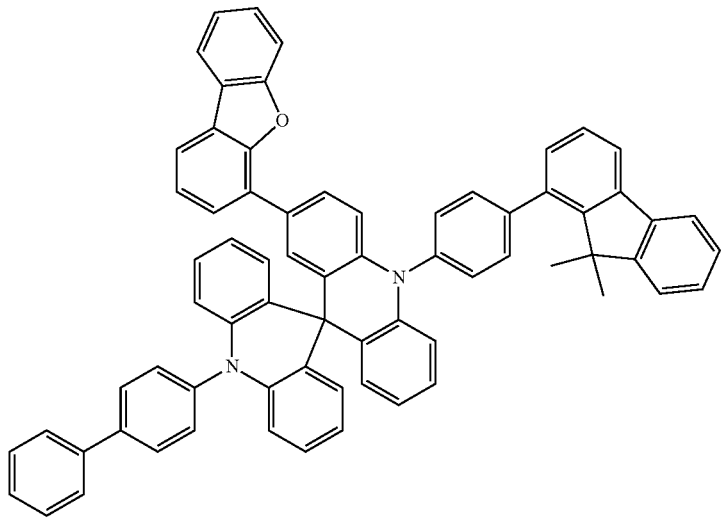 [SMILES: CC1(C)c2ccccc2-c2cccc(-c3ccc(N4c5ccccc5C5(c6ccccc6N(c6ccc(-c7ccccc7)cc6)c6ccccc65)c5cc(-c6cccc7c6oc6ccccc67)ccc54)cc3)c21]
79
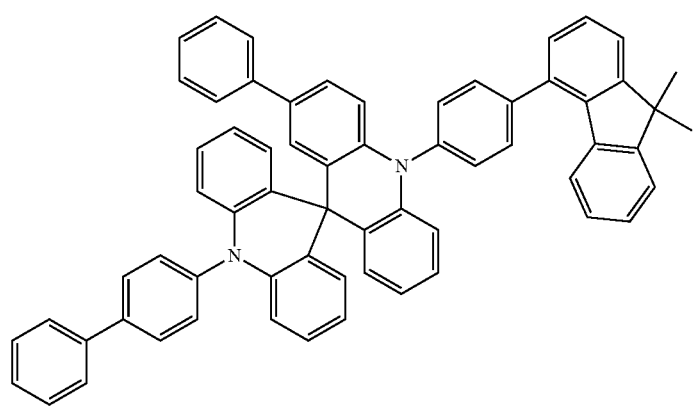 [SMILES: CC1(C)c2ccccc2-c2c(-c3ccc(N4c5ccccc5C5(c6ccccc6N(c6ccc(-c7ccccc7)cc6)c6ccccc65)c5cc(-c6ccccc6)ccc54)cc3)cccc21]
80
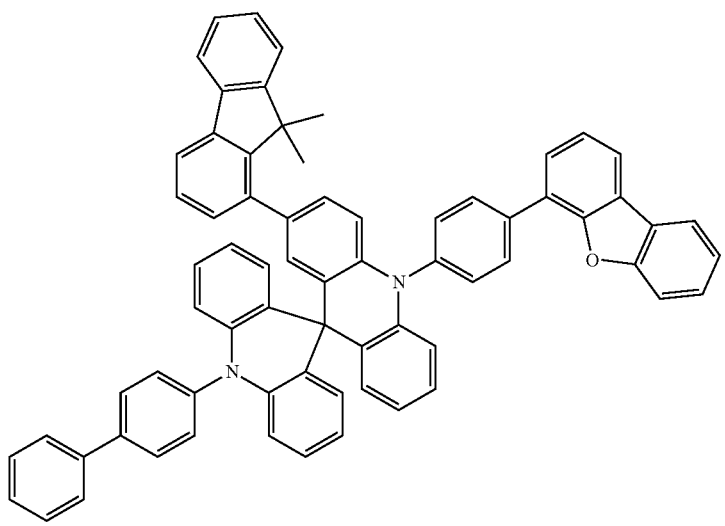 [SMILES: CC1(C)c2ccccc2-c2cccc(-c3ccc4c(c3)C3(c5ccccc5N(c5ccc(-c6ccccc6)cc5)c5ccccc53)c3ccccc3N4c3ccc(-c4cccc5c4oc4ccccc45)cc3)c21]

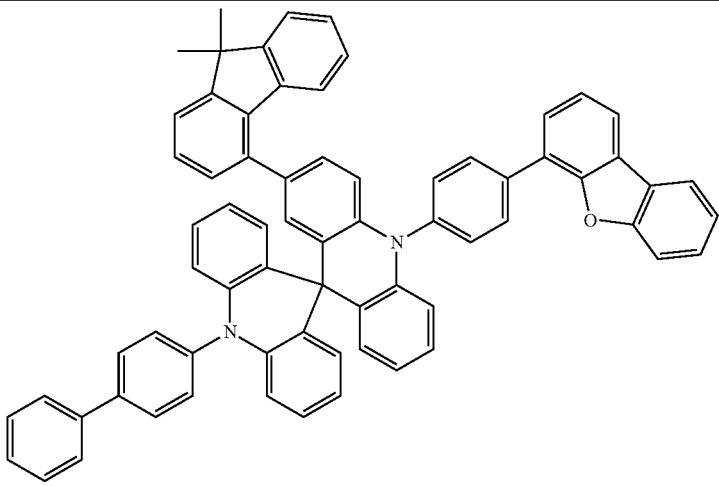

81

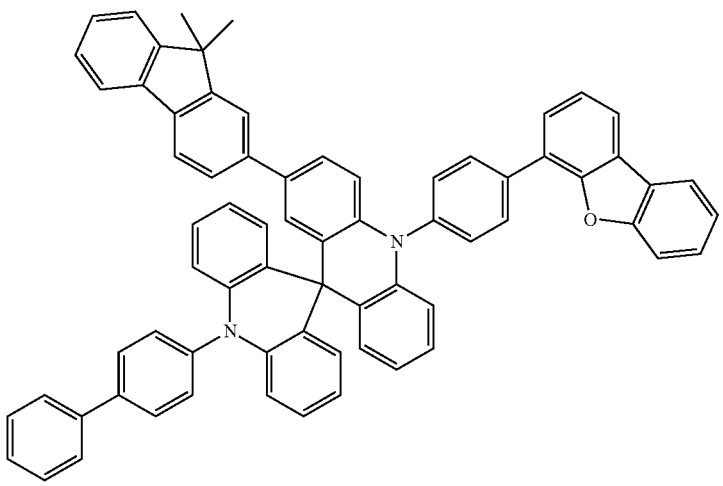 [SMILES: CC1(C)c2ccccc2-c2ccc(-c3ccc4c(c3)C3(c5ccccc5N(c5ccc(-c6ccccc6)cc5)c5ccccc53)c3ccccc3N4c3ccc(-c4cccc5c4oc4ccccc45)cc3)cc21]

82

The compounds of the formula (I) can be prepared using known reactions of organic chemistry, for example using bromination reactions, Buchwald coupling reactions and Suzuki coupling reactions.

Preferred processes for the preparation of the compounds of the formula (I) are presented and explained in general terms below. In the schemes, the compounds shown may optionally be substituted. Explicit examples of the said processes are shown in the working examples.

A preferred process for the preparation of compounds of the formula (I) begins with acridinone or a derivative of acridinone (Scheme 1). This is reacted In a Buchwald coupling, where an acridinone substituted by an aryl group on N is obtained. This is brominated in a further step, and aryl groups are introduced at the brominated positions in a Suzuki reaction. This route preferably gives symmetrical acridinone intermediates.

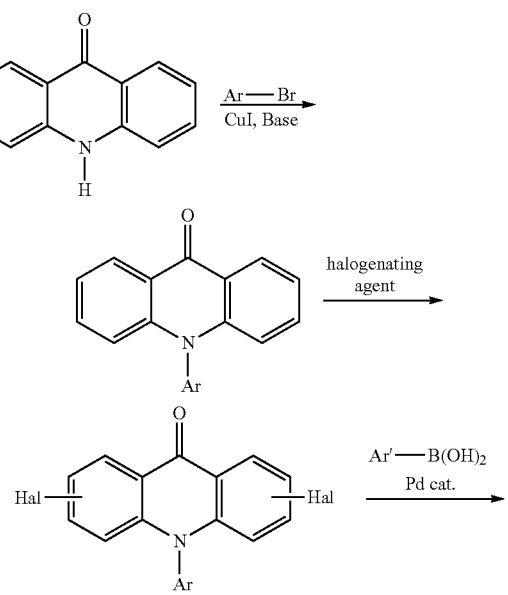

Schema 1

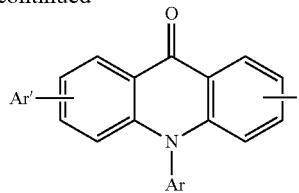

Ar, Ar': any desired aromatic or heteroaromatic ring system
Hal: halogen atom or other reactive group Asymmetrical acridinone basic structures can be prepared in accordance with Scheme 2. To this end, the starting material is a diphenylamine derivative, which is converted into a carboxyl-substituted triphenyl derivative. This can be converted in a ring-closure reaction into an asymmetrically substituted acridinone derivative.

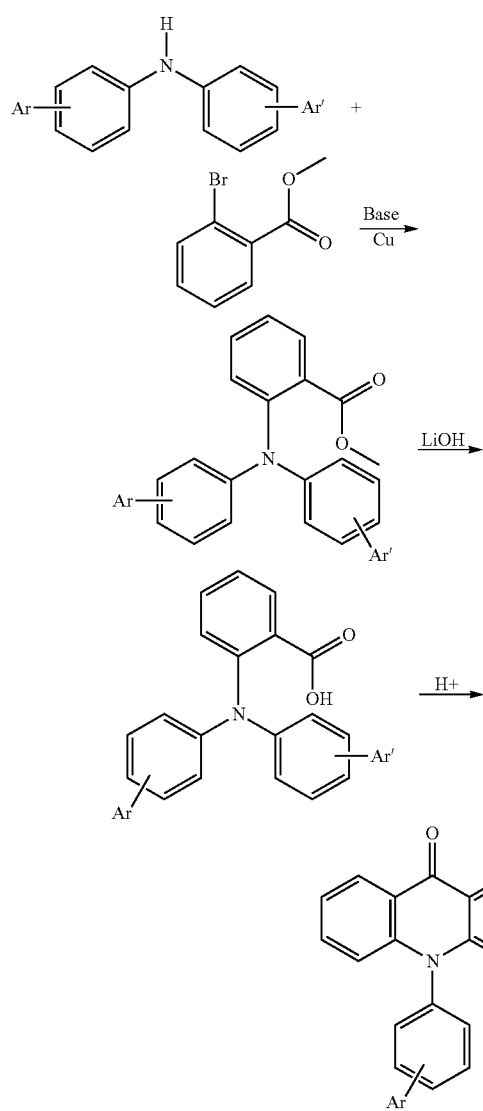

Ar, Ar': aromatic or heteroaromatic ring system

The symmetrically substituted or asymmetrically substituted acridinone derivatives are reacted with appropriately substituted diphenylamines to give spirobisacridines (Scheme 3). The reaction which results in the formation of the spiro unit may be followed by Suzuki coupling reactions for the introduction of substituents onto the aromatic rings and/or Buchwald coupling reactions for the introduction of substituents on the nitrogen atom of the spirobisacridine.

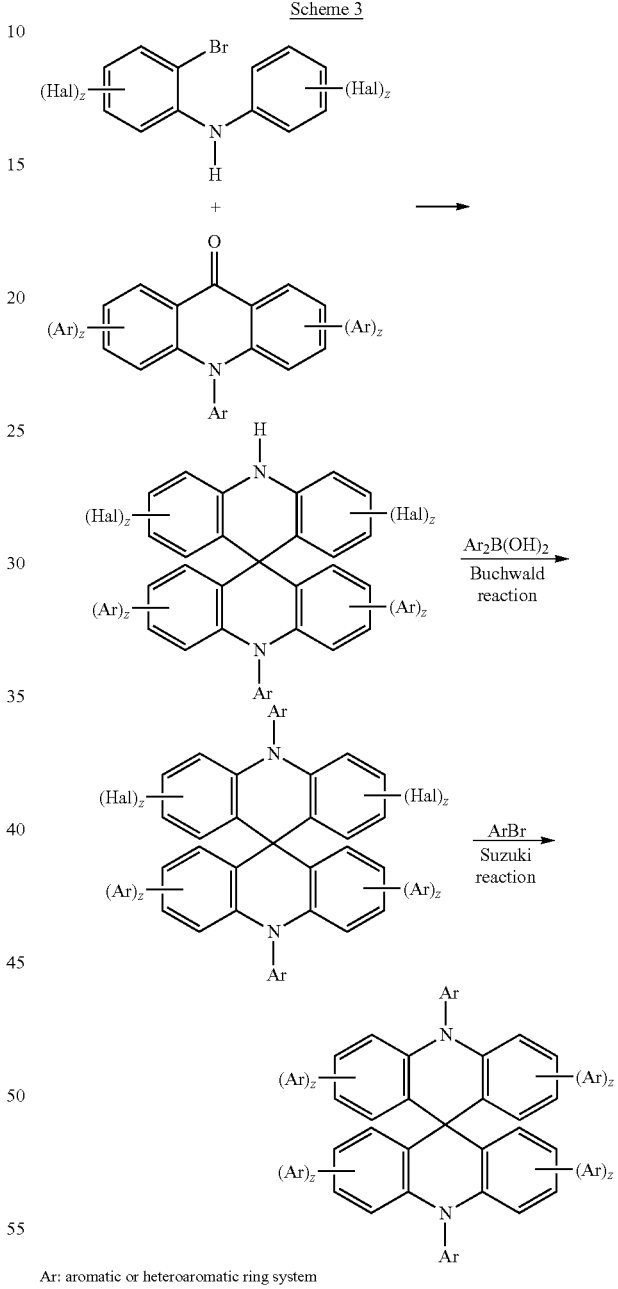

Ar: aromatic or heteroaromatic ring system
Hal: halogen atom or other reactive group
z: 0, 1, 2, 3, 4, preferably 0 or 1

The synthesis processes described are merely preferred processes. Alternative processes are possible, on which the person skilled in the art can fall back if necessary in the context of his general expert knowledge.

The present invention relates to a process for the preparation of compounds of the formula (I), characterised in that it comprises the following steps:

1) reaction of a halogen-substituted diphenylamine derivative with an acridinone derivative in the presence of an organometallic compound;
2) ring-closure reaction of the intermediate formed in 1) to give a spirobisacridine derivative;
3) introduction of an aryl or heteroaryl group on a free nitrogen atom of the spirobisacridine derivative by means of Buchwald coupling.

Step 2) is preferably carried out after step 1), and step 3) is preferably carried out after step 2). Furthermore, derivatisation and coupling reactions, for example Suzuki couplings, preferably follow step 3). It is again furthermore preferred that the organometallic compound in step 1) is an organo-lithium base, particularly preferably n-butyllithium. It is furthermore preferred that a nucleophilic addition reaction onto the carbonyl group, in which a tertiary alcohol forms, is carried out in step 1).

The compounds described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I), where the bond(s) to the polymer, oligomer or dendrimer may be localised at any desired positions In formula (I) which are substituted by $R^1$ or $R^2$. Depending on the linking of the compound of the formula (I) the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) may be linked via a trivalent or polyvalent group, for example via a trivalent or polyvalent aromatic or heteroaromatic group, to form a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers and oligomers according to the invention are generally prepared by polymerisation of one or more types of monomer, at least one monomer of which results in recurring units of the formula ((I) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol mono-butyl ether, tripropylene glycol dimethyl ether, tetraethylene glycol dimethyl ether, 2-isopropylnaphthalene, pentylbenzene, hexylbenzene, heptyl-benzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (OLEDs). Depending on the substitution, the compounds are employed in different functions and layers.

The invention therefore furthermore relates to the use of the compound of the formula (I) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates, as already indicated above, to an electronic device comprising at least one compound of the formula (I). The electronic device here is preferably selected from the devices mentioned above.

It is particularly preferably an organic electroluminescent device (OLED) comprising anode, cathode and at least one emitting layer, characterised in that at least one organic layer, which may be an emitting layer, a hole-transport layer or another layer, comprises at least one compound of the formula (I).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, inter-layers, charge-generation layers (IDMC 2003, Taiwan; Session 21 OLED (5), T. Matsumoto, T. Nakada, J. Endo, K. Mori, N. Kawamura, A. Yokol, J. Kido, *Multiphoton Organic EL Device Having Charge Generation Layer*) and/or organic or inorganic p/n junctions.

The sequence of the layers of the organic electroluminescent device comprising the compound of the formula (I) is preferably the following: anode/hole-injection layer/hole-transport layer/optionally further hole-transport layer/optionally electron-blocking layer/emitting layer/electron-transport layer/electron-injection layer/cathode.

However, not all the said layers have to be present, and further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). The compounds according to the invention are preferably present in the hole-transport layer, hole-injection layer or the electron-blocking layer.

It is preferred in accordance with the invention for the compound of the formula (I) to be employed in an electronic device comprising one or more phosphorescent emitting compounds. The compound may be present in various layers here, preferably in a hole-transport layer, an electron-blocking layer, a hole-injection layer or in an emitting layer.

The term phosphorescent emitting compounds typically encompasses compounds in which the light emission takes place through a spin-forbid-den transition, for example a transition from an excited triplet state or a state having a higher spin quantum number, for example a quintet state.

Suitable phosphorescent emitting compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitting compounds used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent emitting compounds.

Examples of the emitting compounds described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able, without inventive step, to employ further phosphorescent complexes in combination with the compounds of the formula (I) in organic electroluminescent devices. Further examples are shown in a following table.

However, the compound of the formula (I) can also be employed in accordance with the invention in an electronic device comprising one or more fluorescent emitting compounds.

In a preferred embodiment of the invention, the compounds of the formula (I) are employed as hole-transport material. The compounds are then preferably present in a hole-transport layer, an electron-blocking layer or a hole-injection layer.

A hole-transport layer in accordance with the present application is a layer having a hole-transporting function which is located between anode and emitting layer.

Hole-injection layers and electron-blocking layers in the sense of the present invention are taken to be specific embodiments of hole-transport layers. In the case of a plurality of hole-transport layers between anode and emitting layer, a hole-Injection layer is a hole-transport layer which is directly adjacent to the anode or is only separated therefrom by a single coating of the anode. In the case of a plurality of hole-transport layers between anode and emitting layer, an electron-blocking layer is the hole-transport layer which is directly adjacent to the emitting layer on the anode side.

If the compound of the formula (I) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) then additionally comprises one or more p-dopants. In accordance with the present invention, the p-dopants employed are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

Particularly preferred p-dopants are quinodimethane compounds, aza-indenofluorenediones, azaphenalenes, azatriphenyenes, $I_2$, metal halides, preferably transition-metal halides, metal oxides, preferably metal oxides containing at least one transition metal or a metal from the 3rd main group, and transition-metal complexes, preferably complexes of Cu, Co, Ni, Pd and Pt with ligands containing at least one oxygen atom as bonding site. The dopants are furthermore preferably transition-metal oxides, preferably oxides of rhenium, molybdenum and tungsten, particularly preferably $Re_2O_7$, $MoO_3$, $WO_3$ and $ReO_3$.

The p-dopants are preferably substantially uniformly distributed in the p-doped layers. This can be achieved, for example, by co-evaporation of the p-dopant and the hole-transport material matrix.

Preferred p-dopants are, in particular, the following compounds:

(D-1)
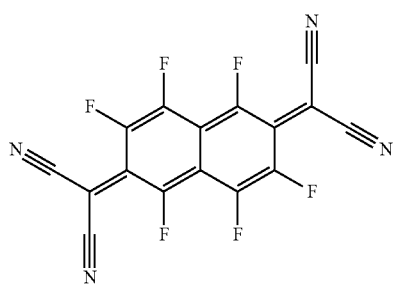

(D-2)
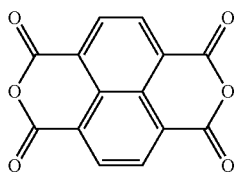

(D-3)
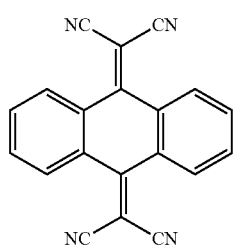

(D-4)
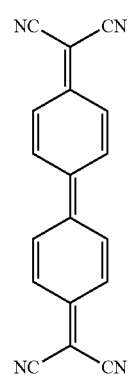

(D-5)
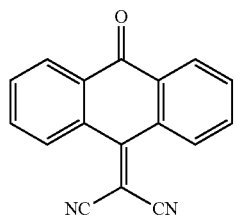

(D-6)
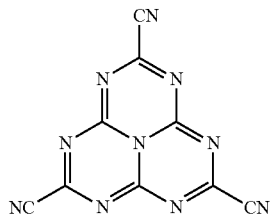

(D-7)
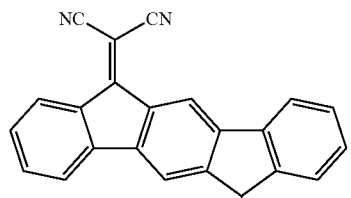

(D-8)
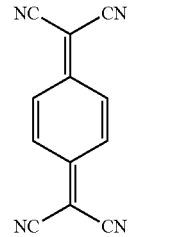

(D-9)
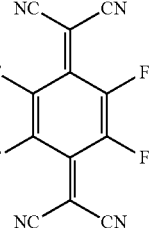

-continued

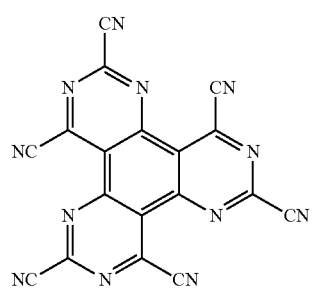
(D-10)

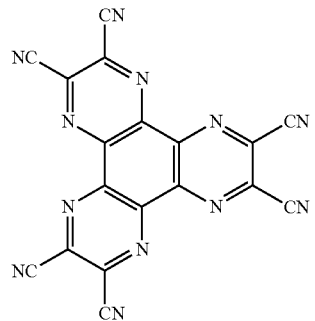
(D-11)

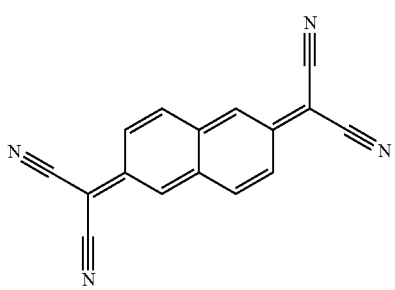
(D-12)

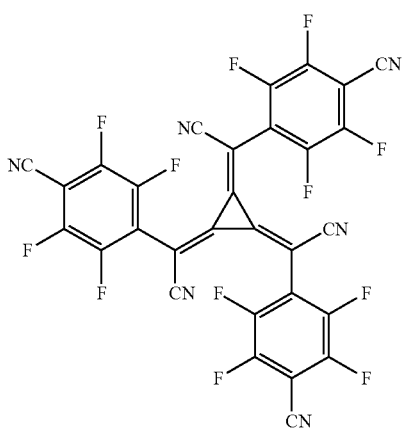
(D-13)

In a further preferred embodiment of the invention, the compound of the formula (I) is used as hole-transport material in combination with a hexaazatriphenylene derivative, as described in US 2007/0092755. The hexaazatriphenylene derivative here is particularly preferably employed in a separate layer.

In a further embodiment of the present invention, the compound of the formula (I) is employed in an emitting layer as matrix material in combination with one or more emitting compounds, preferably phosphorescent emitting compounds.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the emitting compound is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of emitting compounds. In this case too, the emitting compounds are generally the compounds whose proportion in the system is the smaller and the matrix materials are the compounds whose proportion in the system is the greater. In individual cases, however, the proportion of an individual matrix material in the system may be smaller than the proportion of an individual emitting compound.

The compounds of the formula (I) are preferably used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. The compound of the formula (I) here is preferably the matrix material having hole-transporting properties. However, the desired electron-transporting and hole-transporting properties of the mixed-matrix components may also be combined principally or completely in a single mixed-matrix component, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more emitting compounds, preferably one or more phosphorescent emitting compounds. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent emitting compounds indicated below or the preferred matrix materials for fluorescent emitting compounds, depending on what type of emitting compound is employed in the mixed-matrix system.

Preferred phosphorescent emitting compounds for use in mixed-matrix systems are shown in a table below.

Preferred embodiments of the various functional materials of the electronic device are shown below.

Preferred phosphorescent emitting compounds are the above-mentioned compounds and the compounds shown in the following table:

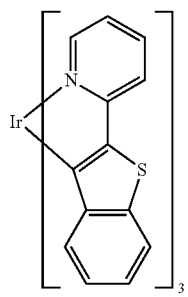
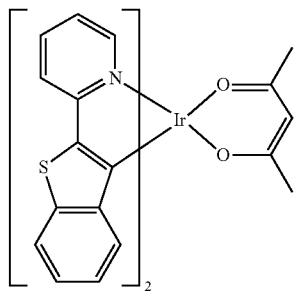
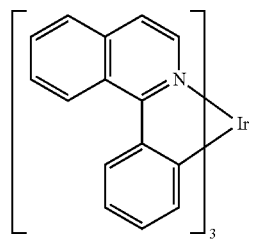
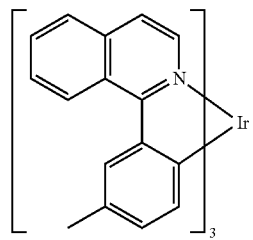
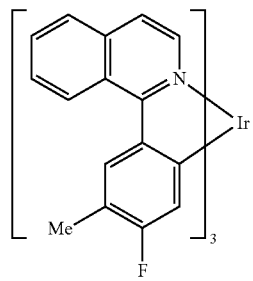
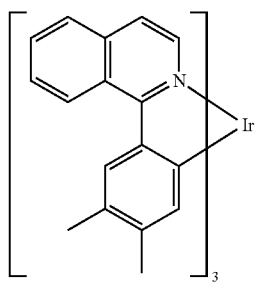
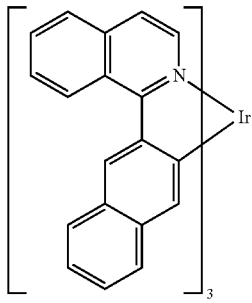
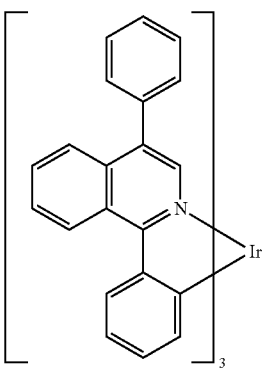
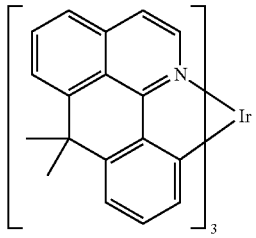
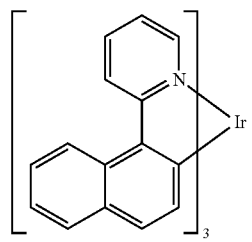
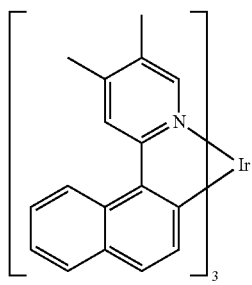

95
-continued
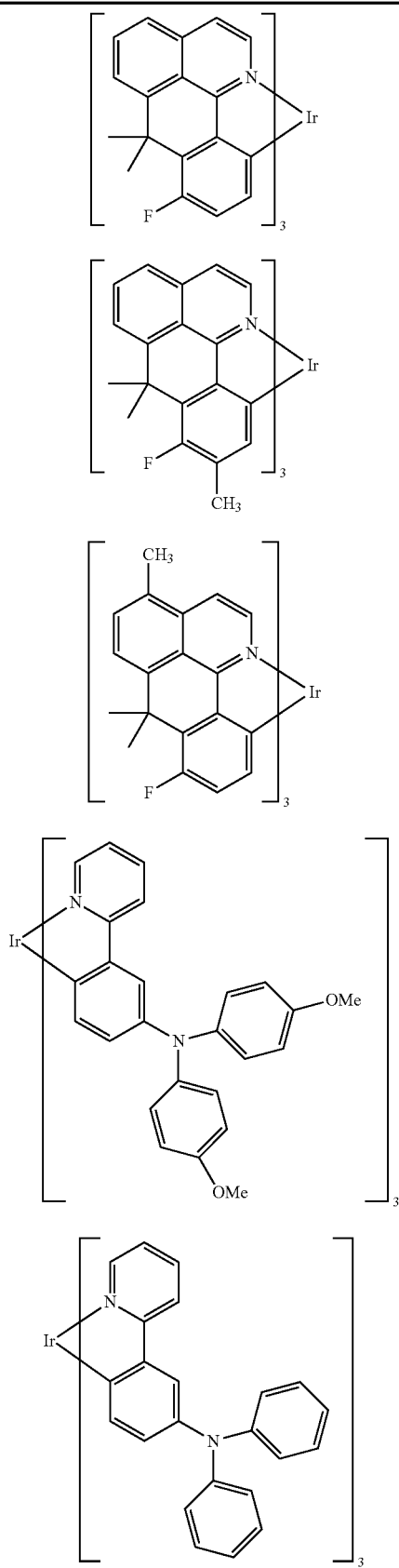
96
-continued
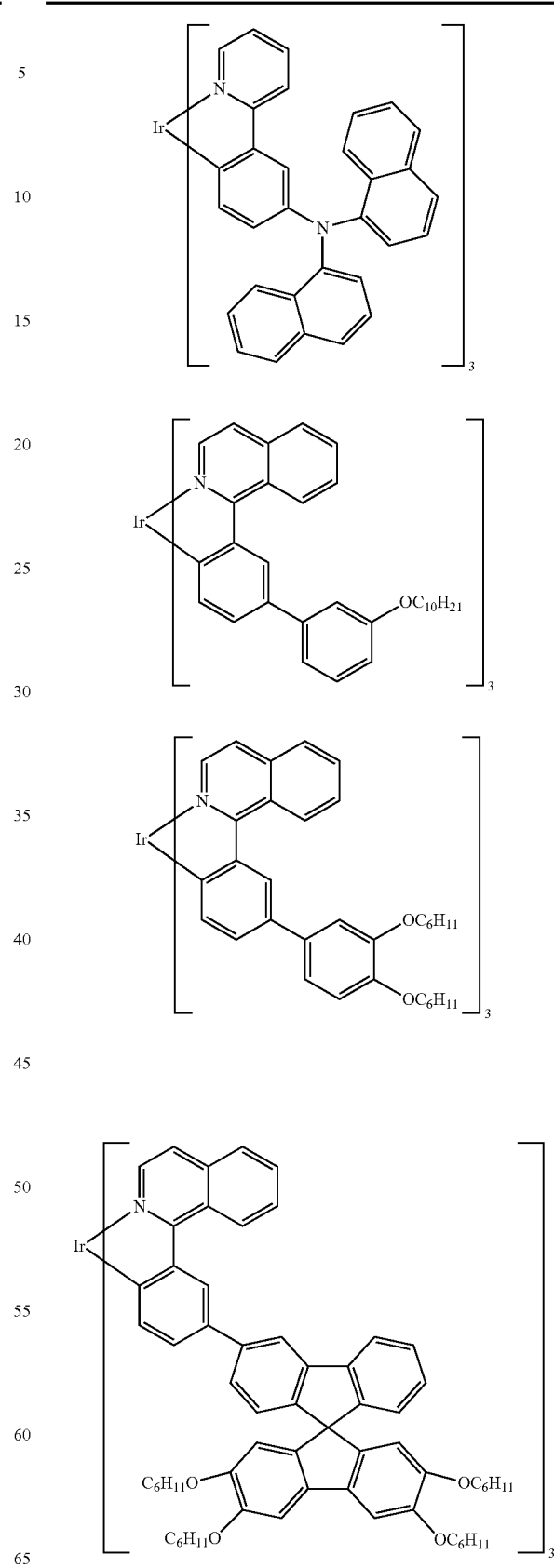

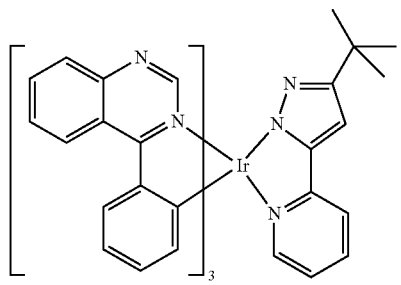
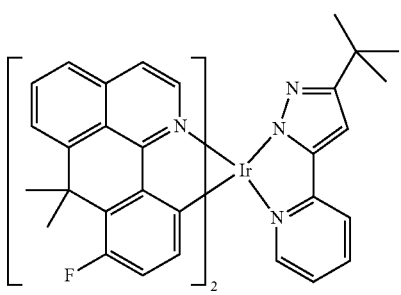
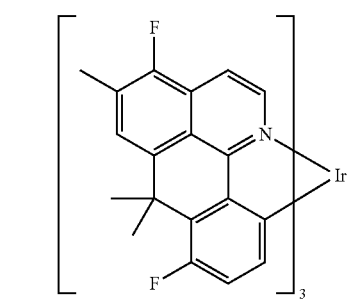
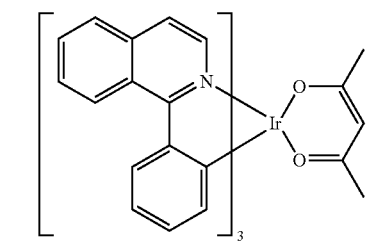
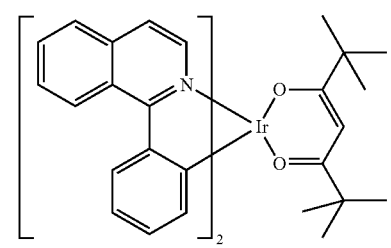
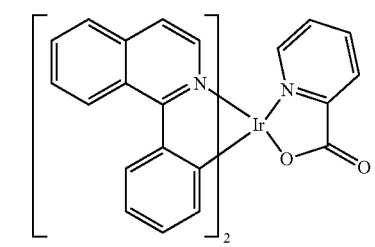
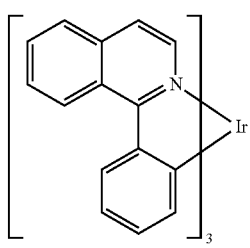
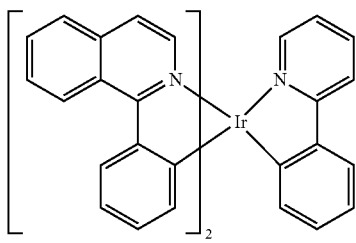
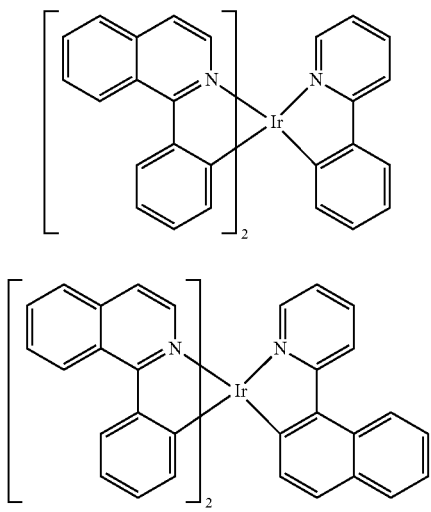
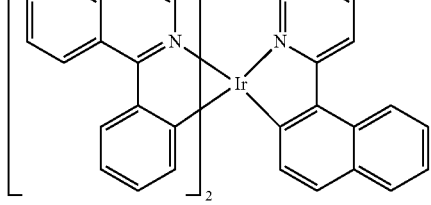
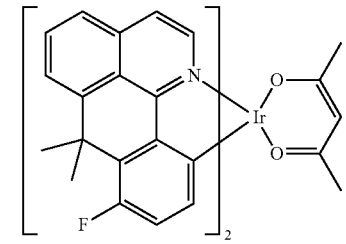
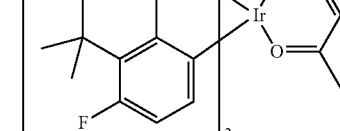
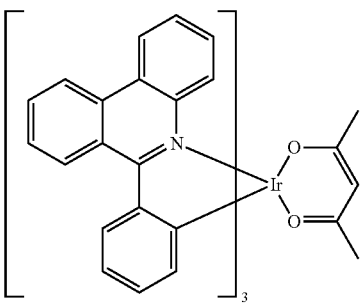
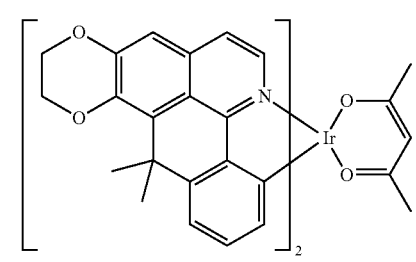

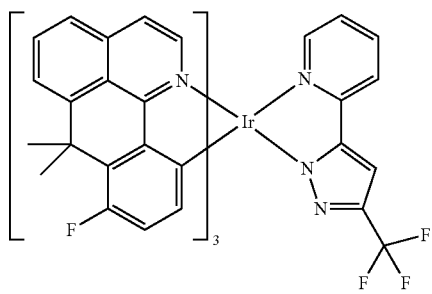
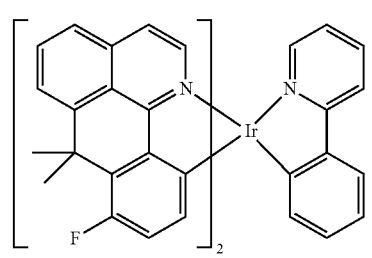
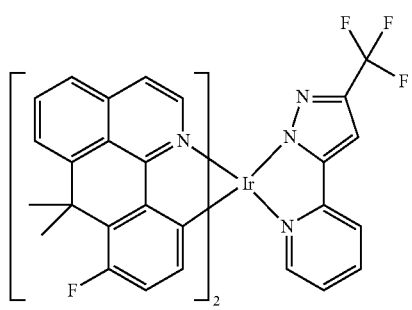
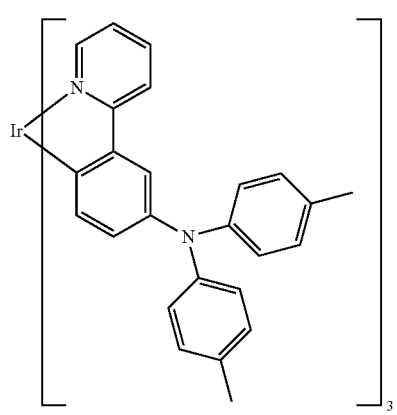
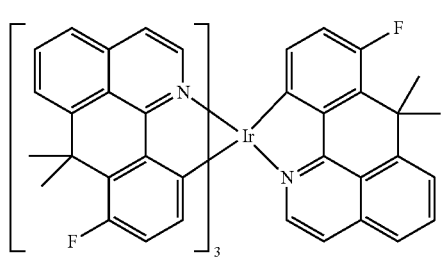
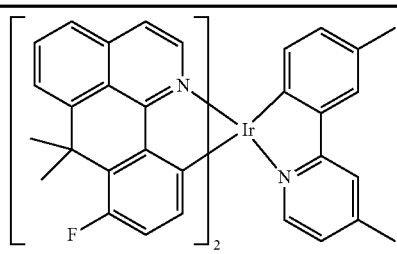
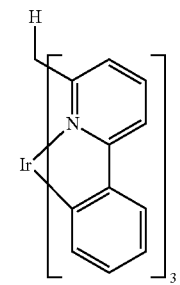
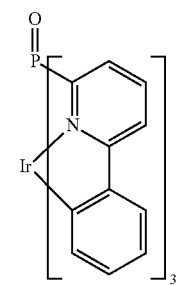
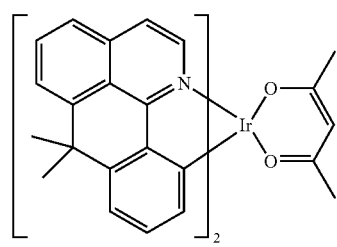
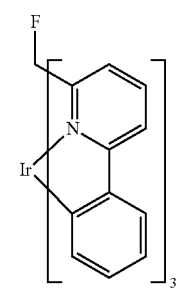
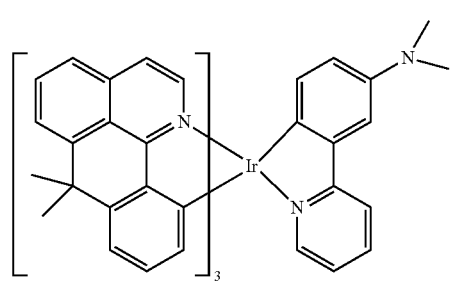

101
-continued
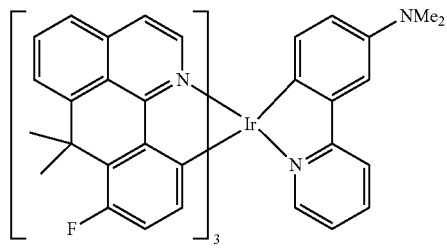
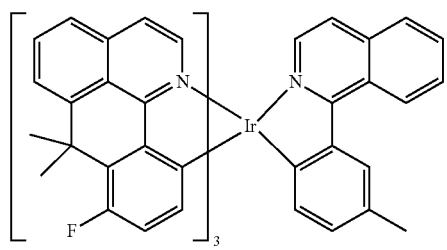
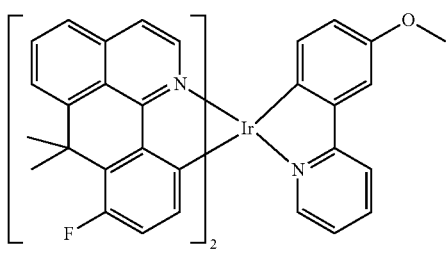
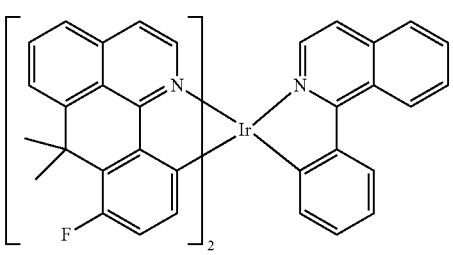
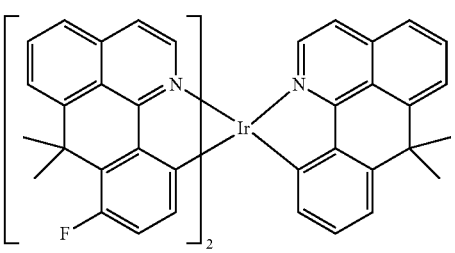
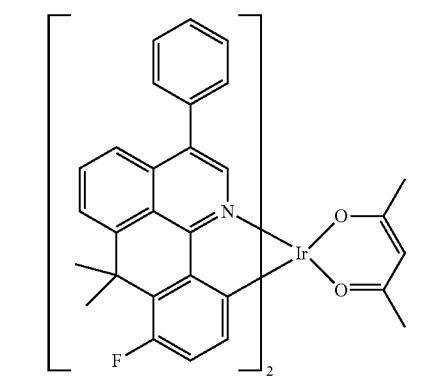
102
-continued
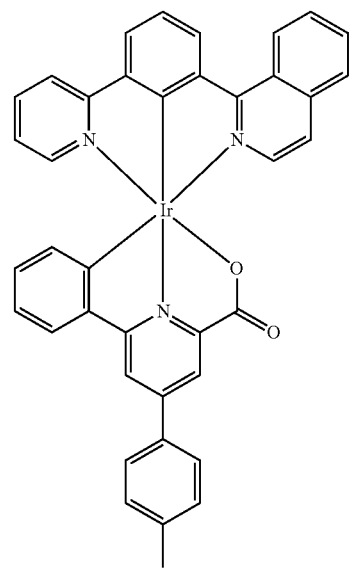
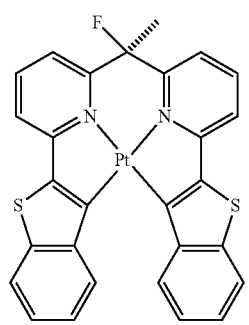
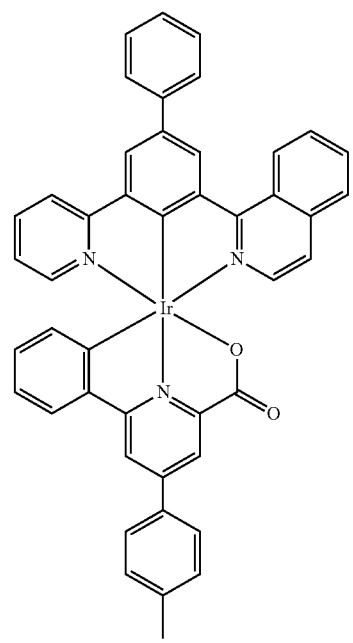

103
-continued
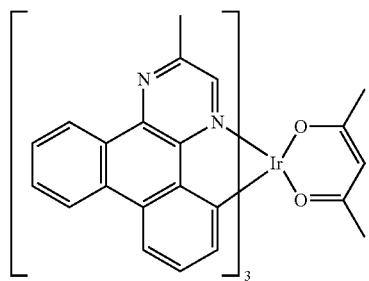
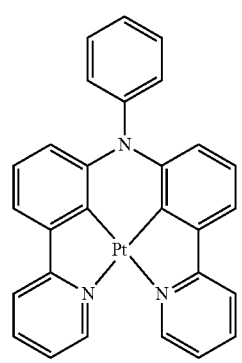
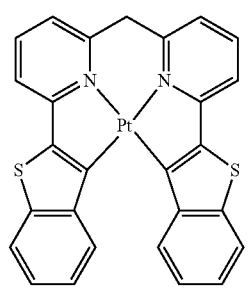
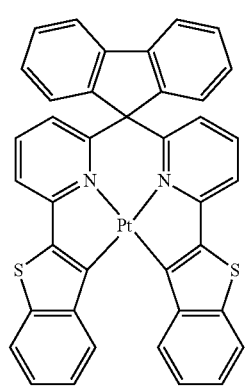
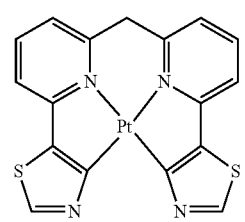
104
-continued
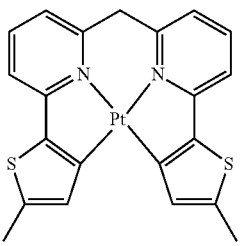
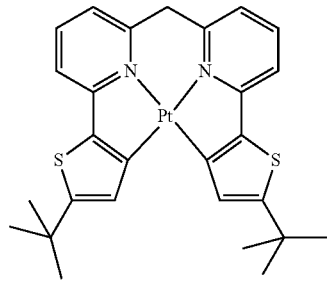
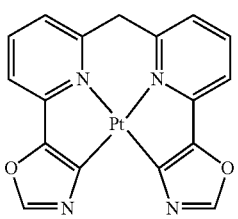
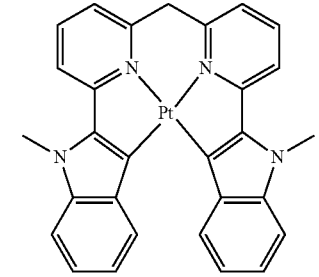
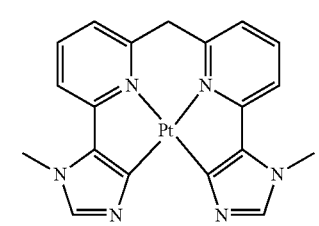

| 105 -continued | 106 -continued |
|---|---|
| 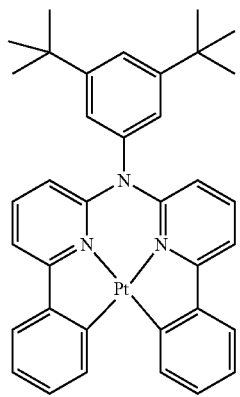 | 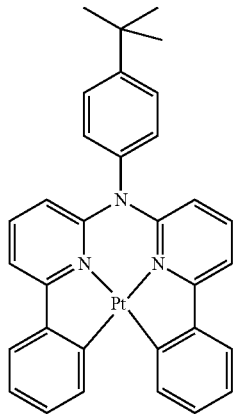 |
| 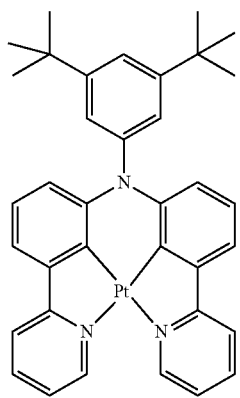 | 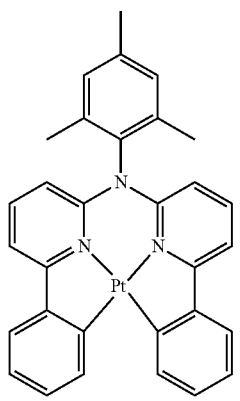 |
| 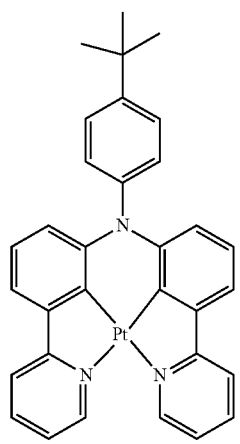 | 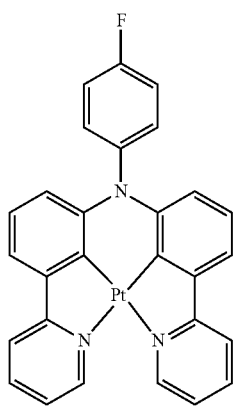 |
| 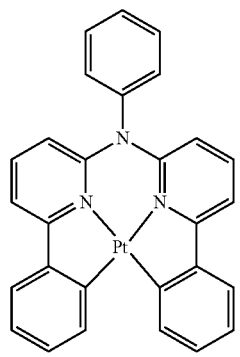 | 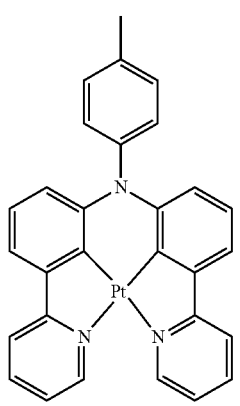 |

| 107 -continued | 108 -continued |
|---|---|
| 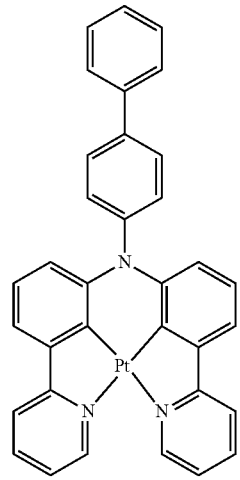 | 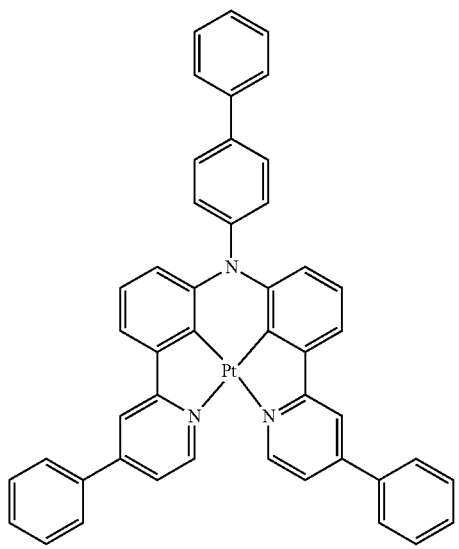 |
| 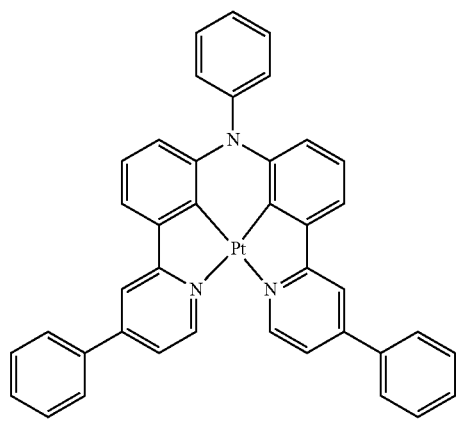 | 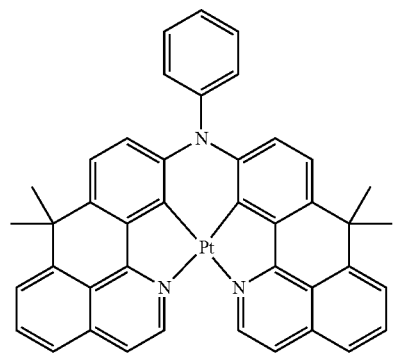 |
| 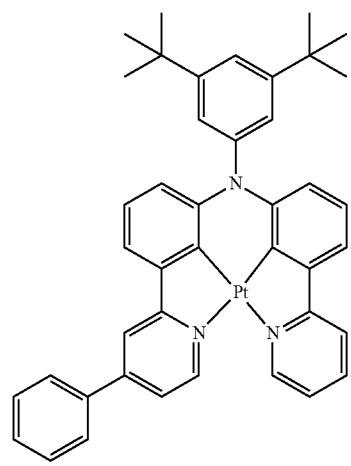 | 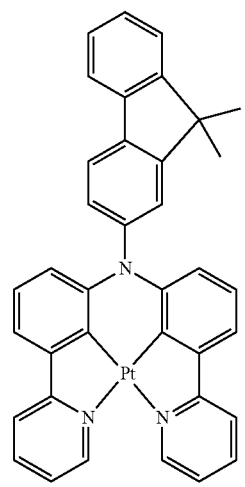 |

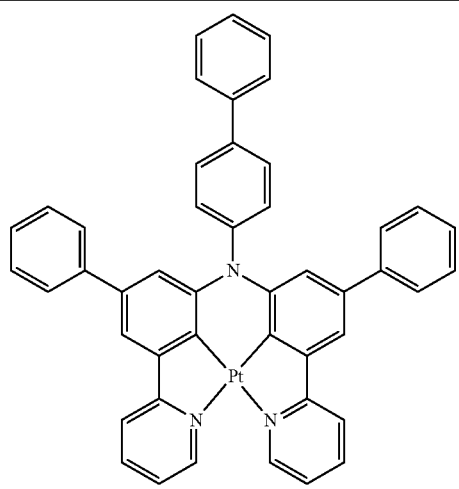
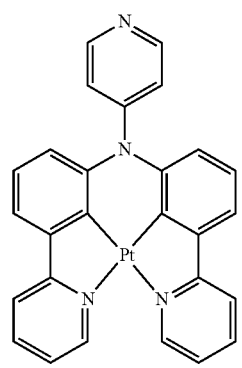
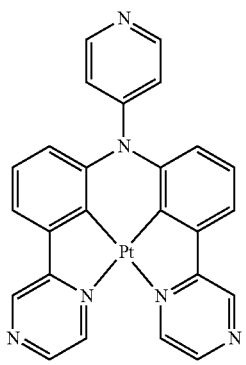
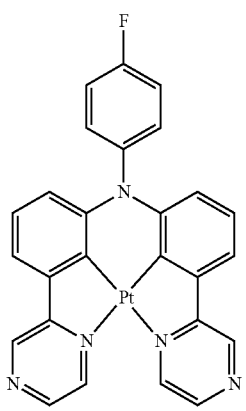
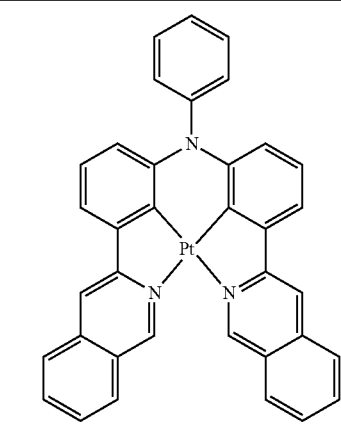
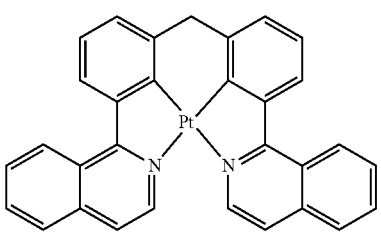
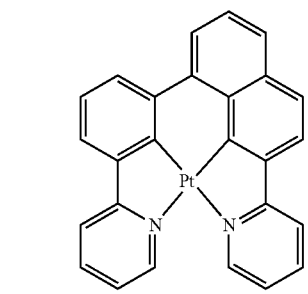
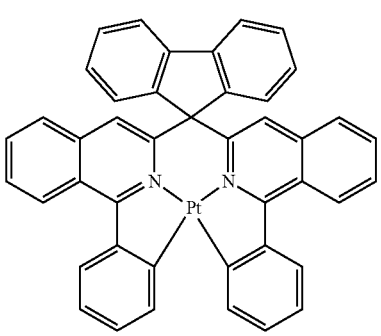
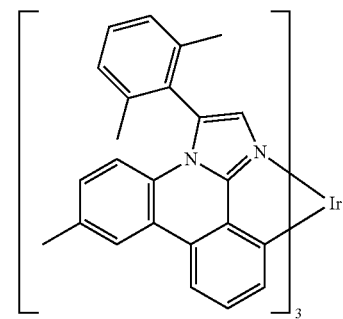

111
-continued
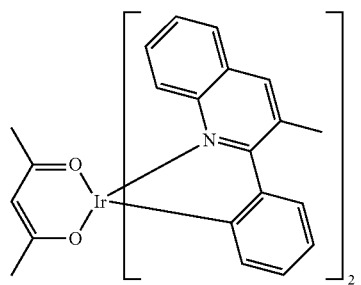
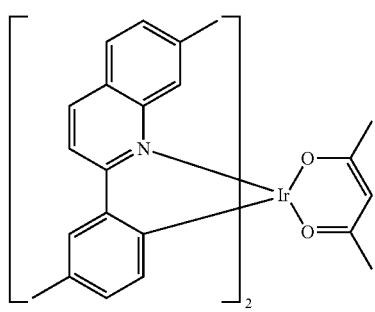
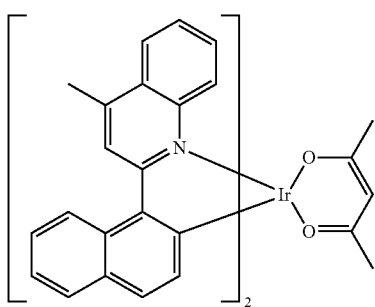
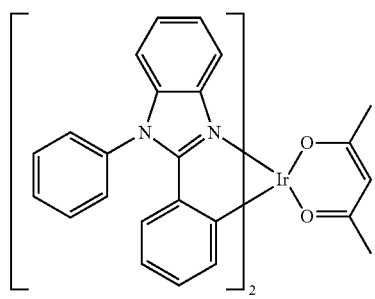
112
-continued
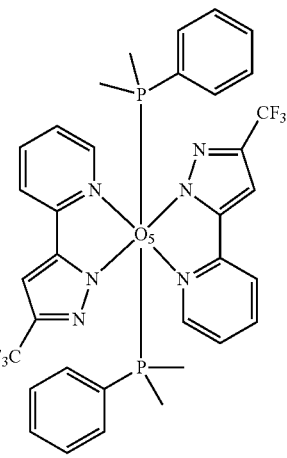
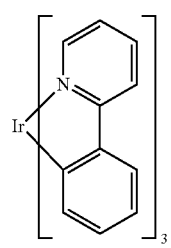
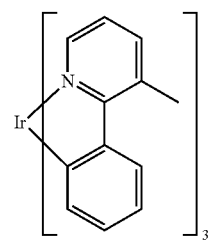
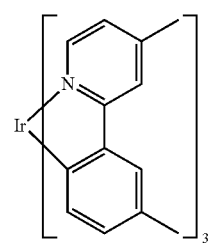
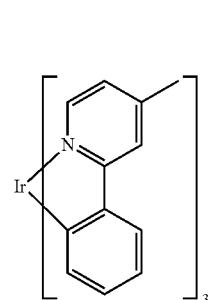

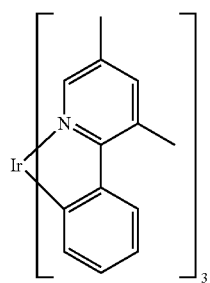
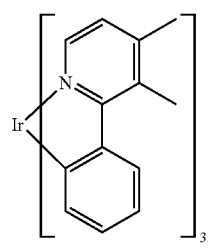
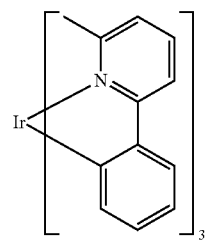
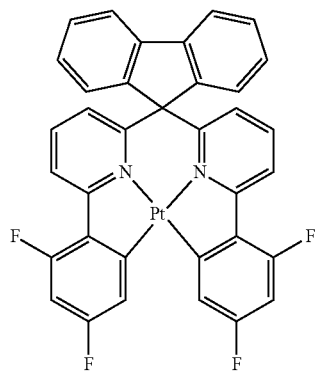
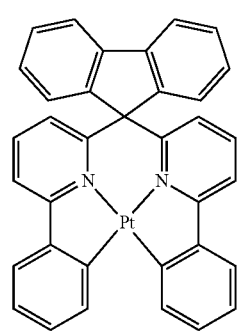
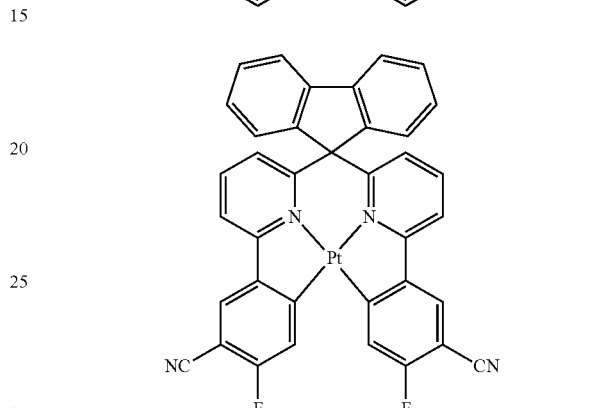
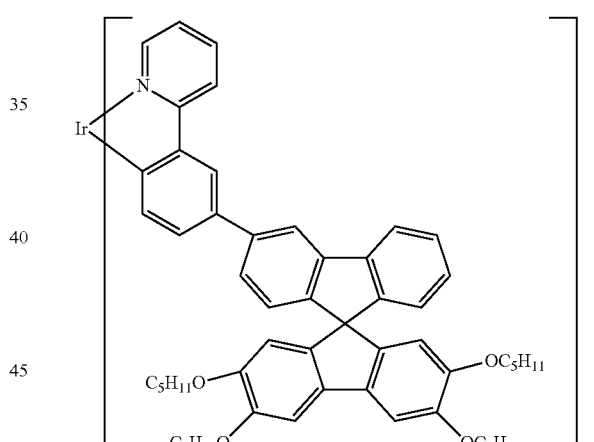
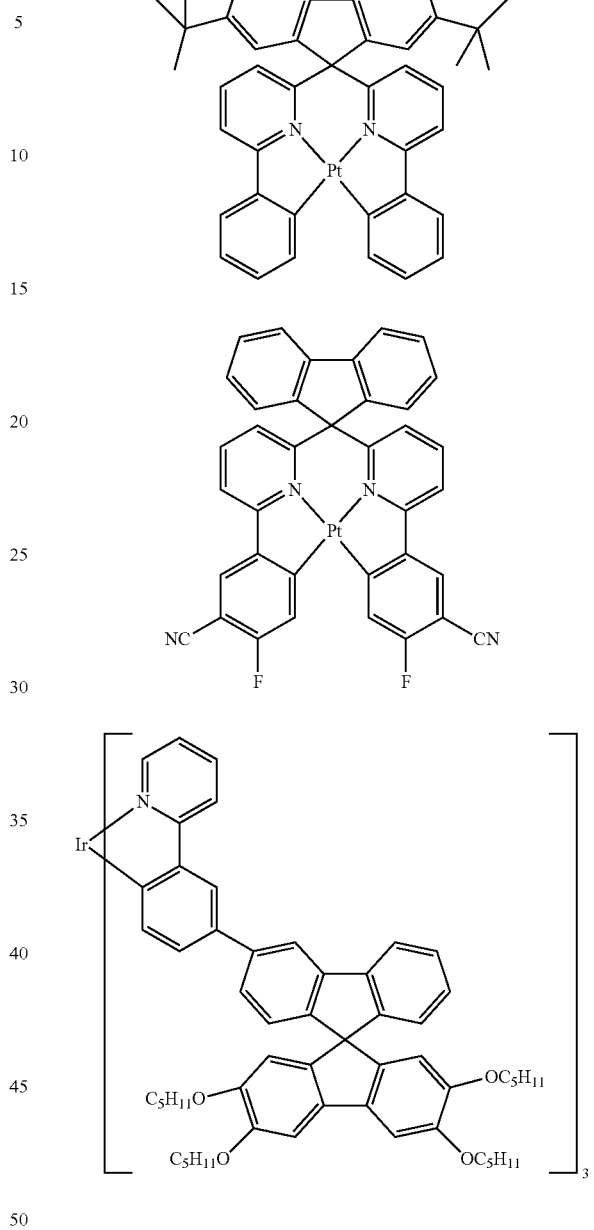
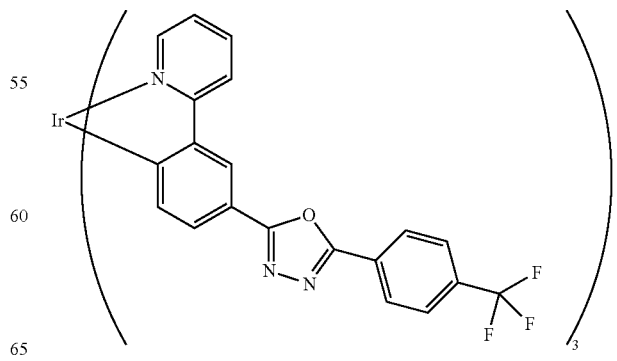

115
-continued
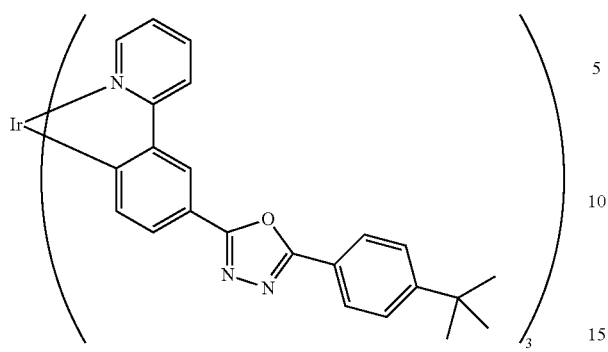
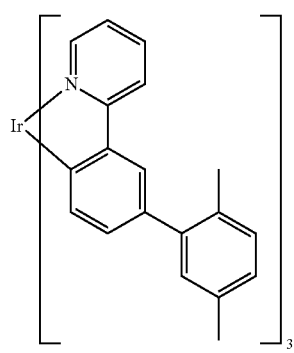
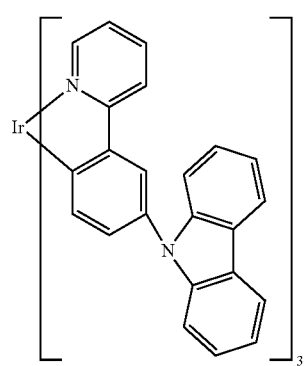
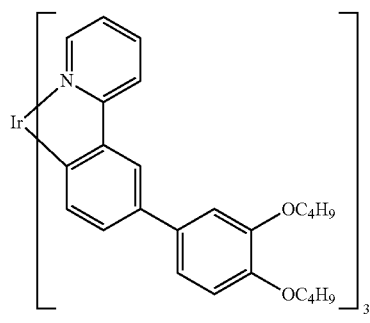
116
-continued
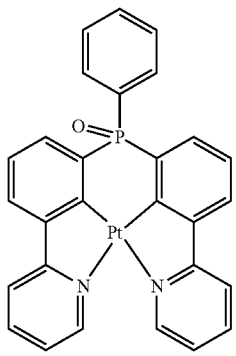
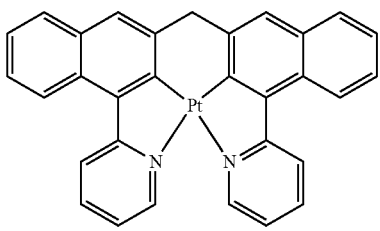
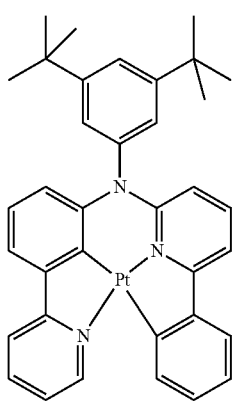
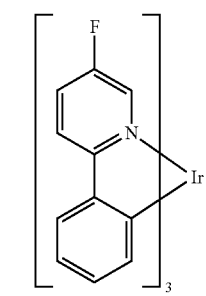
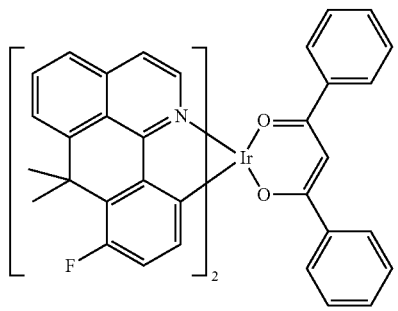

| 117 -continued | 118 -continued |
|---|---|
| 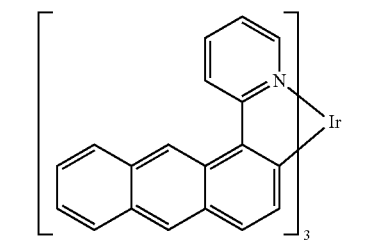 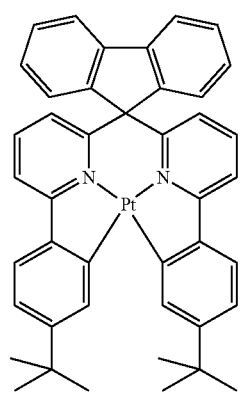 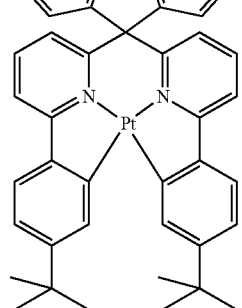 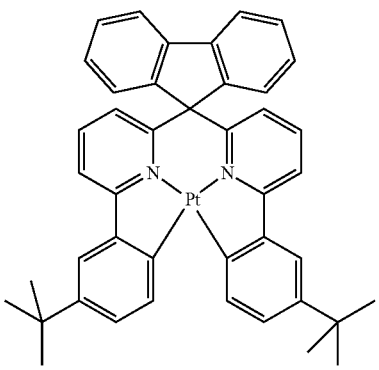 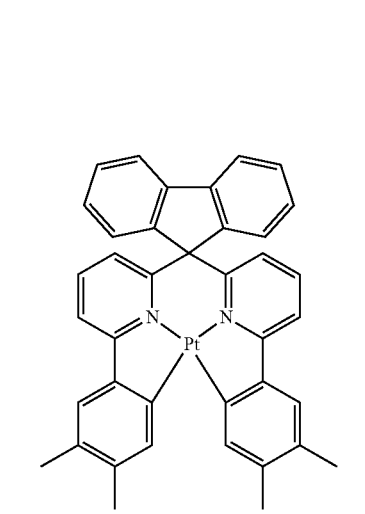 | 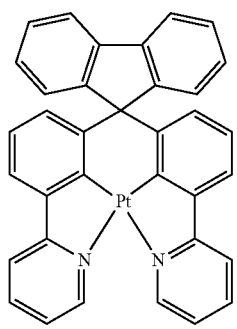 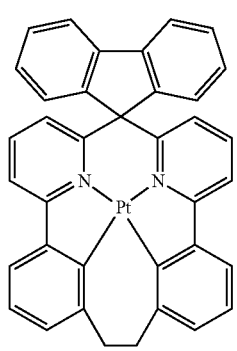 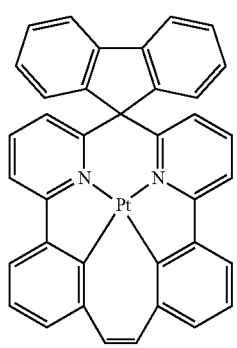 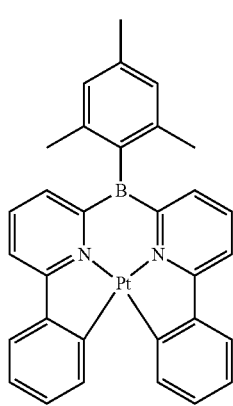 |

119
-continued
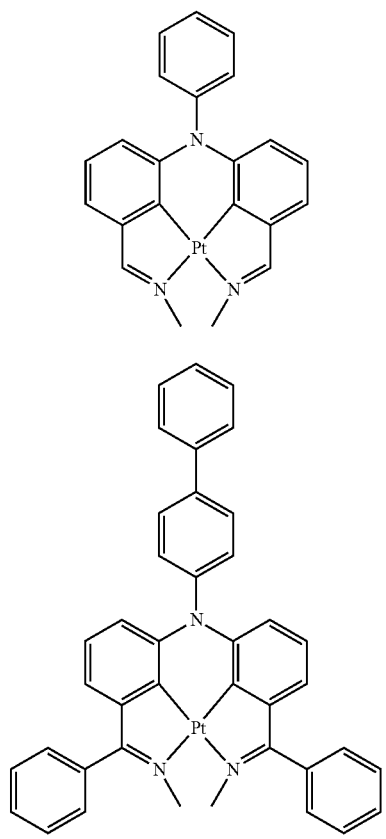
120
-continued
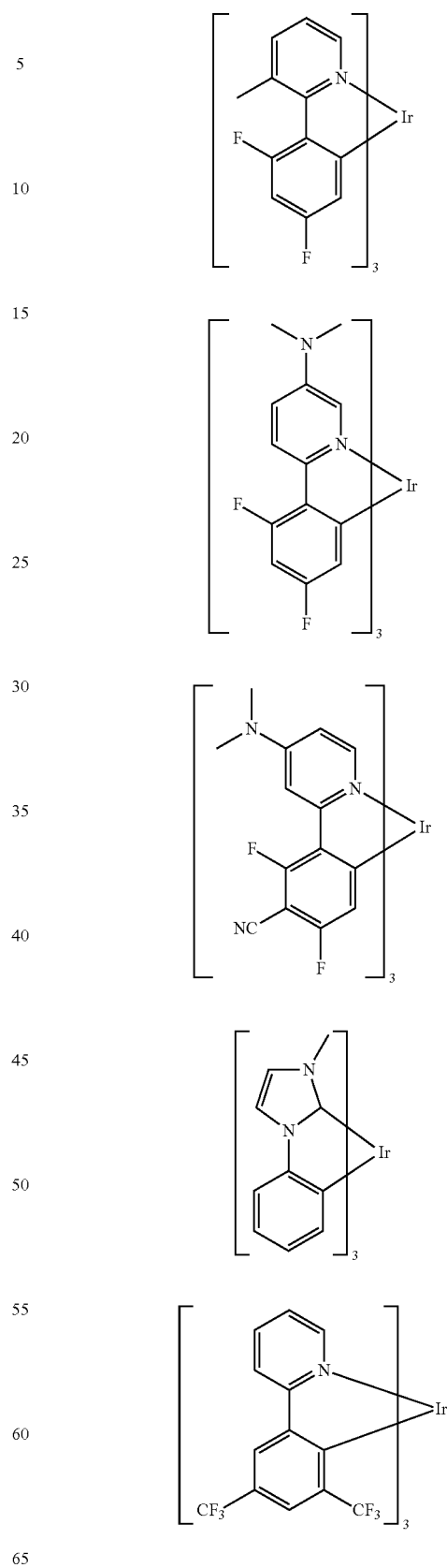

| 121 -continued | 122 -continued |
|---|---|
| 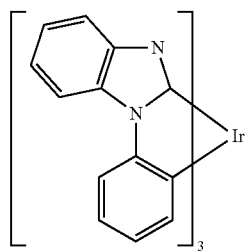 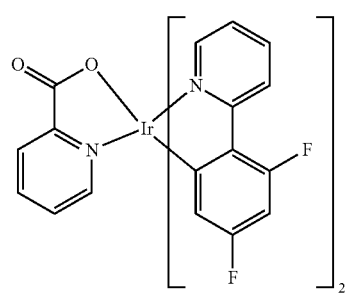 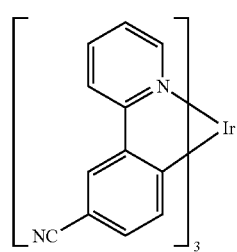 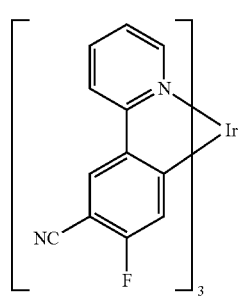 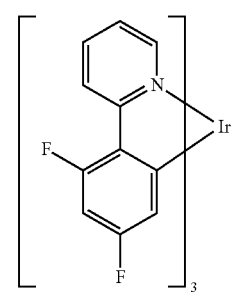 | 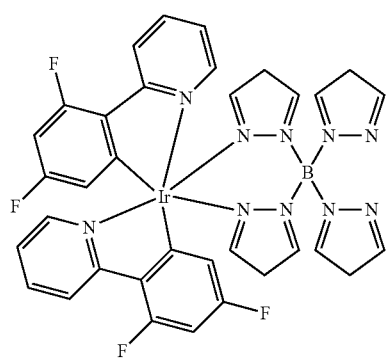 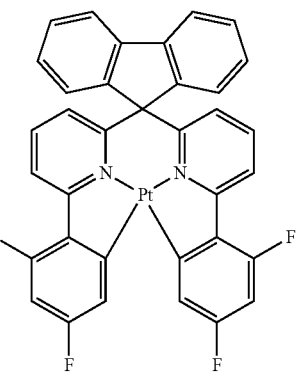 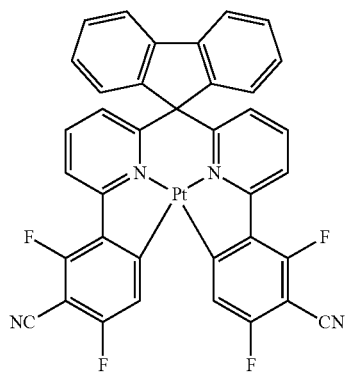 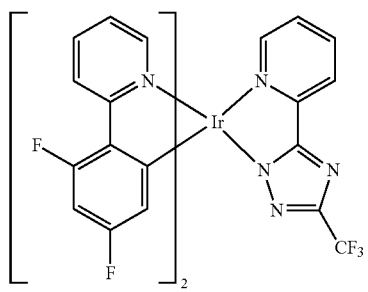 |

-continued
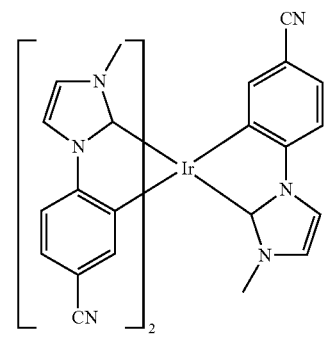
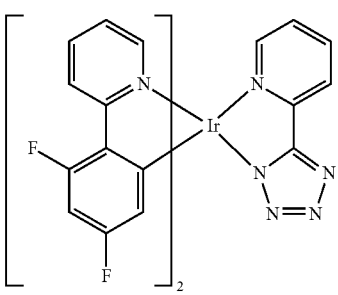
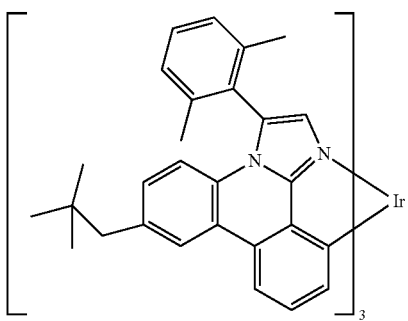
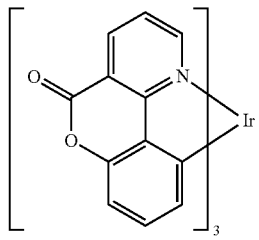
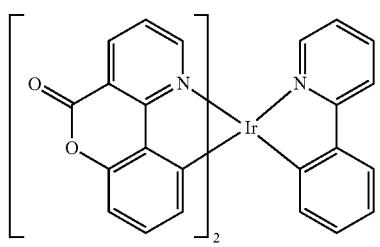
-continued
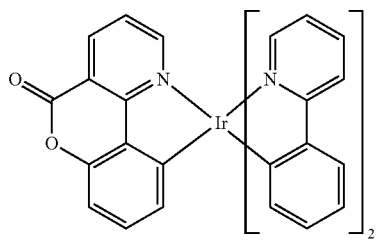
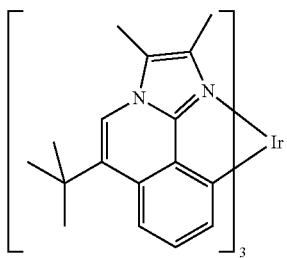
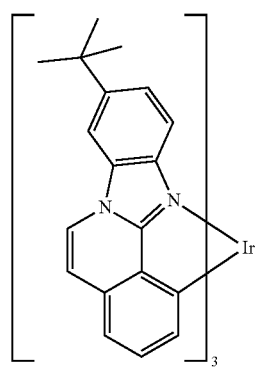
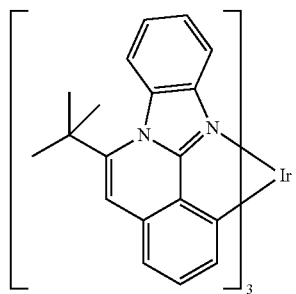
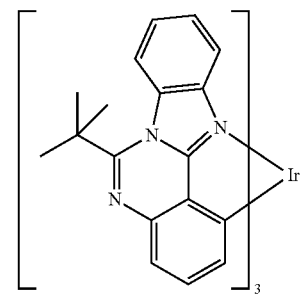

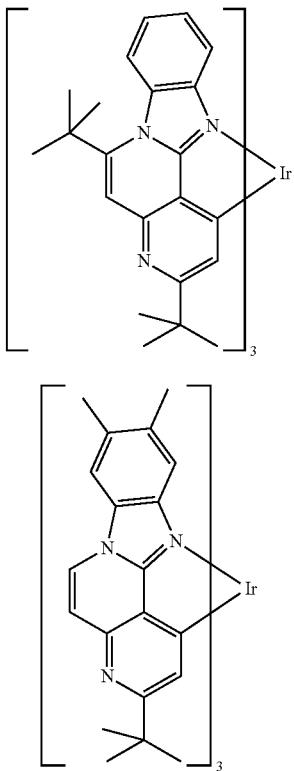

Preferred fluorescent emitting compounds, besides the compounds of the formula (I), are selected from the class of the arylamines. An arylamine or aromatic amine in the sense of the present invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitting compounds are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrene-arylamines disclosed in WO 2012/048780 and those in WO 2013/185871. Preference is likewise given to the benzoindenofluorenamines disclosed in WO 2014/037077, the benzofluorenamines disclosed in WO 2014/106522 and the benzoindenofluorenes disclosed in WO 2014/111269.

Suitable matrix materials, preferably for fluorescent emitting compounds, are materials from various classes of substance. Preferred matrix materials are selected from the classes of the oligoarylenes (for example 2,2',7,7'-tetraphenylspirobifluorene in accordance with EP 676461 or dinaphthyl-anthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another. Preference is furthermore given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154 and the pyrene compounds disclosed in EP 1749809, EP 1905754 and US 2012/0187826.

Preferred matrix materials for phosphorescent emitting compounds are, besides the compounds of the formula (I), aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, Indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Suitable charge-transport materials, as can be used in the hole-injection or hole-transport layer or electron-blocking layer or in the electron-transport layer of the electronic device according to the invention, besides the compounds of the formula (I), are, for example, the compounds disclosed in Y. Shirota et al., Chem. Rev. 2007, 107(4), 953-1010, or other materials as are employed in these layers in accordance with the prior art.

The OLED according to the invention preferably comprises two or more different hole-transporting layers. The compound of the formula (I) here can be employed in one or in several or in all hole-transporting layers. In accordance with a preferred embodiment, the compound of the formula (I) is employed in precisely one hole-transporting layer, and other compounds, preferably aromatic amine compounds, are employed in the other hole-transporting layers present.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

The cathode of the electronic device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers. Furthermore, the anode may also consist of a plurality of layers, for example of an inner layer of ITO and an outer layer of a metal oxide, preferably tungsten oxide, molybdenum oxide or vanadium oxide.

The device is appropriately (depending on the application) structured, pro-vided with contacts and finally sealed in order to exclude harmful effects of water and air.

In a preferred embodiment, the electronic device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an electronic device, characterised in that one or more layers are applied by means of the OVPD (organic vapour phase deposition) process or with the aid of carrier-gas sublimation, in which the materials are applied at a pressure of between $10^{-6}$ mbar and 1 bar. A special case of this process is the OVJP (organic vapour jet printing) process, in which the materials are applied directly through a nozzle and are thus structured (for example M. S. Arnold et al., Appl. Phys. Lett. 2008, 92, 053301).

Preference is furthermore given to an electronic device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an electronic device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

WORKING EXAMPLES

A) Synthesis Examples

A-1) Synthesis of Symmetrical Basic Structures
Step 1:

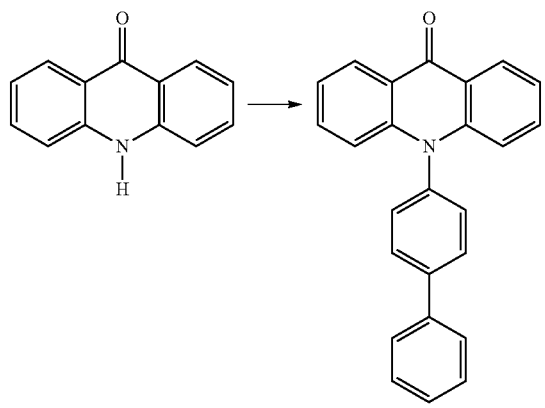 [SMILES: O=c1c2ccccc2[nH]c2ccccc12 ; O=c1c2ccccc2n(-c2ccc(-c3ccccc3)cc2)c2ccccc12]

100 g (0.5 mol) of 10H-acridin-9-one, 140 g (0.6 mol) of 4-bromobiphenyl, 9.6 g (0.05 mol) of CuI, 104.0 g (0.75 mol) of potassium carbonate and 22.0 ml (0.1 mol) of 2,2,6,6-tetramethylheptane-3,5-dione are dissolved in 600 ml of dimethylformamide under a protective atmosphere. The reaction mixture is heated at the boil for 48 h under a protective atmosphere. Water is subsequently added to the mixture. The solid is filtered off with suction, washed with water and ethanol and recrystallised from toluene.

Yield: 167 g (0.48 mol), 96% of theory.

The following compounds can be obtained analogously:
| Starting material 1 | Starting material 2 | Product | Yield |
|---|---|---|---|
| 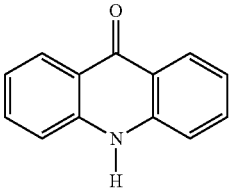 [SMILES: O=c1c2ccccc2[nH]c2ccccc12] | 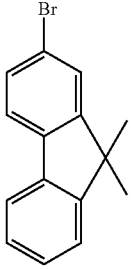 [SMILES: CC1(C)c2ccccc2-c2ccc(Br)cc21] | 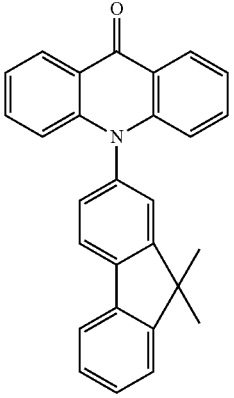 [SMILES: CC1(C)c2ccccc2-c2ccc(-n3c4ccccc4c(=O)c4ccccc43)cc21] | 85% |
| 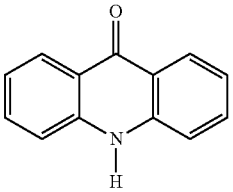 [SMILES: O=c1c2ccccc2[nH]c2ccccc12] | 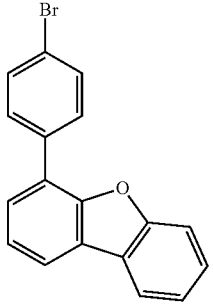 [SMILES: Brc1ccc(-c2cccc3c2oc2ccccc23)cc1] | 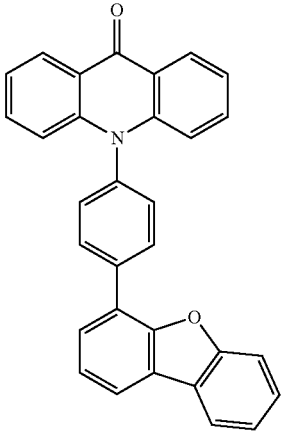 | 89% |
| 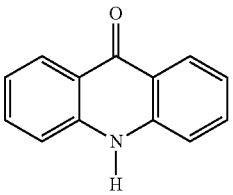 [SMILES: O=c1c2ccccc2[nH]c2ccccc12] | 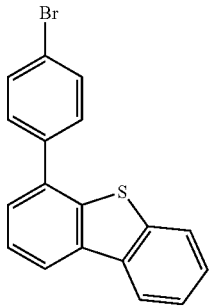 [SMILES: Brc1ccc(-c2cccc3c2sc2ccccc23)cc1] | 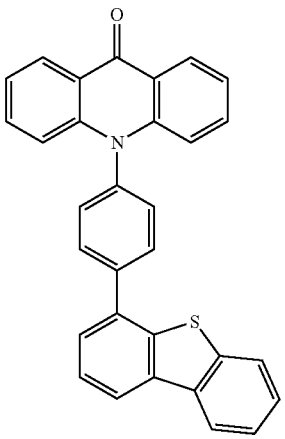 | 91% |

| Starting material 1 | Starting material 2 | Product | Yield |
|---|---|---|---|
| 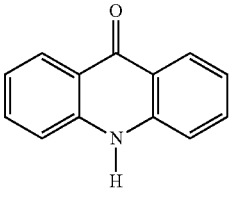 [SMILES: O=c1c2ccccc2[nH]c2ccccc12] | 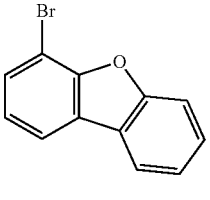 [SMILES: Brc1cccc2c1oc1ccccc12] | 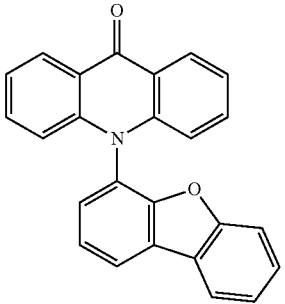 [SMILES: O=c1c2ccccc2n(-c2cccc3c2oc2ccccc23)c2ccccc12] | 81% |
| 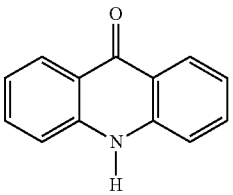 [SMILES: O=c1c2ccccc2[nH]c2ccccc12] | 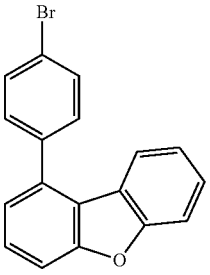 [SMILES: Brc1ccc(-c2cccc3oc4ccccc4c23)cc1] | 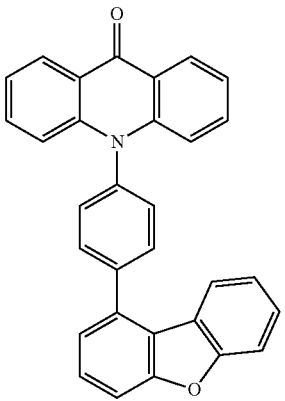 [SMILES: O=c1c2ccccc2n(-c2ccc(-c3cccc4oc5ccccc5c34)cc2)c2ccccc12] | 95% |
| 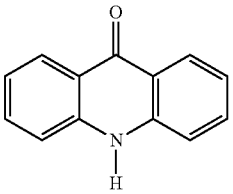 [SMILES: O=c1c2ccccc2[nH]c2ccccc12] | 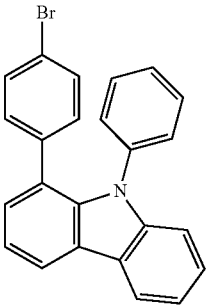 [SMILES: Brc1ccc(-c2cccc3c4ccccc4n(-c4ccccc4)c23)cc1] | 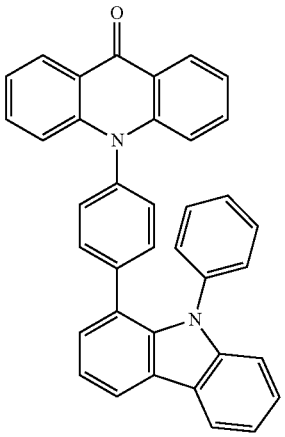 [SMILES: O=c1c2ccccc2n(-c2ccc(-c3cccc4c5ccccc5n(-c5ccccc5)c34)cc2)c2ccccc12] | 90% |

-continued
| Starting material 1 | Starting material 2 | Product | Yield |
|---|---|---|---|
| | | | 85% |
| | | | 97% |
Step 2:
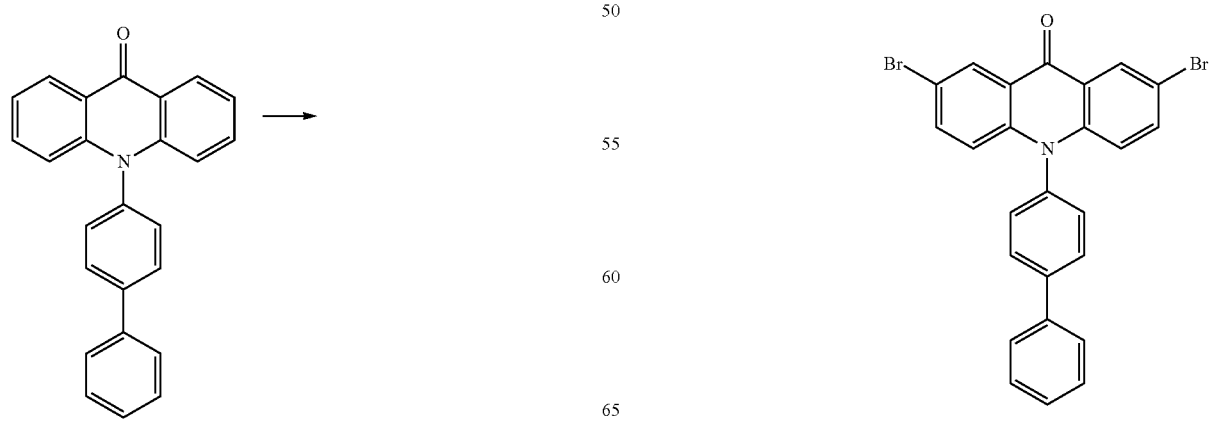
-continued N-Bromosuccinimide (31.05 g, 172.7 mmol) is added in portions to a solution of the dihydroacridone (30.0 g, 86.3 mmol) in DMF (1400 ml) at 0° C. with exclusion of light, and the mixture is stirred overnight at room temperature. Half of the solvent is removed in a rotary evaporator, and 300 ml of ethanol are added to the mixture. The solid is filtered off with suction and recrystallised from DMF. Yield: 42 g, 97% of theory, yellow solid.

| Starting material 1 | Product | Yield |
|---|---|---|
| | | 85% |
| | | 93% |
| | | 91% |

Step 3:

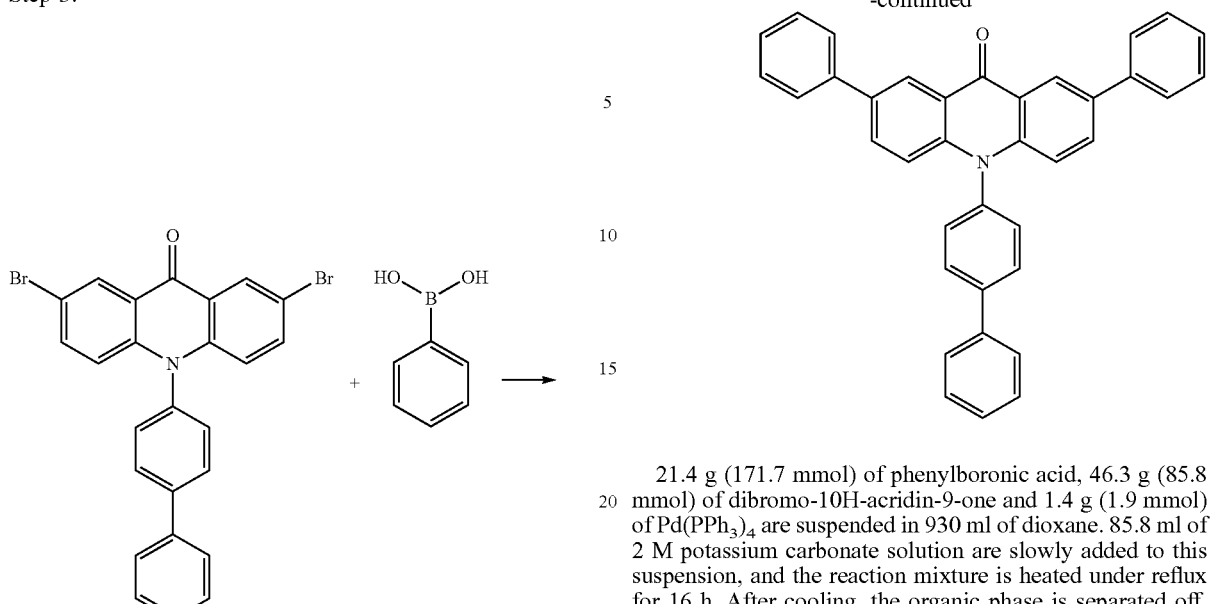

21.4 g (171.7 mmol) of phenylboronic acid, 46.3 g (85.8 mmol) of dibromo-10H-acridin-9-one and 1.4 g (1.9 mmol) of Pd(PPh₃)₄ are suspended in 930 ml of dioxane. 85.8 ml of 2 M potassium carbonate solution are slowly added to this suspension, and the reaction mixture is heated under reflux for 16 h. After cooling, the organic phase is separated off, filtered through silica gel and subsequently evaporated to dryness. The residue is recrystallised from toluene/heptane.

Yield: 43 g (81 mmol), 94% of theory, purity according to GC>94%.

-continued
| Starting material 1 | Starting material 2 | Product | Yield |
|---|---|---|---|
| 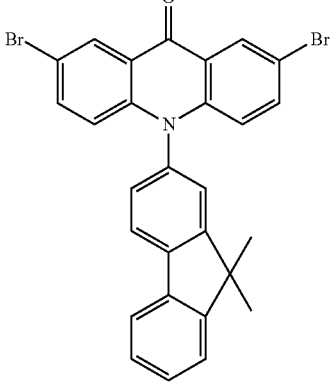 | 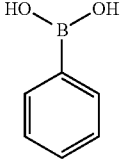 | 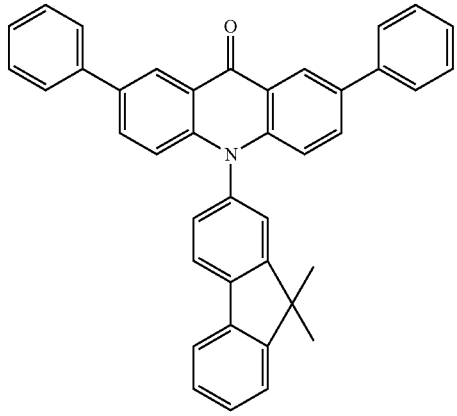 [SMILES: CC1(C)c2ccccc2-c2ccc(-n3c4ccc(-c5ccccc5)cc4c(=O)c4cc(-c5ccccc5)ccc43)cc21] | 91% |
| 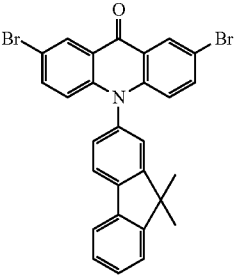 [SMILES: CC1(C)c2ccccc2-c2ccc(-n3c4ccc(Br)cc4c(=O)c4cc(Br)ccc43)cc21] | 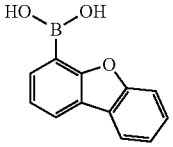 [SMILES: OB(O)c1cccc2c1oc1ccccc12] | 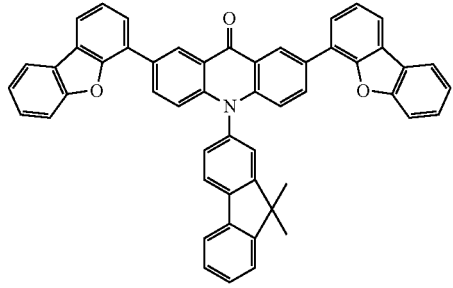 [SMILES: CC1(C)c2ccccc2-c2ccc(-n3c4ccc(-c5cccc6c5oc5ccccc56)cc4c(=O)c4cc(-c5cccc6c5oc5ccccc56)ccc43)cc21] | 87% |
| 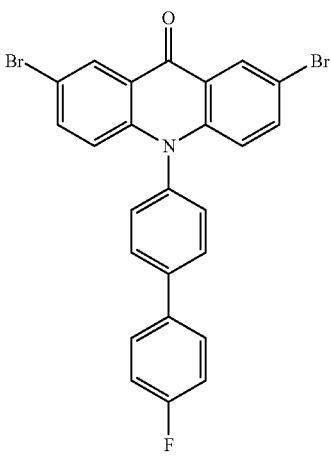 [SMILES: O=c1c2cc(Br)ccc2n(-c2ccc(-c3ccc(F)cc3)cc2)c2ccc(Br)cc12] | 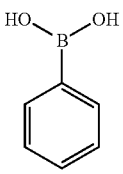 | 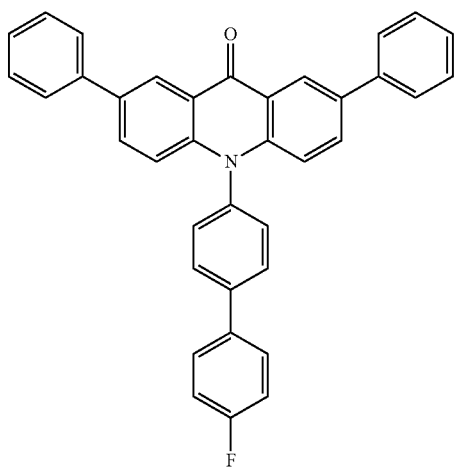 [SMILES: O=c1c2cc(-c3ccccc3)ccc2n(-c2ccc(-c3ccc(F)cc3)cc2)c2ccc(-c3ccccc3)cc12] | 95% |

| Starting material 1 | Starting material 2 | Product | Yield |
|---|---|---|---|
| 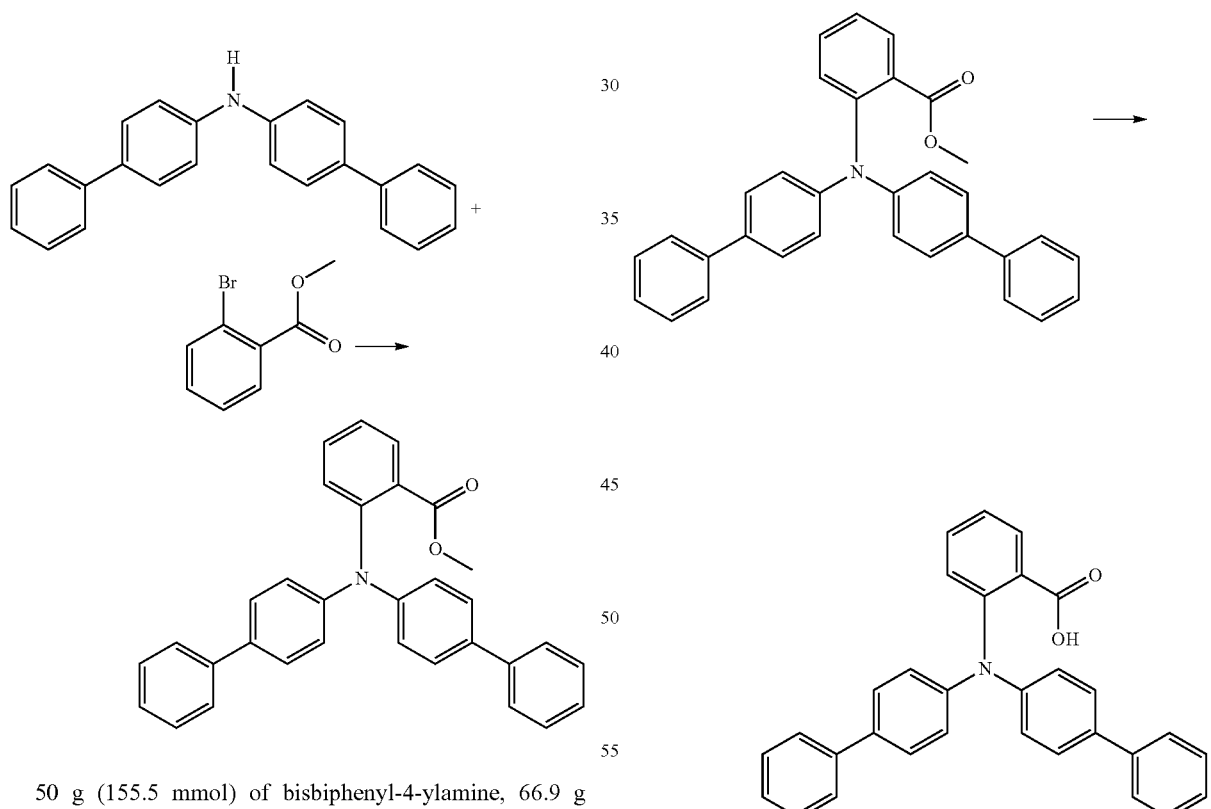 | | | 92% |

A-2) Synthesis of Asymmetrical Acridinones

Step 1:

50 g (155.5 mmol) of bisbiphenyl-4-ylamine, 66.9 g (311.1 mmol) of methyl 2-bromobenzoate, 21.5 g (155.5 mmol) of potassium carbonate, 22.1 g (155.5 mmol) of sodium sulfate and 0.9 g (15.5 mmol) of copper powder are suspended in 210 ml of nitrobenzene. The reaction mixture is heated at 220° C. for 6 h. After cooling, the mixture is filtered through Celite, and the nitrobenzene is distilled off. The residue is filtered through silica gel (heptane/dichloromethane 1:1). The product is obtained in the form of a solid. The yield is 64 g (91% of theory).

Step 2:

114.2 g (2722 mmol) of LiOH*H$_2$O are added to a solution of 62 g (136.1 mmol) of methyl benzoate in 294 ml of dioxane and 294 ml of water. The reaction mixture is heated at 105° C. for 16 h. After cooling, ethyl acetate is added, the mixture is added to 1500 ml of 10% citric acid solution and extracted with ethyl acetate. The combined organic phases are dried and evaporated in vacuo. The residue is used in the next step without further purification.

Step 3:

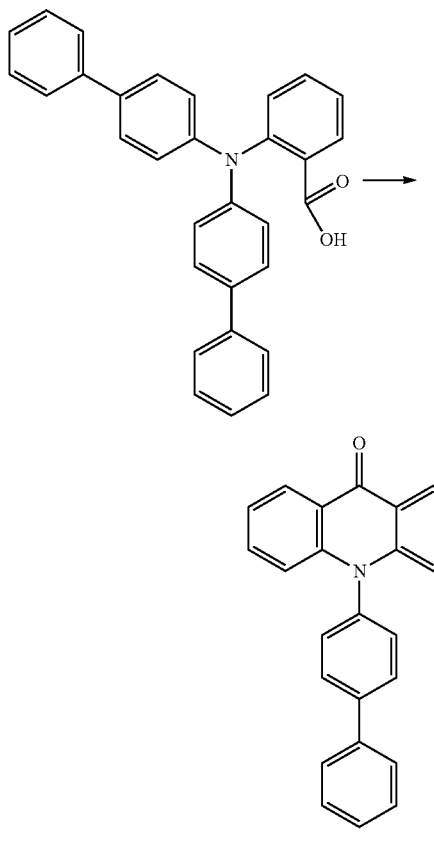

62 g (140 mmol) of benzoic acid are dissolved in 364 ml of methane-sulfonic acid, and the mixture is stirred overnight at 60° C. After cooling, the mixture is slowly added to ice/water, and the solid which has precipitated out is filtered off with suction. The solid is dissolved in ethyl acetate and washed with a 20% sodium hydrogencarbonate solution. The combined organic phases are dried and evaporated in vacuo. The residue is recrystallised from MeOH. The yield is 56 g (94% of theory).

A-3) Synthesis of a Diarylamino Intermediate

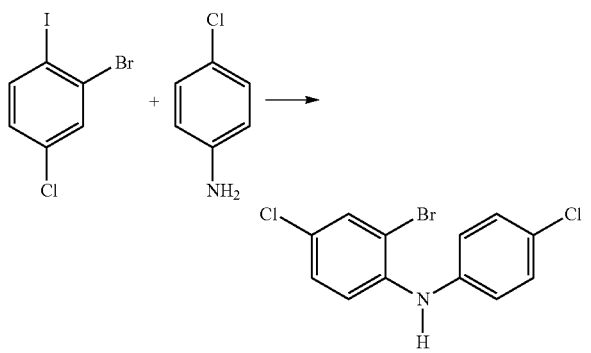

DPE-Phos (3.3 g, 6.2 mmol), palladium acetate (0.7 g, 3.1 mmol) and sodium tert-butoxide (41.5 g, 432 mmol) are added to a solution of 2-bromo-4-chloro-1-iodobenzene (50 g, 154 mmol) and 4-chlorophenylamine (19.7 g, 154 mmol) in degassed toluene (590 ml), and the mixture is heated under reflux for 20 h. The reaction mixture is cooled to room temperature, extended with toluene and filtered through Celite. The filtrate is extended with water, extracted with toluene, and the combined organic phases are dried and evaporated in vacuo. The residue is filtered through silica gel (heptane). The product is obtained in the form of a pale-red solid. The yield is 31 g (63% of theory).

A-4) Formation of the Spiro Unit

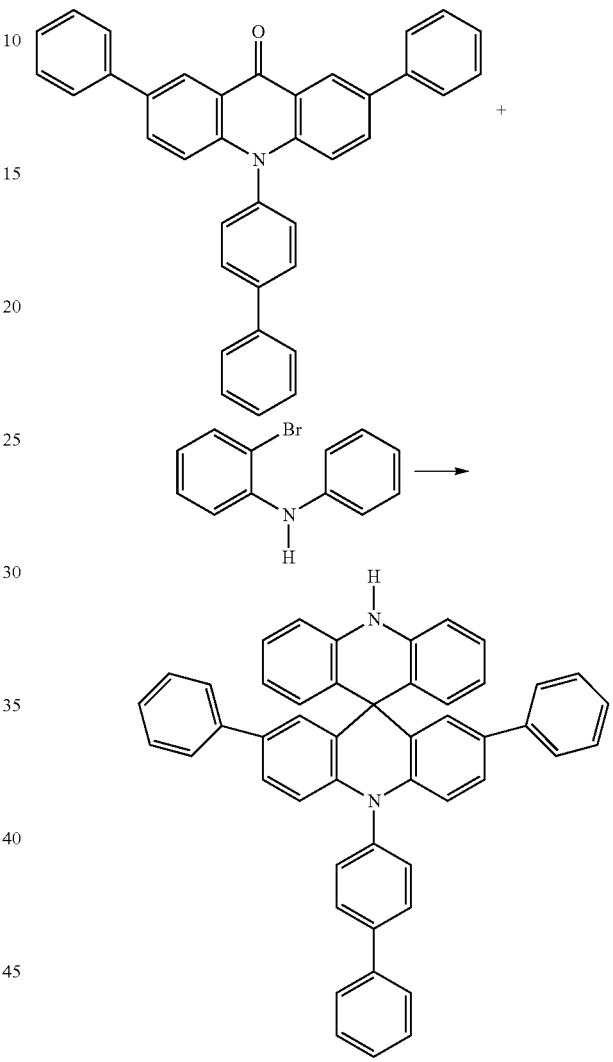

34.7 g (140 mmol) of 2-bromodiphenylamine are initially introduced in 350 ml of absolute THF, cooled to −78° C., and 112 ml (280 mmol) of 2.5 M n-BuLi in THF are added. The mixture is subsequently thawed to −10° C. and stirred at this temperature for a further 1 h. 30 g (86 mmol) of 10-biphenyl-4-yl-2,7-diphenyl-10H-acridin-9-one dissolved in 600 ml of THF are slowly added. The mixture is then stirred at room temperature for a further 24 h. 100 ml of ammonium chloride solution are added, stirring is continued briefly, the organic phase is separated off, and the solvent is removed in vacuo. The residue is suspended in 750 ml of warm glacial acetic acid at 40° C., 60 ml of conc. hydrochloric acid are added to the suspension, and the mixture is subsequently stirred at room temperature for a further 8 h. After cooling, the solid which has precipitated out is filtered off with suction, washed once with 100 ml of water, three times with 100 ml of ethanol each time and finally recrystallised from heptane. Yield: 35.3 g (54 mmol), 77% of theory.

| Starting material 1 | Starting material 2 | Product | Yield |
|---|---|---|---|
| 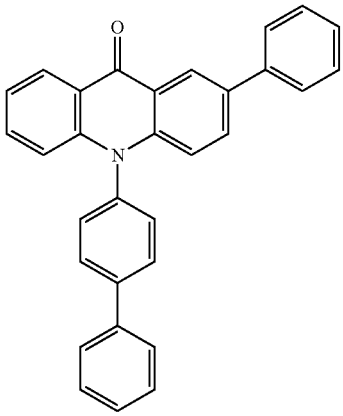 [SMILES: O=c1c2ccccc2n(-c2ccc(-c3ccccc3)cc2)c2ccc(-c3ccccc3)cc12] | 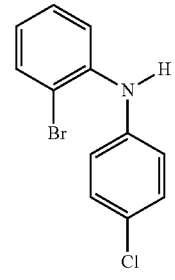 | 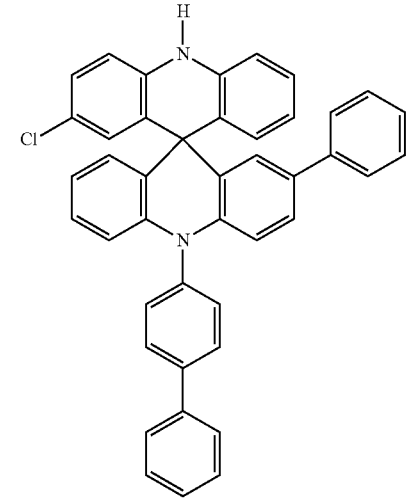 [SMILES: Clc1ccc2c(c1)C1(c3ccccc3N2)c2ccccc2N(c2ccc(-c3ccccc3)cc2)c2ccc(-c3ccccc3)cc21] | 85% |
| 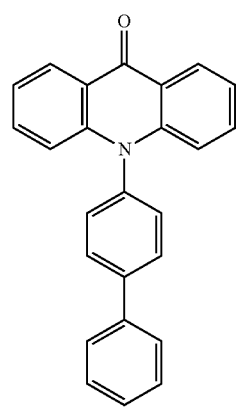 [SMILES: O=c1c2ccccc2n(-c2ccc(-c3ccccc3)cc2)c2ccccc12] | 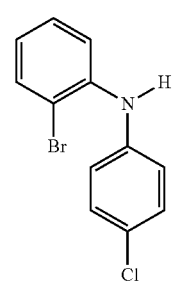 | 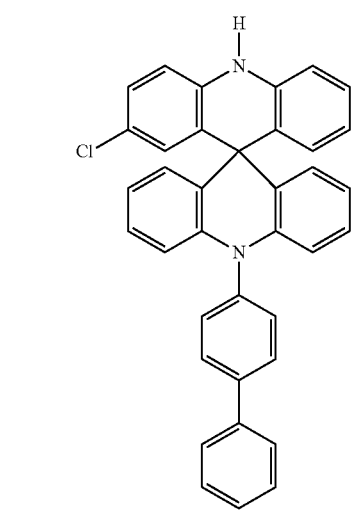 [SMILES: Clc1ccc2c(c1)C1(c3ccccc3N2)c2ccccc2N(c2ccc(-c3ccccc3)cc2)c2ccccc21] | 89% |
| 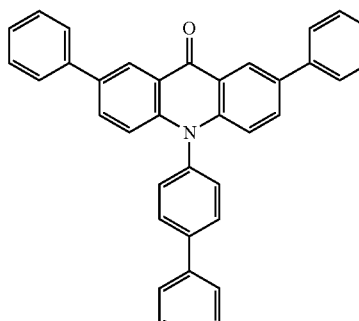 | 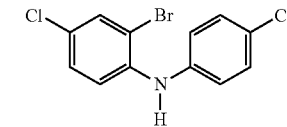 | 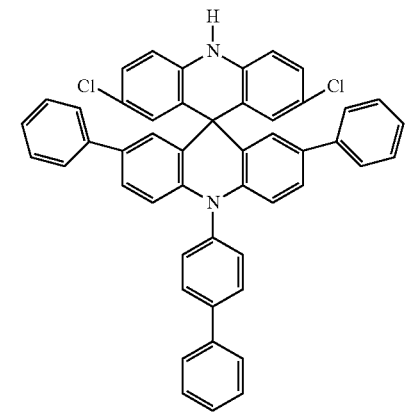 [SMILES: Clc1ccc2c(c1)C1(c3cc(Cl)ccc3N2)c2cc(-c3ccccc3)ccc2N(c2ccc(-c3ccccc3)cc2)c2ccc(-c3ccccc3)cc21] | 81% |

A-5) Suzuki Reaction

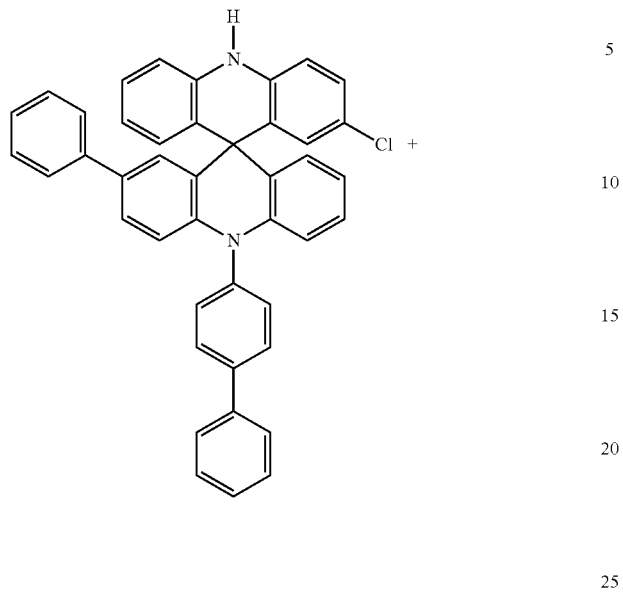

+

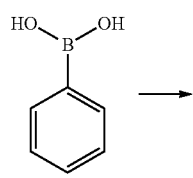

→

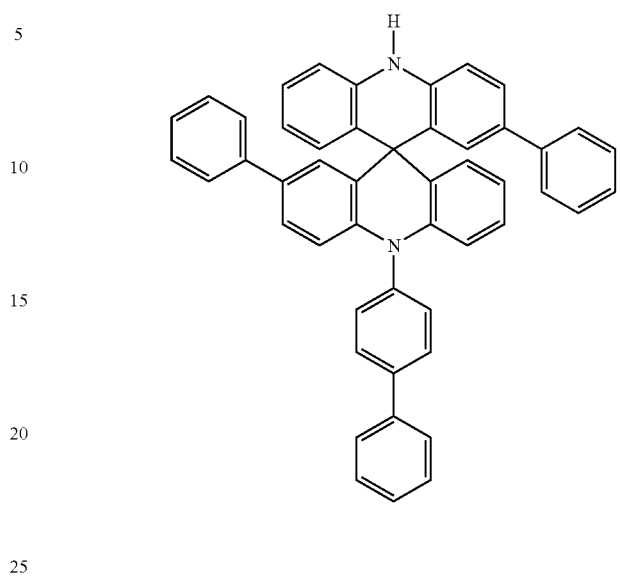

5.4 g (44.3 mmol) of benzeneboronic acid, 18 g (29.5 mmol) of 10-biphenyl-4-yl-2-chloro-9,9-dimethyl-9,10-dihydroacridine and 8.9 g (59.1 mmol) of CsF are suspended in 250 ml of dioxane. 1.1 g (1.5 mmol) of $PdCl_2(PCy_3)_2$ are added to this suspension, and the reaction mixture is heated under reflux for 16 h. After cooling, the mixture is filtered through silica gel, washed three times with 200 ml of water and subsequently evaporated to dryness. The residue is filtered through silica gel (heptane/ethyl acetate). The product is obtained in the form of a solid. The yield is 19 g (98% of theory).

| Ex. | Starting material 1 | Starting material 2 | Product | Yield |
|---|---|---|---|---|
| V1 | | | | 85% |

-continued
| Ex. | Starting material 1 | Starting material 2 | Product | Yield |
|---|---|---|---|---|
| 1 | 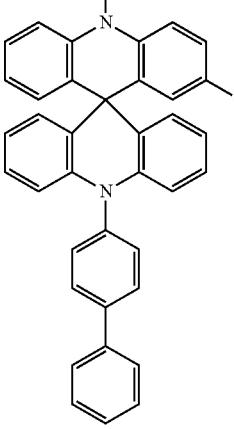 |  | 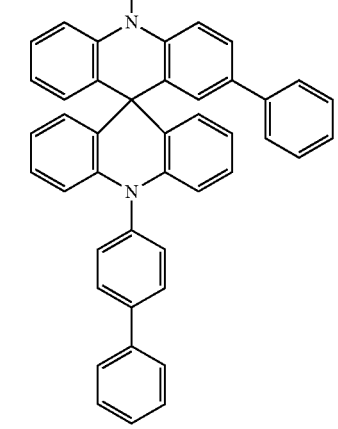 | 89% |
| 2 | 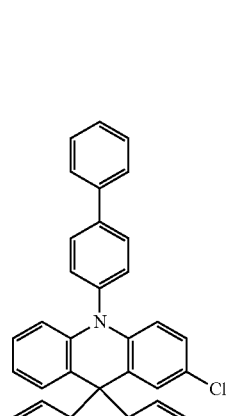 | 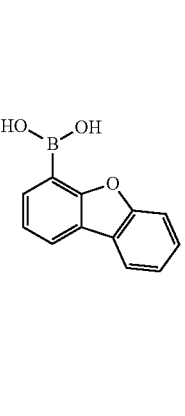 [SMILES: OB(O)c1cccc2c1oc1ccccc12] | 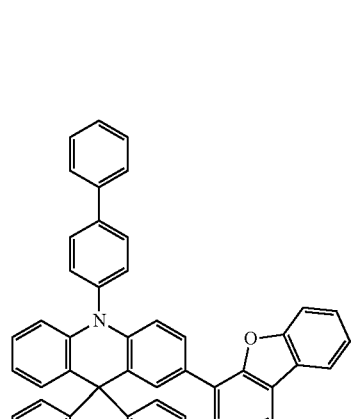 | 91% |

| Ex. | Starting material 1 | Starting material 2 | Product | Yield |
|---|---|---|---|---|
| V2 | 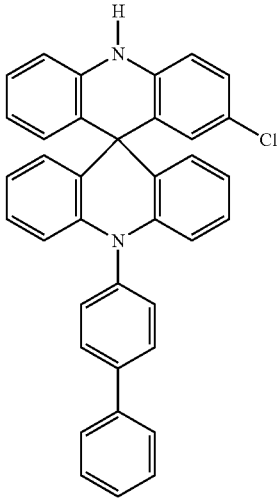 [SMILES: Clc1ccc2c(c1)C1(c3ccccc3N2)c2ccccc2N(c2ccc(-c3ccccc3)cc2)c2ccccc21] | 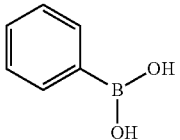 | 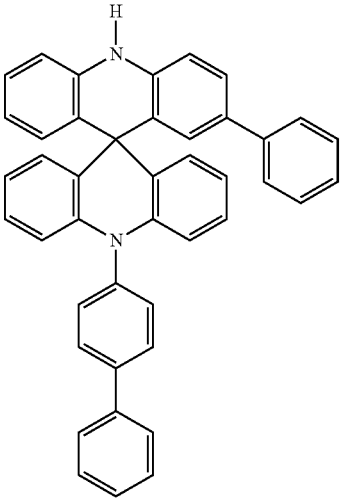 [SMILES: c1ccc(-c2ccc(N3c4ccccc4C4(c5ccccc5Nc5ccc(-c6ccccc6)cc54)c4ccccc43)cc2)cc1] | 90% |
| V3 | 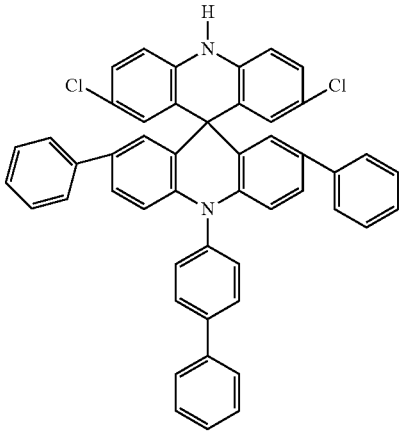 [SMILES: Clc1ccc2c(c1)C1(c3cc(Cl)ccc3N2)c2cc(-c3ccccc3)ccc2N(c2ccc(-c3ccccc3)cc2)c2ccc(-c3ccccc3)cc21] | 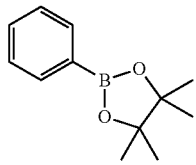 | 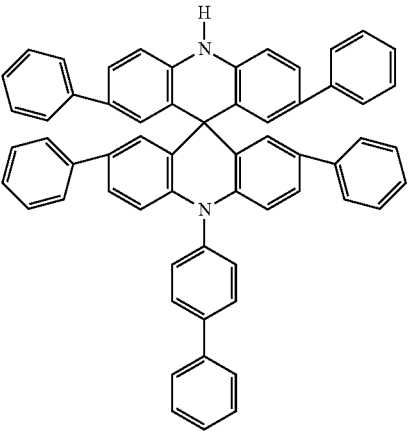 [SMILES: c1ccc(-c2ccc(N3c4ccc(-c5ccccc5)cc4C4(c5cc(-c6ccccc6)ccc5Nc5ccc(-c6ccccc6)cc54)c4cc(-c5ccccc5)ccc43)cc2)cc1] | 98% |
| 2b | 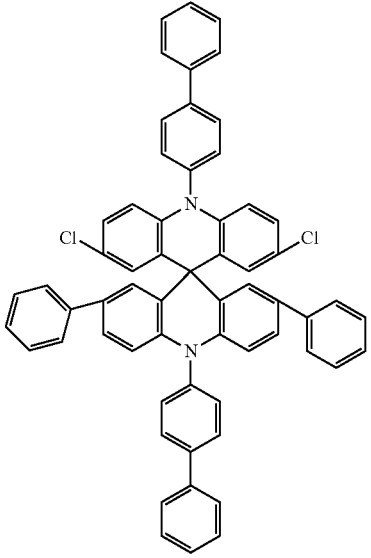 [SMILES: Clc1ccc2c(c1)C1(c3cc(Cl)ccc3N2c2ccc(-c3ccccc3)cc2)c2cc(-c3ccccc3)ccc2N(c2ccc(-c3ccccc3)cc2)c2ccc(-c3ccccc3)cc21] | 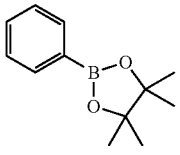 | 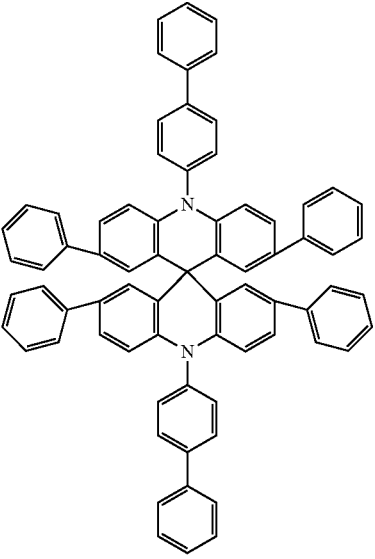 [SMILES: c1ccc(-c2ccc(N3c4ccc(-c5ccccc5)cc4C4(c5cc(-c6ccccc6)ccc53)c3cc(-c5ccccc5)ccc3N(c3ccc(-c5ccccc5)cc3)c3ccc(-c5ccccc5)cc34)cc2)cc1] | |

A-6) Buchwald Reaction

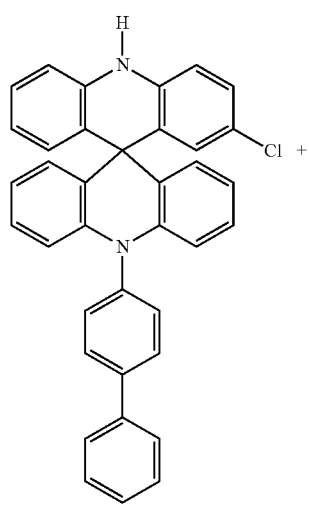

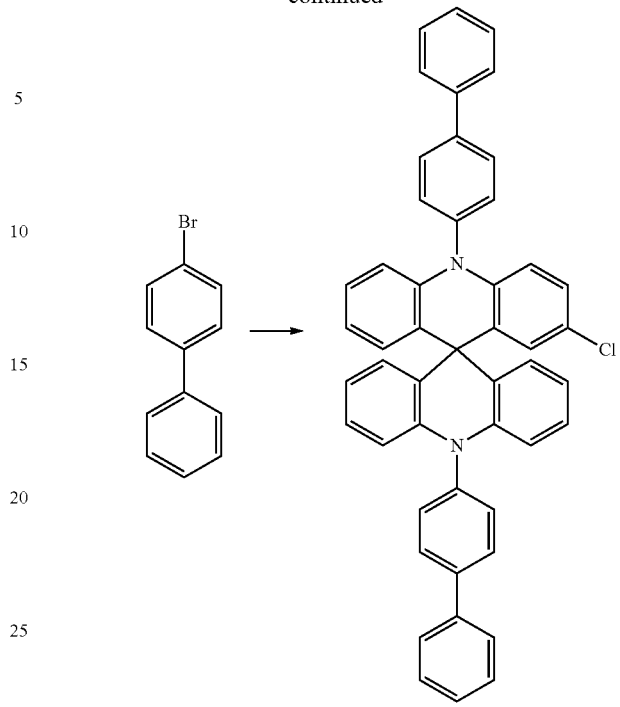

A degassed suspension of 11.1 g (46.7 mmol) of 4-bromobiphenyl, 24.9 g (46.7 mmol) of the spirobisacridine in 480 ml of toluene and 11.9 g (121.3 mmol) of NaOtBu is saturated with $N_2$ for 1 h. 1.07 g (1.9 mmol) of DPPF and 1.38 g (1.9 mmol) of palladium(II) acetate are then added. The reaction mixture is heated under reflux overnight. After cooling, the organic phase is filtered through silica gel and subsequently evaporated to dryness. The residue is recrystallised from toluene/heptane. Yield: 15.7 g (47% of theory).

| Ex. | Starting material 1 | Starting material 2 |
|---|---|---|
| 3 | | |

4 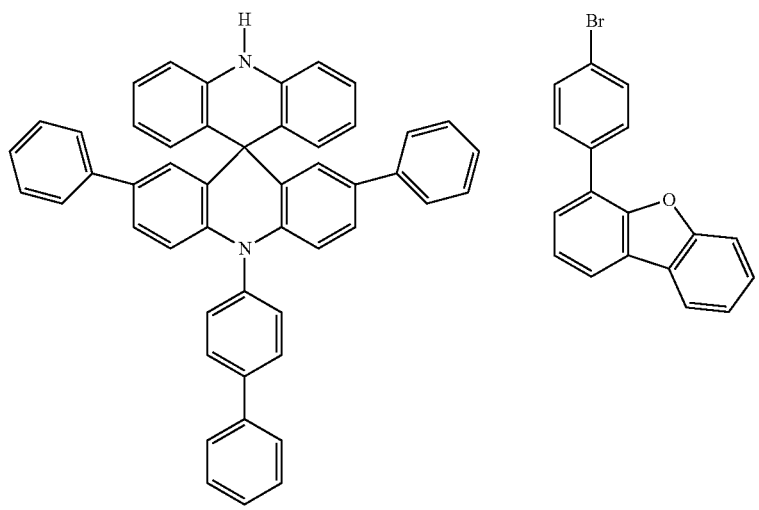
5 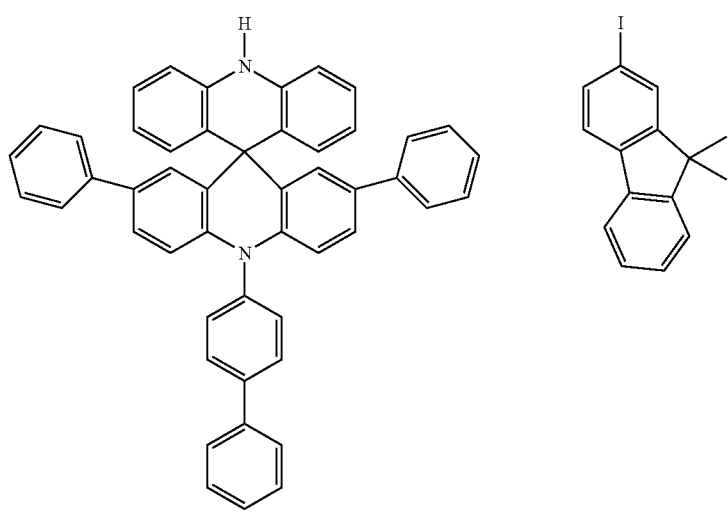
6 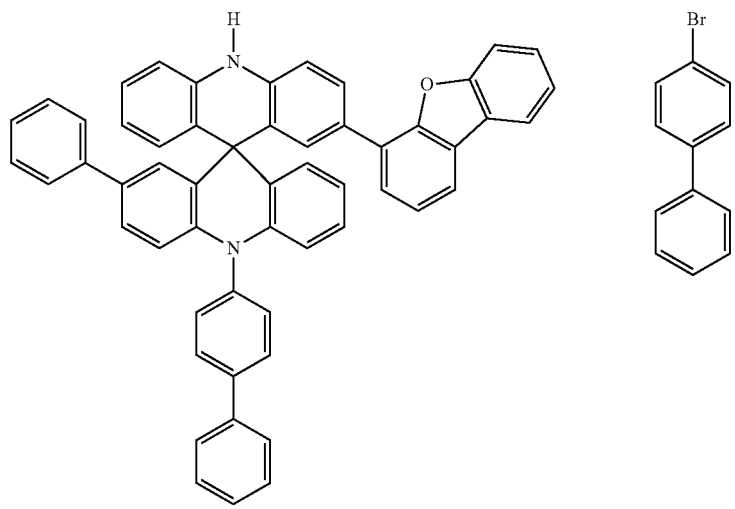

| | | |
|---|---|---|
| V4 | 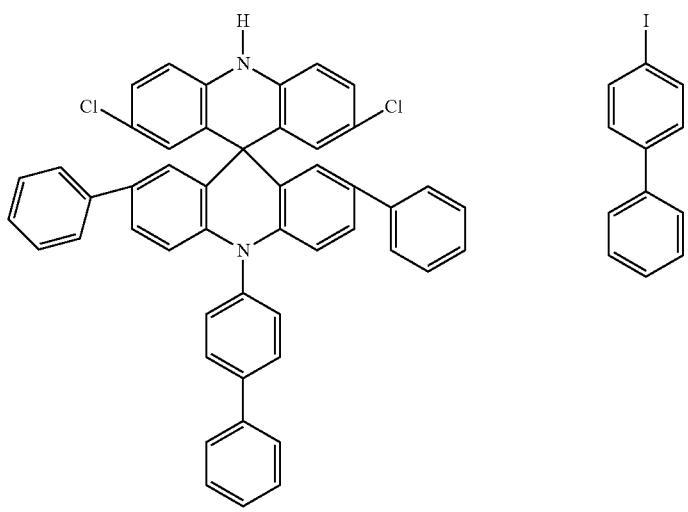 | 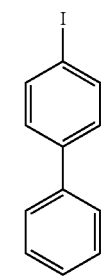 [SMILES: Ic1ccc(-c2ccccc2)cc1] |
| 7 | 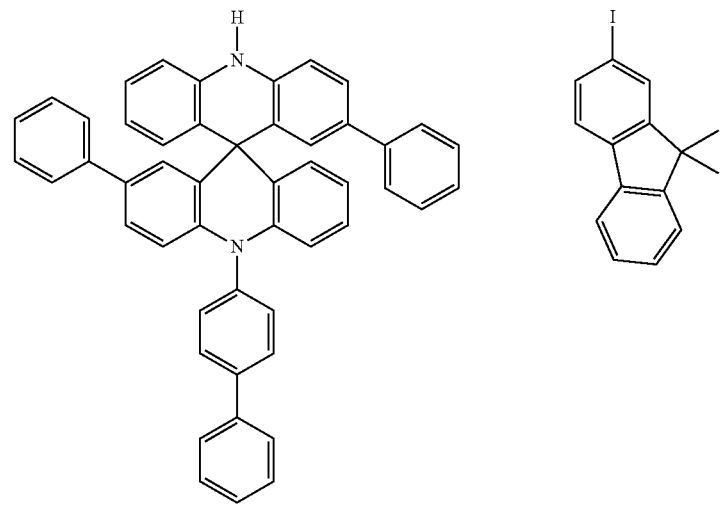 | 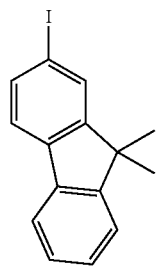 [SMILES: CC1(C)c2ccccc2-c2ccc(I)cc21] |
| 8 | 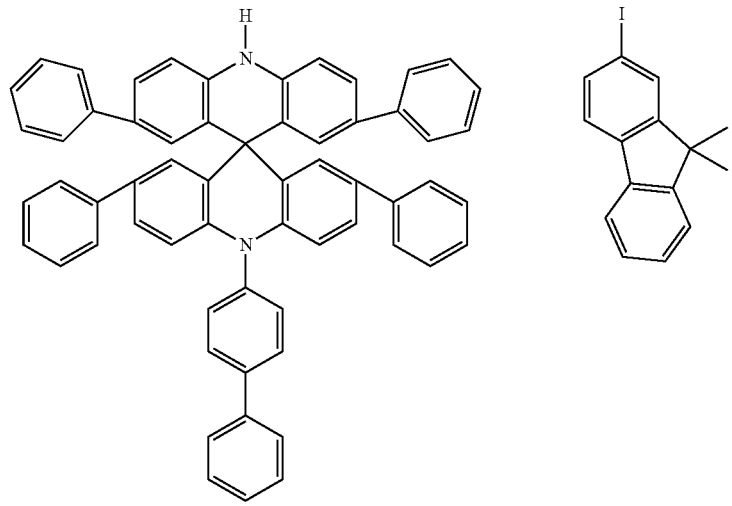 | 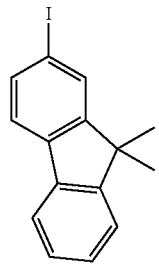 [SMILES: CC1(C)c2ccccc2-c2ccc(I)cc21] |

| | | |
|---|---|---|
| 9 | 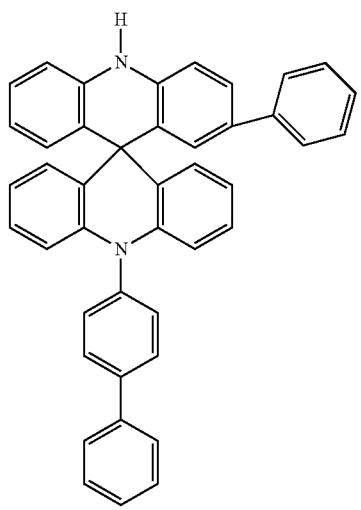 [SMILES: c1ccc(-c2ccc(N3c4ccccc4C4(c5ccccc5Nc5ccc(-c6ccccc6)cc54)c4ccccc43)cc2)cc1] | 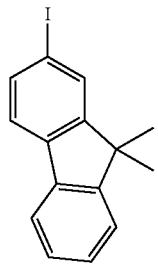 [SMILES: CC1(C)c2ccccc2-c2ccc(I)cc21] |
| 10 | 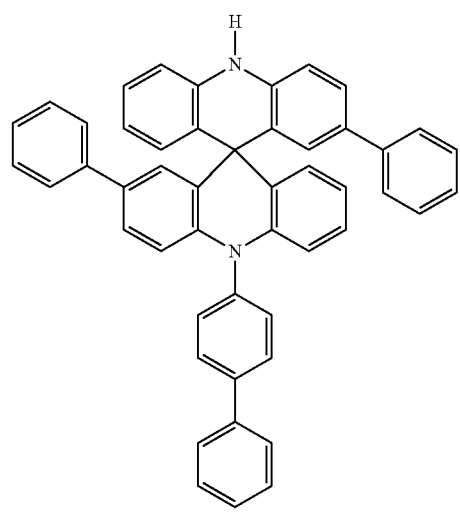 [SMILES: c1ccc(-c2ccc(N3c4ccccc4C4(c5ccccc5Nc5ccc(-c6ccccc6)cc54)c4cc(-c5ccccc5)ccc43)cc2)cc1] | 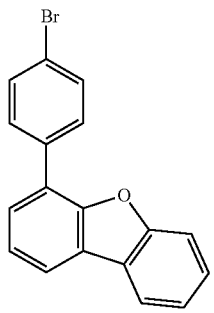 [SMILES: Brc1ccc(-c2cccc3c2oc2ccccc23)cc1] |

-continued
| Ex. | Product | Yield |
|---|---|---|
| 3 | 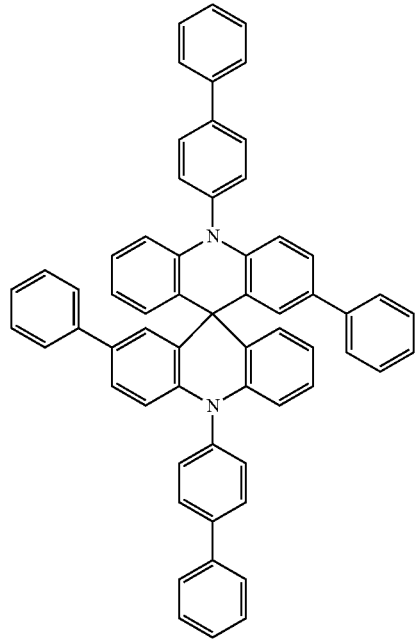 [SMILES: c1ccc(-c2ccc(N3c4ccccc4C4(c5ccccc5N(c5ccc(-c6ccccc6)cc5)c5ccc(-c6ccccc6)cc54)c4cc(-c5ccccc5)ccc43)cc2)cc1] | 65% |
| 4 | 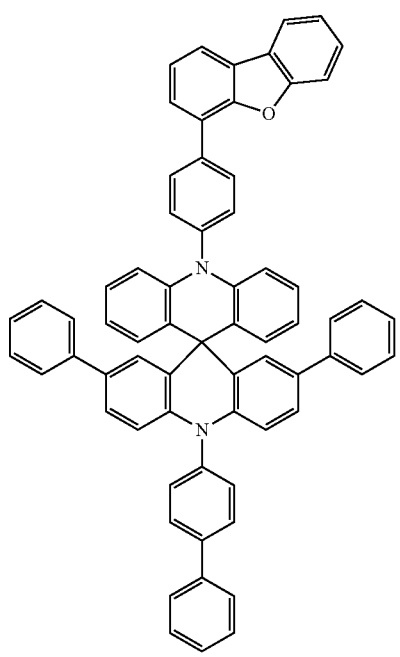 [SMILES: c1ccc(-c2ccc(N3c4ccc(-c5ccccc5)cc4C4(c5ccccc5N(c5ccc(-c6cccc7c6oc6ccccc67)cc5)c5ccccc54)c4cc(-c5ccccc5)ccc43)cc2)cc1] | 69% |

| 5 | 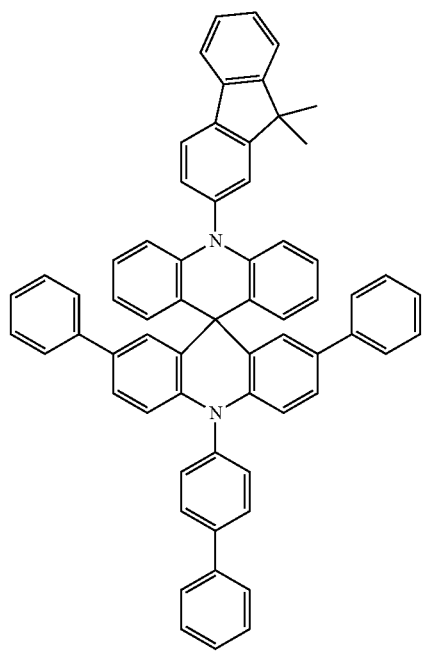 [SMILES: CC1(C)c2ccccc2-c2ccc(N3c4ccccc4C4(c5ccccc53)c3cc(-c5ccccc5)ccc3N(c3ccc(-c5ccccc5)cc3)c3ccc(-c5ccccc5)cc34)cc21] | 71% |
|---|---|---|
| 6 | 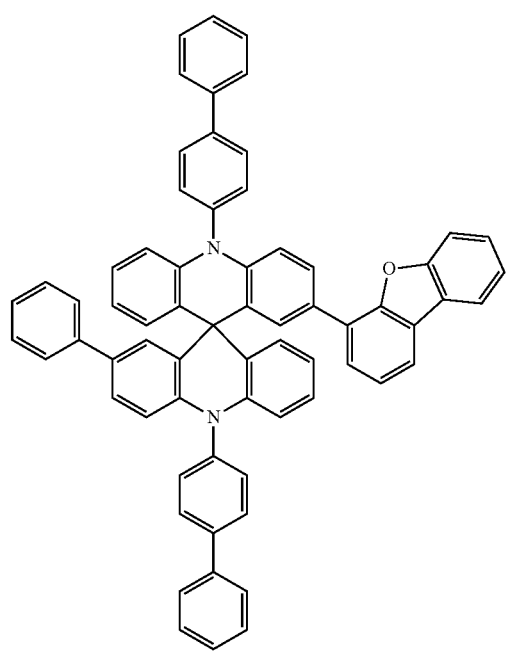 [SMILES: c1ccc(-c2ccc(N3c4ccccc4C4(c5ccccc5N(c5ccc(-c6ccccc6)cc5)c5ccc(-c6cccc7c6oc6ccccc67)cc54)c4cc(-c5ccccc5)ccc43)cc2)cc1] | 75% |

| | | |
|---|---|---|
| V4 | 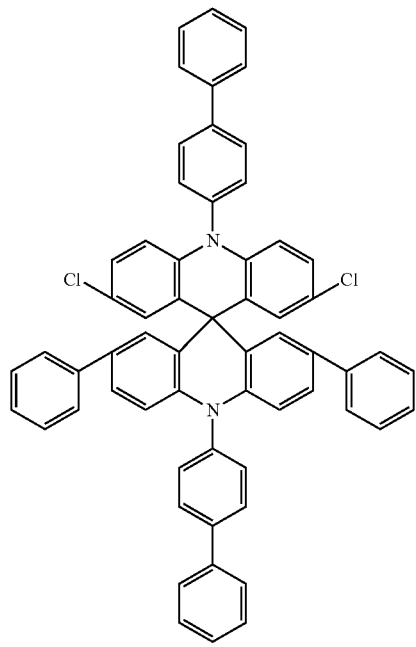 [SMILES: Clc1ccc2c(c1)C1(c3cc(Cl)ccc3N2c2ccc(-c3ccccc3)cc2)c2cc(-c3ccccc3)ccc2N(c2ccc(-c3ccccc3)cc2)c2ccc(-c3ccccc3)cc21] | 81% |
| 7 | 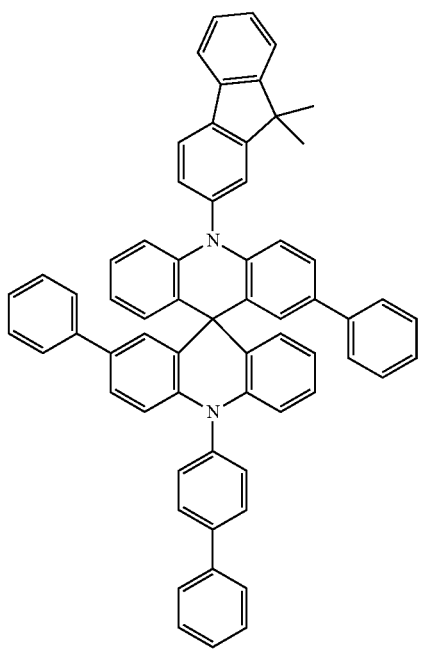 [SMILES: CC1(C)c2ccccc2-c2ccc(N3c4ccccc4C4(c5ccccc5N(c5ccc(-c6ccccc6)cc5)c5ccc(-c6ccccc6)cc54)c4cc(-c5ccccc5)ccc43)cc21] | 79% |

-continued
| 8 | 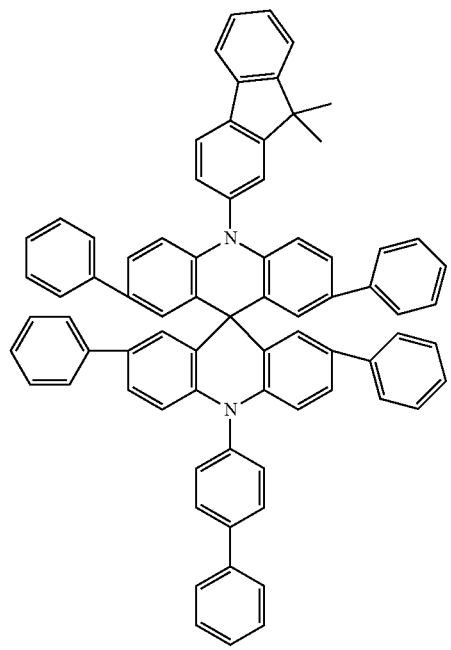 [SMILES: CC1(C)c2ccccc2-c2ccc(N3c4ccc(-c5ccccc5)cc4C4(c5cc(-c6ccccc6)ccc5N(c5ccc(-c6ccccc6)cc5)c5ccc(-c6ccccc6)cc54)c4cc(-c5ccccc5)ccc43)cc21] | 70% |
|---|---|---|
| 9 | 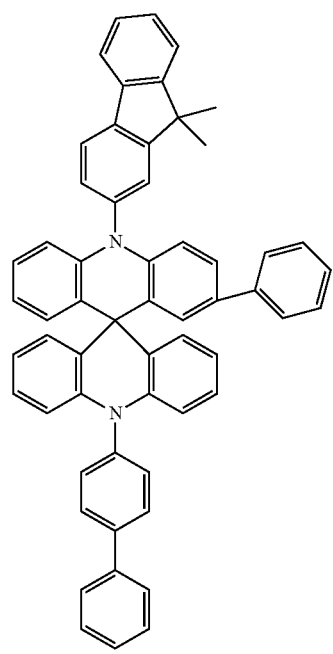 [SMILES: CC1(C)c2ccccc2-c2ccc(N3c4ccccc4C4(c5ccccc5N(c5ccc(-c6ccccc6)cc5)c5ccccc54)c4cc(-c5ccccc5)ccc43)cc21] | 60% |

10

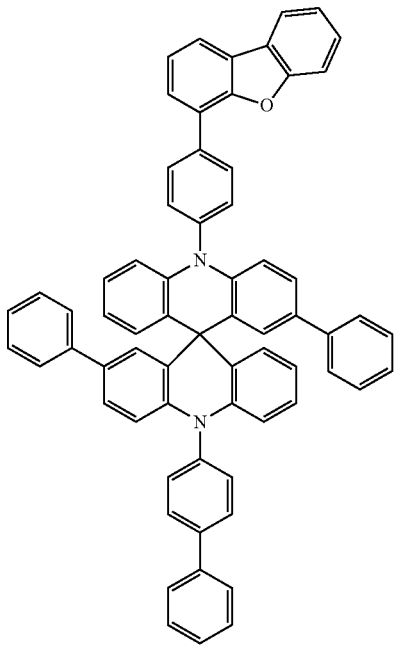 [SMILES: c1ccc(-c2ccc(N3c4ccccc4C4(c5ccccc5N(c5ccc(-c6cccc7c6oc6ccccc67)cc5)c5ccc(-c6ccccc6)cc54)c4cc(-c5ccccc5)ccc43)cc2)cc1]

B) Device Examples

OLEDs according to the invention and OLEDs in accordance with the prior art are produced by a general process in accordance with WO 04/058911, which is adapted to the circumstances described here (for example materials).

The data of various OLEDs are presented in the following examples E1-E16 according to the Invention and reference examples V1 to V4. The substrates used are glass plates coated with structured ITO (Indium tin oxide) in a thickness of 50 nm. The OLEDs have the following layer structure: substrate/p-doped hole-injection layer (HIL)/hole-transport layer (HTL)/optionally p-doped hole-transport layer/electron-blocking layer (EBL)/emission layer (EML)/electron-transport layer (ETL)/electron-injection layer (EIL) and finally a cathode. The cathode is formed by an aluminium layer with a thickness of 100 nm.

The materials required for the production of the OLEDs are shown in Table 1, the various component structures are shown in Table 2.

All materials are applied by thermal vapour deposition in a vacuum chamber. The emission layer here always consists of at least one matrix material (host material) and an emitting dopant (emitter), which is admixed with the matrix material or the matrix materials in a certain proportion by volume by co-evaporation. An expression such as H1:SEB (95%:5%) here means that material H1 is present in the layer in a proportion by volume of 95% and SEB is present in the layer in a proportion by volume of 5%. Analogously, the electron-transport layers or the hole-injection layers may also consist of a mixture of two or more materials.

The OLEDs are characterised by standard methods. For this purpose, the electroluminescence spectra and the current efficiency (in cd/A), the power efficiency and the external quantum efficiency (EQE, in percent) as a function of the luminous density, calculated from current/voltage/luminous density characteristic lines (IUL characteristic lines) assuming Lambert emission characteristics, and the lifetime are determined. The term EQE @10 mA/cm$^2$ denotes the external quantum efficiency at a current density of 10 mA/cm$^2$. LT80 @ 60 mA/cm$^2$ is the lifetime by which the OLED has dropped to 80% of the initial intensity at a constant current of 60 mA/cm$^2$.

TABLE 1

Structures of the materials used

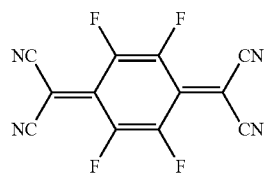 [SMILES: N#CC(C#N)=c1c(F)c(F)c(=C(C#N)C#N)c(F)c1F]

F4TCNQ

TABLE 1-continued
Structures of the materials used
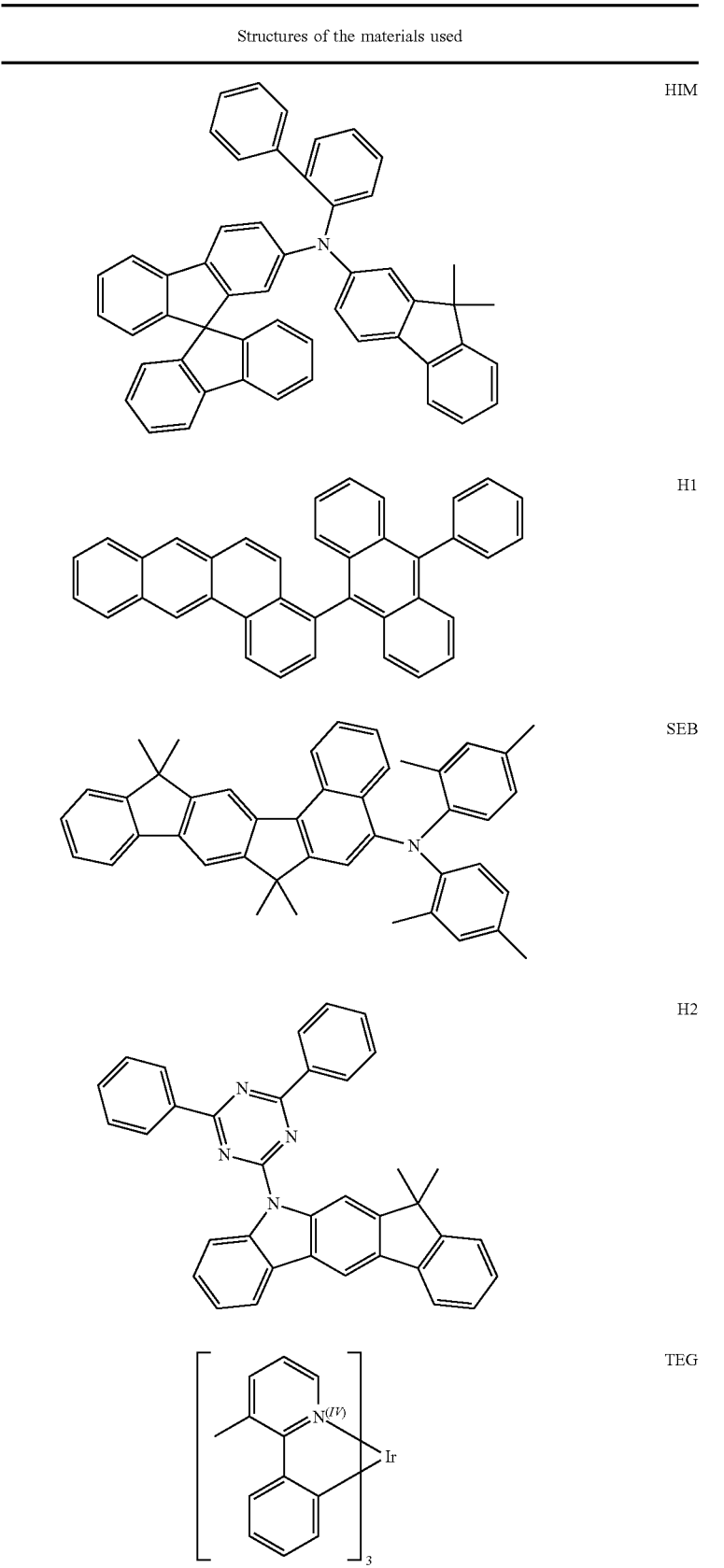
HIM
H1
SEB
H2
TEG TABLE 1-continued
Structures of the materials used
ETM
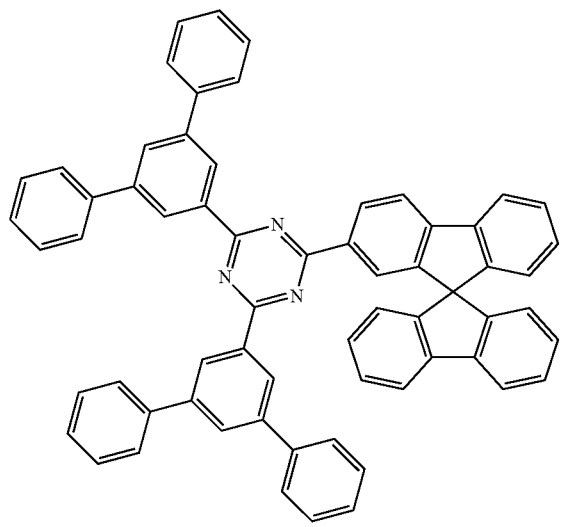 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
LiQ
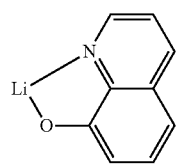
HTMV1
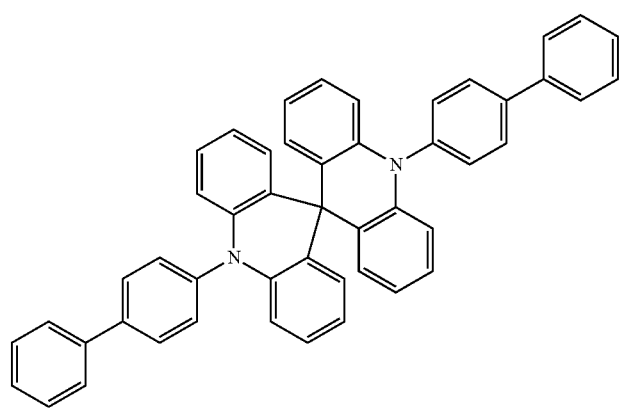 [SMILES: c1ccc(-c2ccc(N3c4ccccc4C4(c5ccccc53)c3ccccc3N(c3ccc(-c5ccccc5)cc3)c3ccccc34)cc2)cc1]
HTMV2
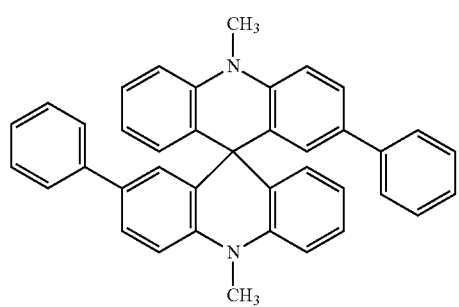 [SMILES: CN1c2ccccc2C2(c3ccccc3N(C)c3ccc(-c4ccccc4)cc32)c2cc(-c3ccccc3)ccc21]

TABLE 1-continued
Structures of the materials used
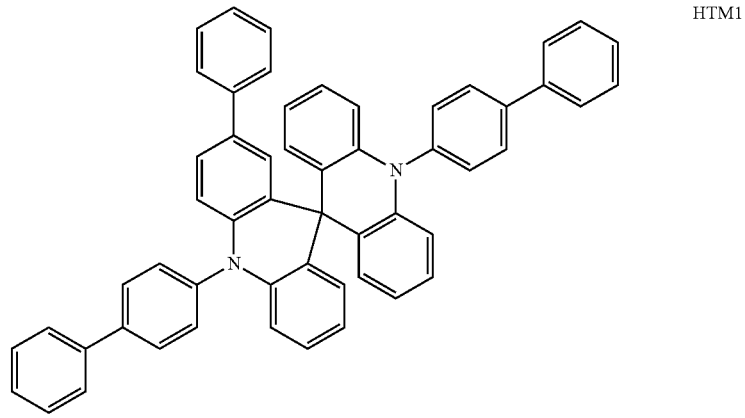
HTM1
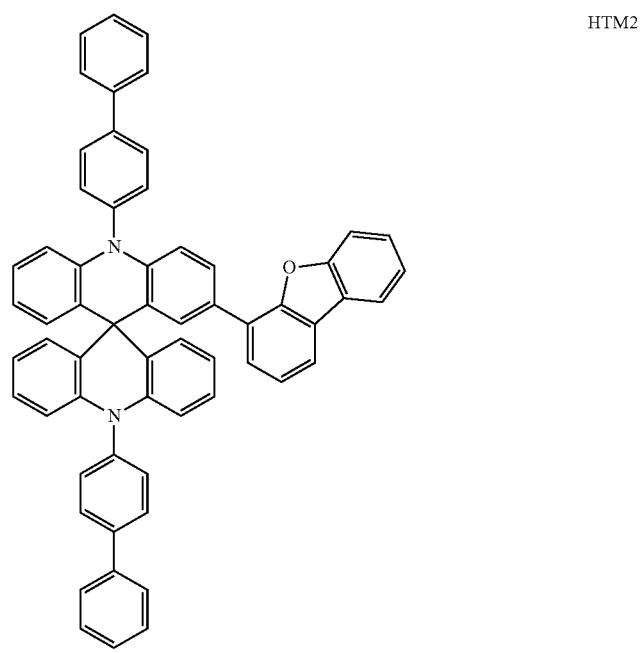
HTM2

TABLE 1-continued
Structures of the materials used
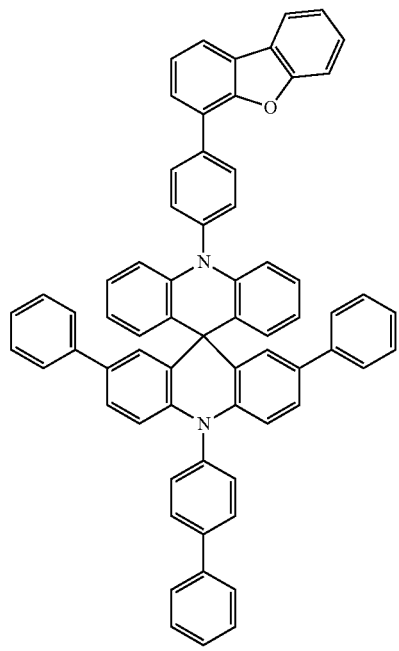 [SMILES: c1ccc(-c2ccc(N3c4ccc(-c5ccccc5)cc4C4(c5ccccc5N(c5ccc(-c6cccc7c6oc6ccccc67)cc5)c5ccccc54)c4cc(-c5ccccc5)ccc43)cc2)cc1]
HTM3
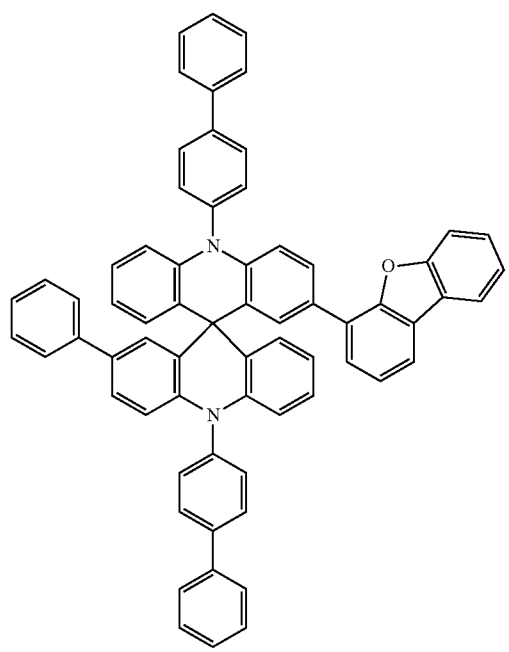 [SMILES: c1ccc(-c2ccc(N3c4ccccc4C4(c5ccccc5N(c5ccc(-c6ccccc6)cc5)c5ccc(-c6cccc7c6oc6ccccc67)cc54)c4cc(-c5ccccc5)ccc43)cc2)cc1]
HTM4

TABLE 1-continued
Structures of the materials used
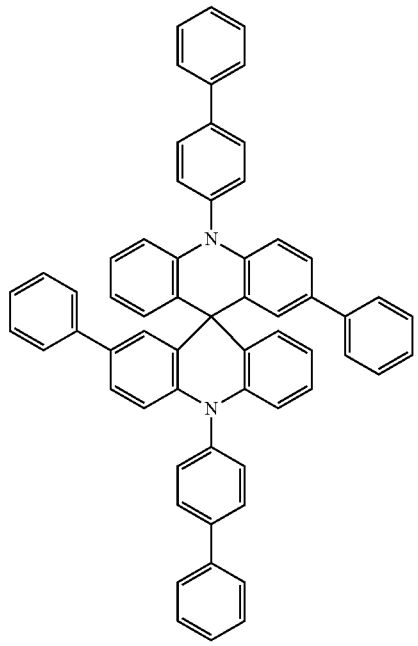 [SMILES: c1ccc(-c2ccc(N3c4ccccc4C4(c5ccccc5N(c5ccc(-c6ccccc6)cc5)c5ccc(-c6ccccc6)cc54)c4cc(-c5ccccc5)ccc43)cc2)cc1]
HTM5
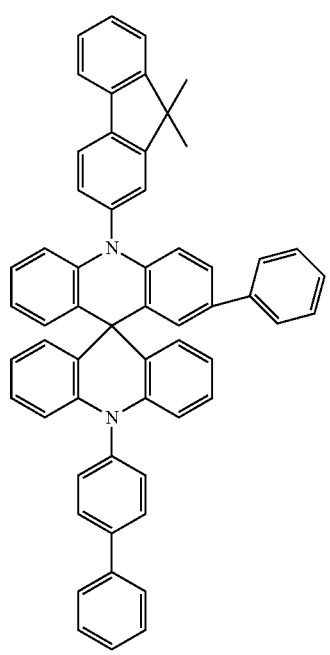 [SMILES: CC1(C)c2ccccc2-c2ccc(N3c4ccccc4C4(c5ccccc5N(c5ccc(-c6ccccc6)cc5)c5ccccc54)c4cc(-c5ccccc5)ccc43)cc21]
HTM6

TABLE 1-continued
Structures of the materials used
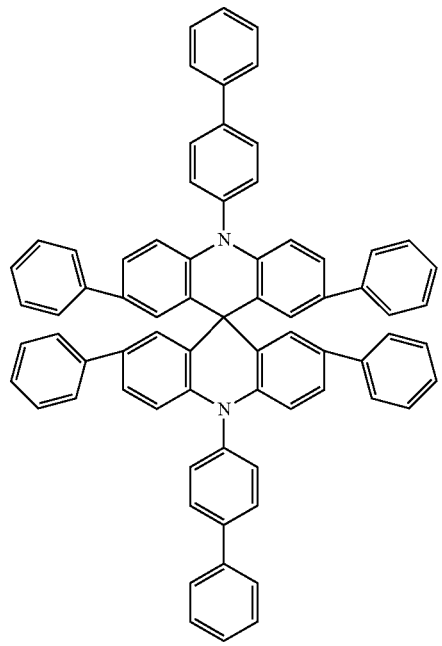 [SMILES: c1ccc(-c2ccc(N3c4ccc(-c5ccccc5)cc4C4(c5cc(-c6ccccc6)ccc53)c3cc(-c5ccccc5)ccc3N(c3ccc(-c5ccccc5)cc3)c3ccc(-c5ccccc5)cc34)cc2)cc1]
HTM7
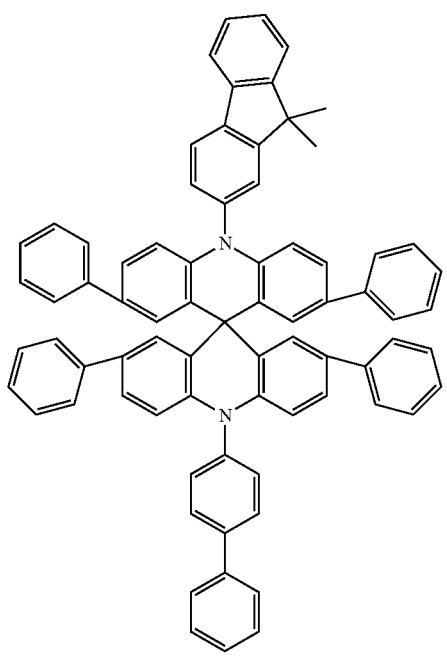 [SMILES: CC1(C)c2ccccc2-c2ccc(N3c4ccc(-c5ccccc5)cc4C4(c5cc(-c6ccccc6)ccc5N(c5ccc(-c6ccccc6)cc5)c5ccc(-c6ccccc6)cc54)c4cc(-c5ccccc5)ccc43)cc21]
HTM8

TABLE 2

Structure of the OLEDs

| Ex. | HIL1 Thickness/nm | HTL Thickness/nm | HIL2 Thickness/nm | EBL Thickness/nm | EML Thickness/nm | ETL Thickness/nm | EIL Thickness/nm |
|---|---|---|---|---|---|---|---|
| V1 | HIM:F4TCNQ(5%) 20 nm | HIM 175 nm | | HTMV2 20 nm | H1:SEB(5%) 20 nm | ETM:LiQ(50%) 30 nm | LiQ 1 nm |
| E1 | HIM:F4TCNQ(5%) 20 nm | HIM 175 nm | | HTM5 20 nm | H1:SEB(5%) 20 nm | ETM:LiQ(50%) 30 nm | LiQ 1 nm |
| V2 | HIM:F4TCNQ(5%) 20 nm | HIM 220 nm | HTMV2:F4TCNQ(5%) 20 nm | HTMV2 20 nm | H2:TEG(10%) 30 nm | ETM:LiQ(50%) 40 nm | LiQ 1 nm |
| E2 | HIM:F4TCNQ(5%) 20 nm | HIM 220 nm | HTM5:F4TCNQ(5%) 20 nm | HTM5 20 nm | H2:TEG(10%) 30 nm | ETM:LiQ(50%) 40 nm | LiQ 1 nm |
| V3 | HIM:F4TCNQ(5%) 20 nm | HIM 175 nm | | HTMV1 20 nm | H1:SEB(5%) 20 nm | ETM:LiQ(50%) 30 nm | LiQ 1 nm |
| E3 | HIM:F4TCNQ(5%) 20 nm | HIM 175 nm | | HTM1 20 nm | H1:SEB(5%) 20 nm | ETM:LiQ(50%) 30 nm | LiQ 1 nm |
| E4 | HIM:F4TCNQ(5%) 20 nm | HIM 175 nm | | HTM2 20 nm | H1:SEB(5%) 20 nm | ETM:LiQ(50%) 30 nm | LiQ 1 nm |
| E5 | HIM:F4TCNQ(5%) 20 nm | HIM 175 nm | | HTM3 20 nm | H1:SEB(5%) 20 nm | ETM:LiQ(50%) 30 nm | LiQ 1 nm |
| E6 | HIM:F4TCNQ(5%) 20 nm | HIM 175 nm | | HTM4 20 nm | H1:SEB(5%) 20 nm | ETM:LiQ(50%) 30 nm | LiQ 1 nm |
| E7 | HIM:F4TCNQ(5%) 20 nm | HIM 175 nm | | HTM6 20 nm | H1:SEB(5%) 20 nm | ETM:LiQ(50%) 30 nm | LiQ 1 nm |
| E8 | HIM:F4TCNQ(5%) 20 nm | HIM 175 nm | | HTM7 20 nm | H1:SEB(5%) 20 nm | ETM:LiQ(50%) 30 nm | LiQ 1 nm |
| E9 | HIM:F4TCNQ(5%) 20 nm | HIM 175 nm | | HTM8 20 nm | H1:SEB(5%) 20 nm | ETM:LiQ(50%) 30 nm | LiQ 1 nm |
| V4 | HIM:F4TCNQ(5%) 20 nm | HIM 220 nm | HTMV1:F4TCNQ(5%) 20 nm | HTMV1 20 nm | H2:TEG(10%) 30 nm | ETM:LiQ(50%) 40 nm | LiQ 1 nm |
| E10 | HIM:F4TCNQ(5%) 20 nm | HIM 220 nm | HTM1:F4TCNQ(5%) 20 nm | HTM1 20 nm | H2:TEG(10%) 30 nm | ETM:LiQ(50%) 40 nm | LiQ 1 nm |
| E11 | HIM:F4TCNQ(5%) 20 nm | HIM 220 nm | HTM2:F4TCNQ(5%) 20 nm | HTM2 20 nm | H2:TEG(10%) 30 nm | ETM:LiQ(50%) 40 nm | LiQ 1 nm |
| E12 | HIM:F4TCNQ(5%) 20 nm | HIM 220 nm | HTM3:F4TCNQ(5%) 20 nm | HTM3 20 nm | H2:TEG(10%) 30 nm | ETM:LiQ(50%) 40 nm | LiQ 1 nm |
| E13 | HIM:F4TCNQ(5%) 20 nm | HIM 220 nm | HTM4:F4TCNQ(5%) 20 nm | HTM4 20 nm | H2:TEG(10%) 30 nm | ETM:LiQ(50%) 40 nm | LiQ 1 nm |
| E14 | HIM:F4TCNQ(5%) 20 nm | HIM 220 nm | HTM6:F4TCNQ(5%) 20 nm | HTM6 20 nm | H2:TEG(10%) 30 nm | ETM:LiQ(50%) 40 nm | LiQ 1 nm |
| E15 | HIM:F4TCNQ(5%) 20 nm | HIM 220 nm | HTM7:F4TCNQ(5%) 20 nm | HTM7 20 nm | H2:TEG(10%) 30 nm | ETM:LiQ(50%) 40 nm | LiQ 1 nm |
| E16 | HIM:F4TCNQ(5%) 20 nm | HIM 220 nm | HTM8:F4TCNQ(5%) 20 nm | HTM8 20 nm | H2:TEG(10%) 30 nm | ETM:LiQ(50%) 40 nm | LiQ 1 nm |

Example 1

In Example 1, a substance according to the invention (HTM5) and a substance of the prior art (HTMV2) are compared in an OLED comprising a blue-fluorescent emitting layer. The compounds are each employed in hole-transporting layers of the OLED.

The external quantum efficiency at 10 mA/cm$^2$ of the compound according to the invention from sample E1 of 8.5% is significantly better than that of the reference sample V1 of only 6.0%. The lifetime LT80 at 60 mA/cm$^2$ is significantly increased in the case of sample E1 according to the invention, with 115 h, compared with the prior art in V1, with 38 h.

The two substances are likewise compared in a triplet green component. Reference sample V2 exhibits a significantly lower quantum efficiency at 2 mA/cm$^2$ of 16.3% than sample E2 according to the invention of 20.1%. The lifetime LT80 of sample E2 according to the invention of 223 h is significantly longer than the reference lifetime of V2 of 96 h.

Example 2

In Example 2, a further four substances according to the invention (HTM1, HTM2, HTM3 and HTM4) are compared with the prior art (HTMV1). In a singlet blue component, sample E3 according to the invention achieves a higher quantum efficiency at 10 mA/cm$^2$ of 9.8% than the prior art (V3) of 8.5%. The lifetimes (80%) of the components comprising materials E3-E6 according to the invention, of E3 (214 h), E4 (180 h), E5 (154 h) and E6 (166 h), are significantly longer than the lifetime of the comparative material (V3) of 66 h.

In a triplet green component, reference sample V4 (19.8%) exhibits a lower quantum efficiency at 2 mA/cm$^2$ than, for example, sample E10 according to the invention (20.4%). The lifetimes (80%) at 20 mA/cm$^2$ of samples according to the invention E10 (199 h), E11 (223 h), E12 (205 h) and E13 (214 h) are also longer than in the case of the prior art V4 of only 193 h.

Example 3

In Example 3, a further three substances according to the invention (HTM6, HTM7 and HTM8) are compared with the prior art (HTMV1). In a singlet blue component, samples according to the invention E8 and E9 achieve a higher quantum efficiency at 10 mA/cm$^2$ of 8.6% and 9.1% respectively than the prior art (V3) of 8.5%. The lifetime (80%) of the component comprising material E8 according to the invention of 150 h is significantly longer than the lifetime of comparative component V3 of 66 h.

In a triplet green component, reference sample V4 (19.8%) exhibits a lower quantum efficiency at 2 mA/cm² than samples according to the invention E14 (21.5%), E15 (20.2%) and E16 (20.6%).

The invention claimed is:

1. A compound of the formula (I)

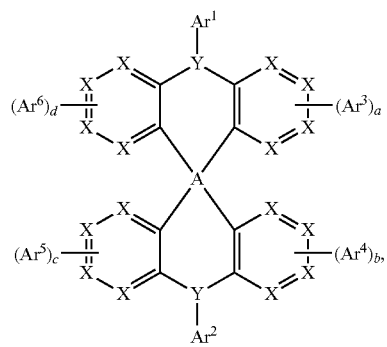

formula (I)

where the following applies to the symbols and indices occurring:

A is C;

Y is N;

X is on each occurrence, identically or differently, $CR^1$ or N;

$Ar^1$, $Ar^2$ are on each occurrence, identically or differently, selected from the formula (Ar-2) to (Ar-15) and (Ar-18) to (Ar-66)

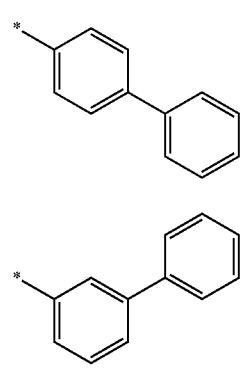

formula (Ar-2)

formula (Ar-3)

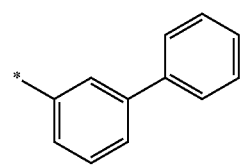

formula (Ar-4)

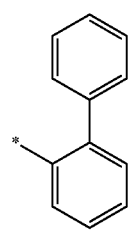

-continued

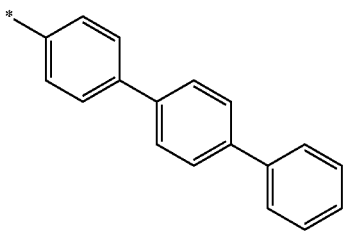

formula (Ar-5)

formula (Ar-6)

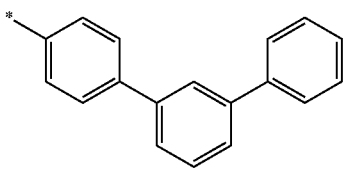

formula (Ar-7)

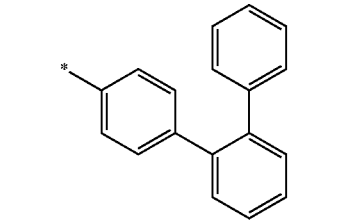

formula (Ar-8)

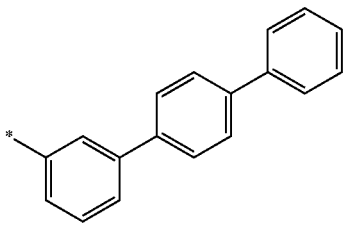

formula (Ar-9)

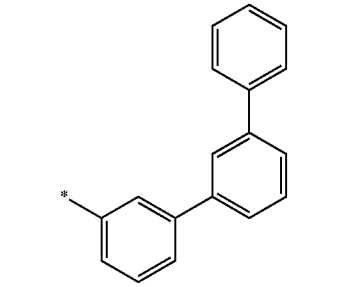

formula (Ar-10)

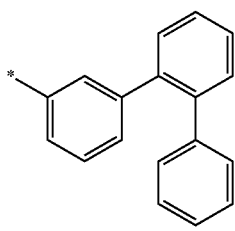

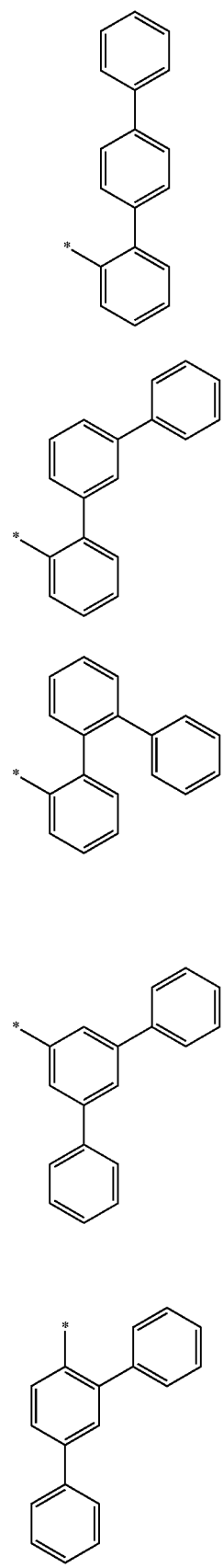
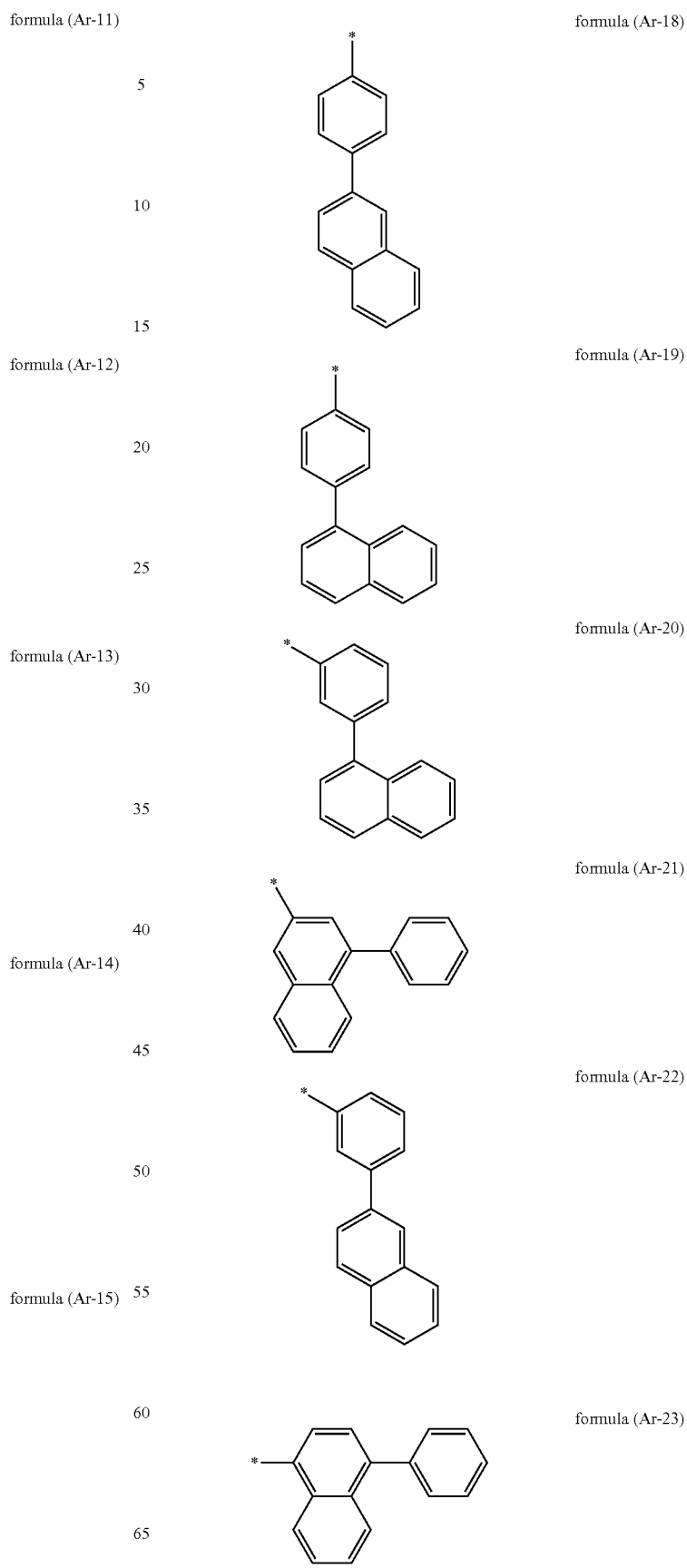

-continued
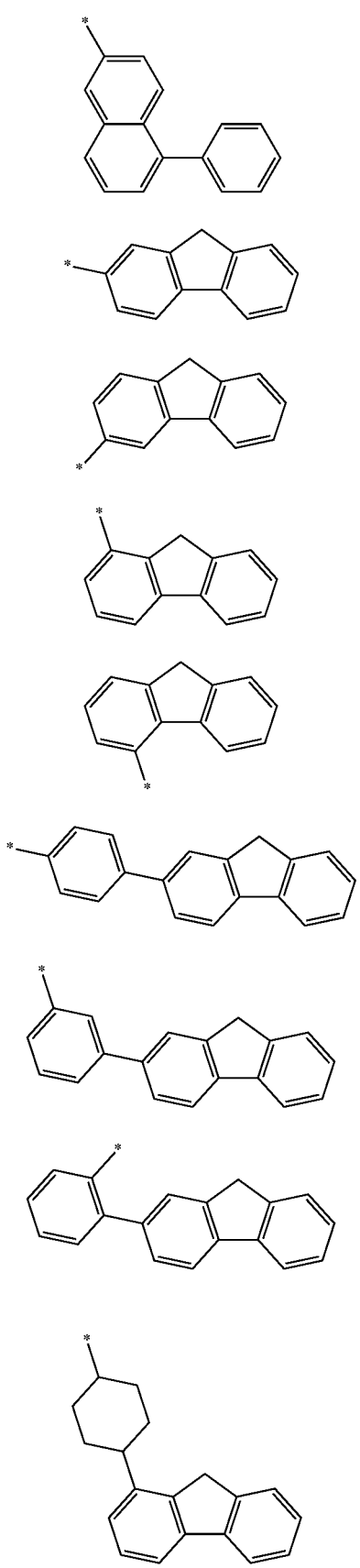
formula (Ar-24)
formula (Ar-25)
formula (Ar-26)
formula (Ar-27)
formula (Ar-28)
formula (Ar-29)
formula (Ar-30)
formula (Ar-31)
-continued
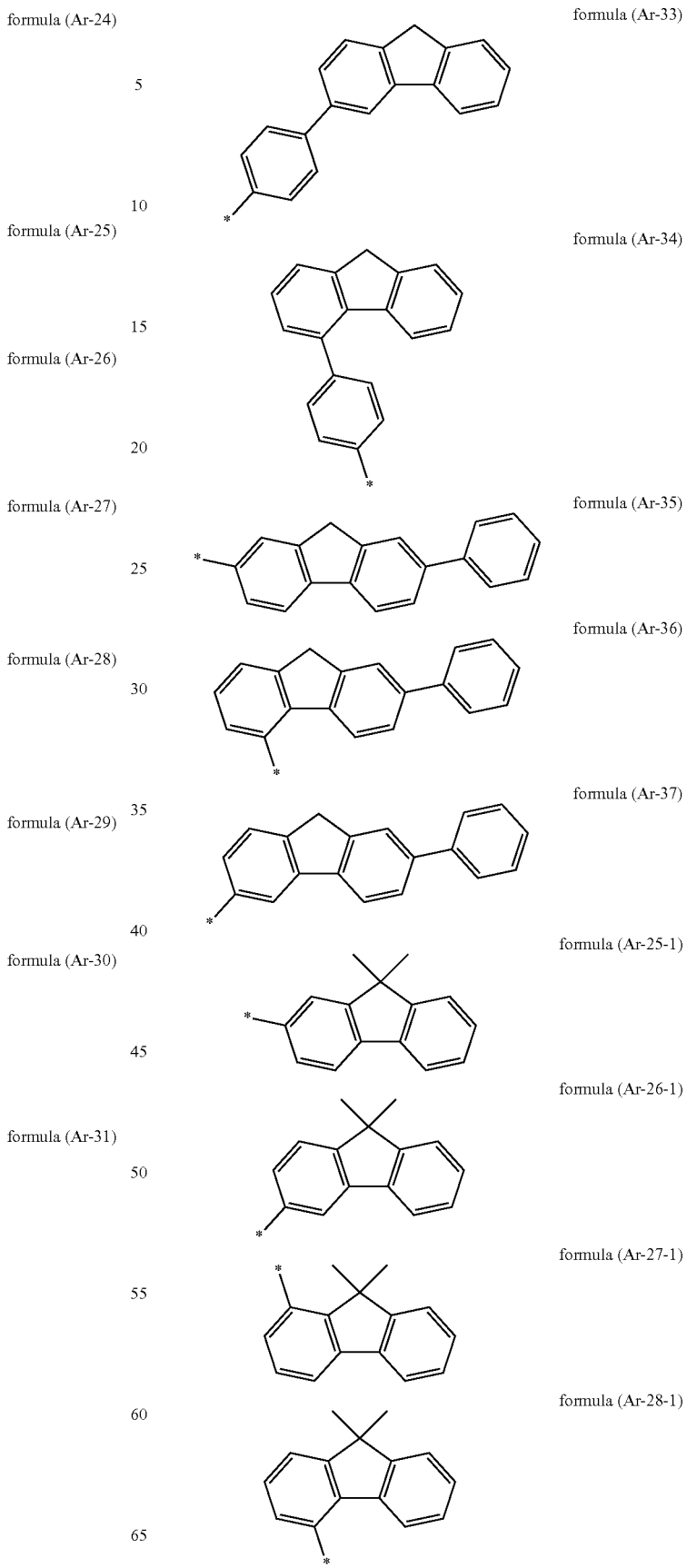
formula (Ar-33)
formula (Ar-34)
formula (Ar-35)
formula (Ar-36)
formula (Ar-37)
formula (Ar-25-1)
formula (Ar-26-1)
formula (Ar-27-1)
formula (Ar-28-1)

formula (Ar-29-1)
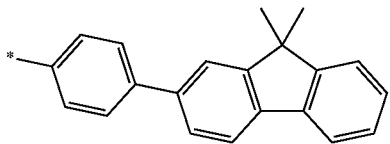
formula (Ar-30-1)
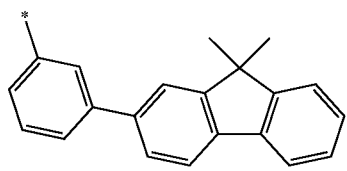
formula (Ar-31-1)
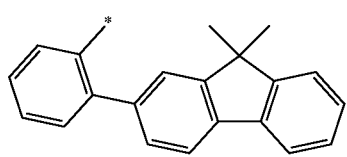
formula (Ar-32-1)
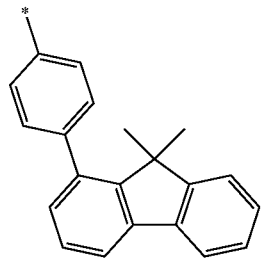
formula (Ar-33-1)
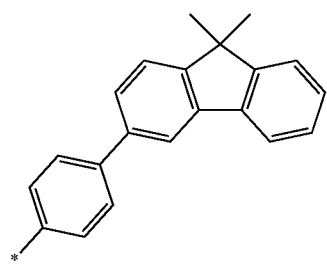
formula (Ar-34-1)
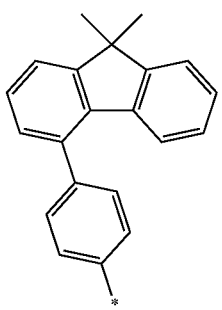
formula (Ar-35-1)
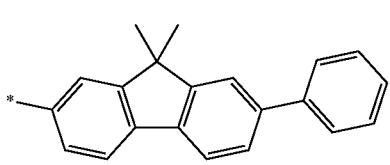
formula (Ar-36-1)
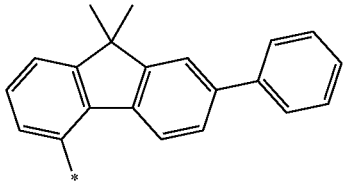
formula (Ar-37-1)
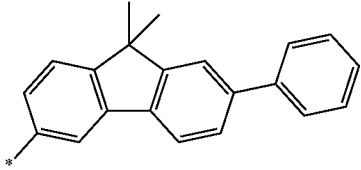
formula (Ar-25-2)
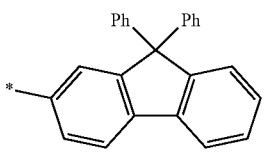
formula (Ar-26-2)
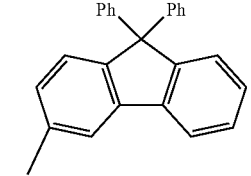
formula (Ar-27-2)
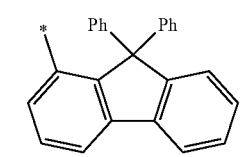
formula (Ar-28-2)
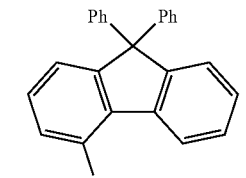
formula (Ar-29-2)
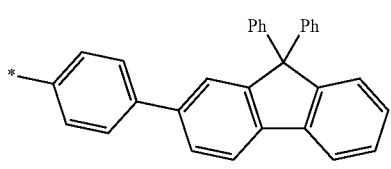
formula (Ar-30-2)
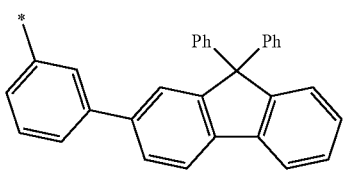
formula (Ar-31-2)
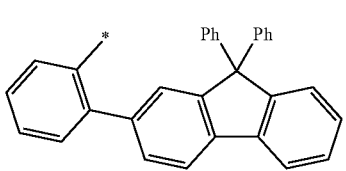

-continued formula (Ar-32-2)

formula (Ar-33-2)

formula (Ar-34-2)

formula (Ar-35-2)

formula (Ar-36-2)

formula (Ar-37-2)

formula (Ar-25-3)

-continued formula (Ar-26-3)

formula (Ar-27-3)

formula (Ar-28-3)

formula (Ar-29-3)

formula (Ar-30-3)

formula (Ar-31-3)

formula (Ar-32-3)

formula (Ar-33-3)

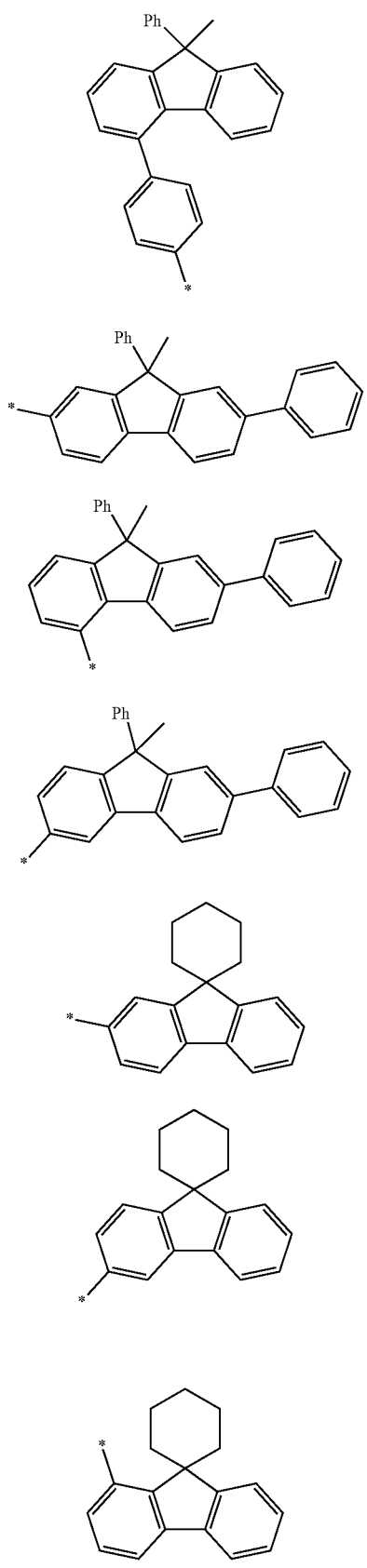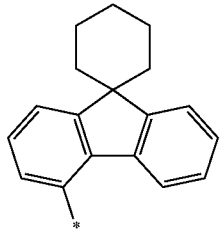

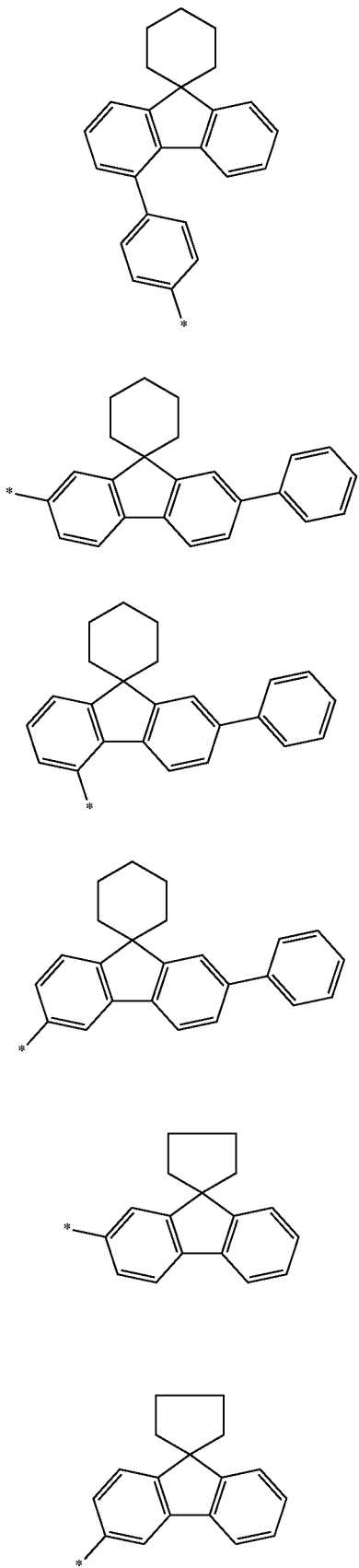
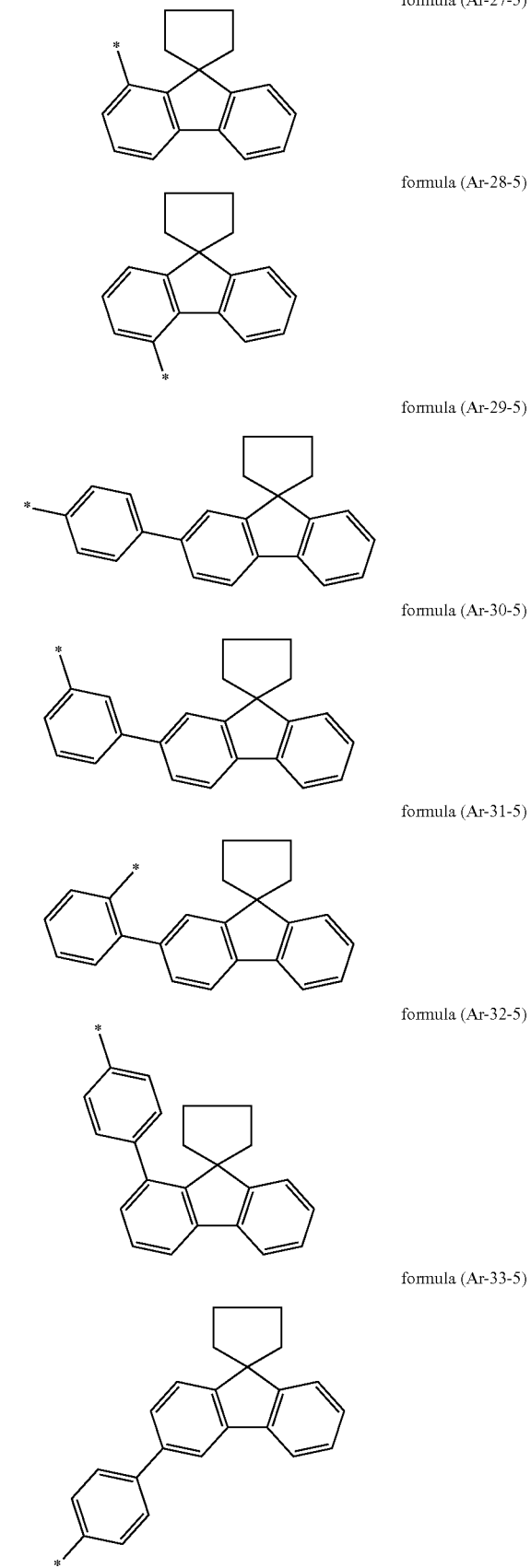

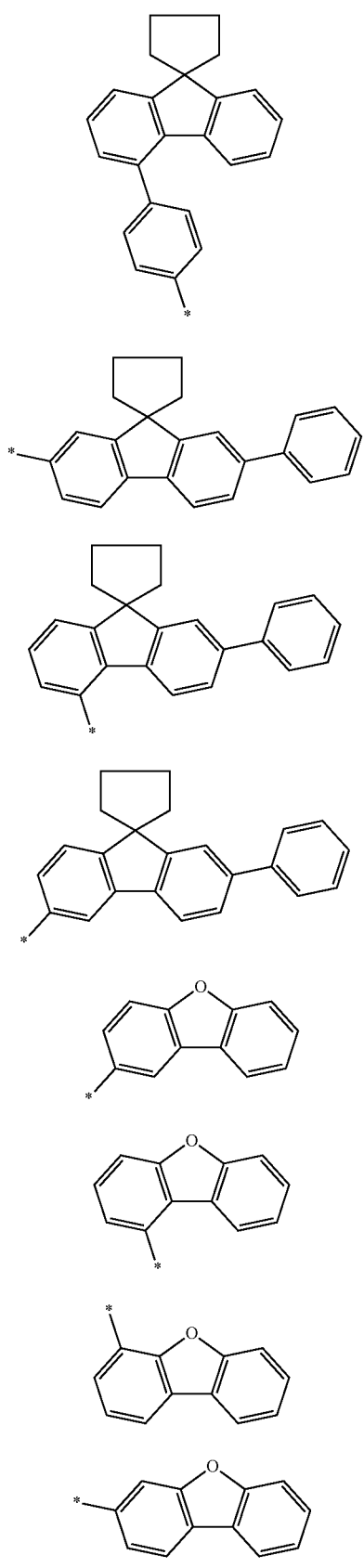
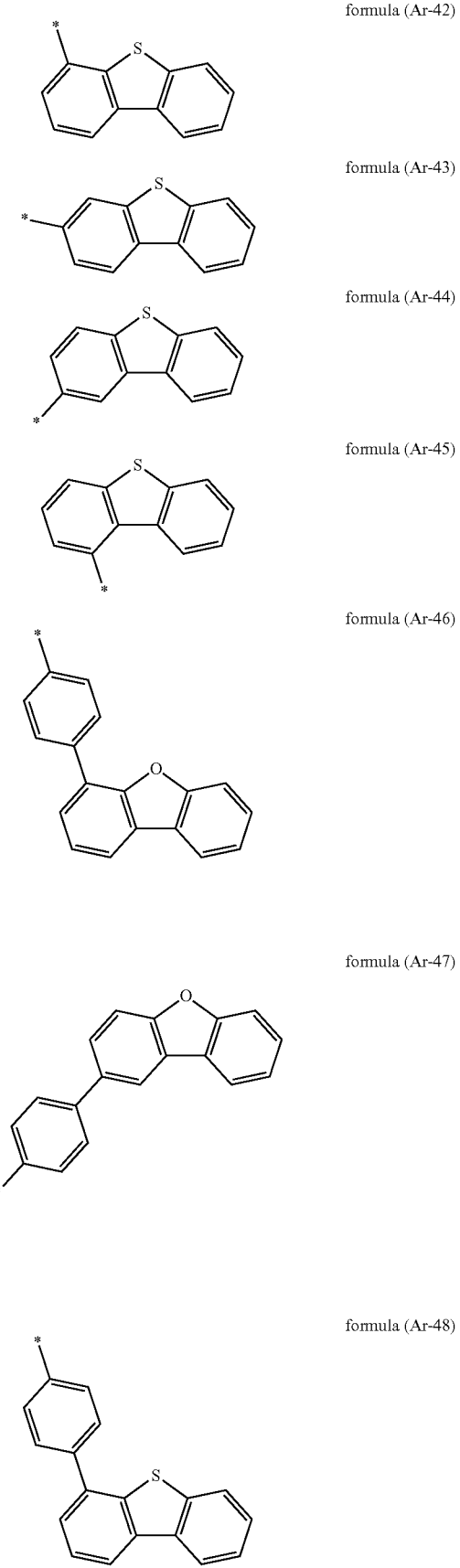

formula (Ar-49)
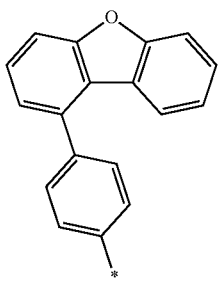
formula (Ar-50)
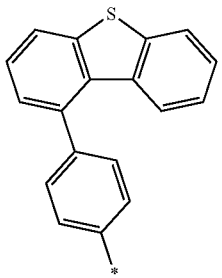
formula (Ar-51)
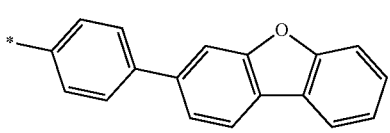
formula (Ar-52)
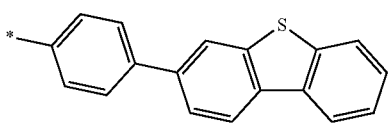
formula (Ar-53)
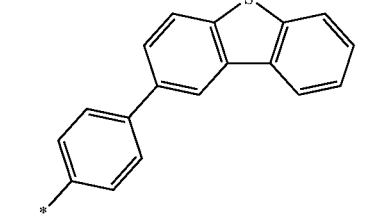
formula (Ar-54)
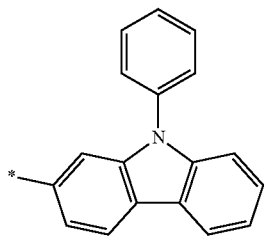
formula (Ar-55)
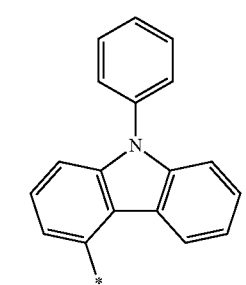
formula (Ar-56)
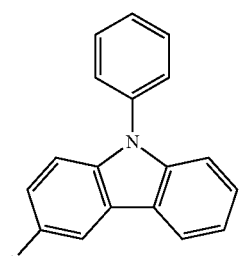
formula (Ar-57)
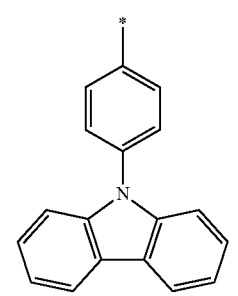
formula (Ar-58)
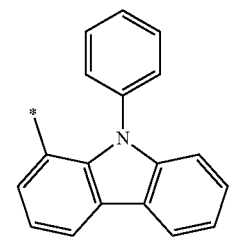
formula (Ar-59)
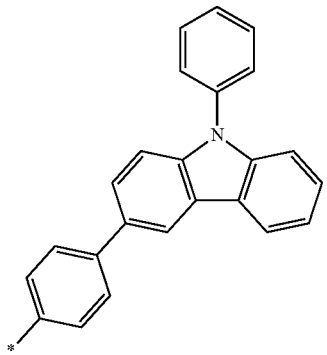
formula (Ar-60)
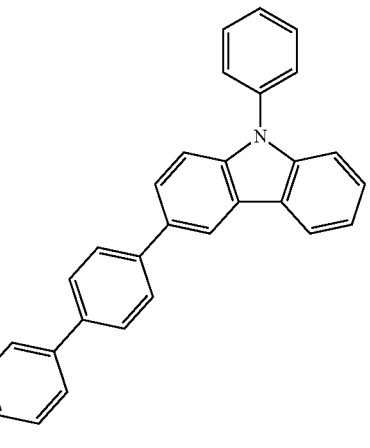

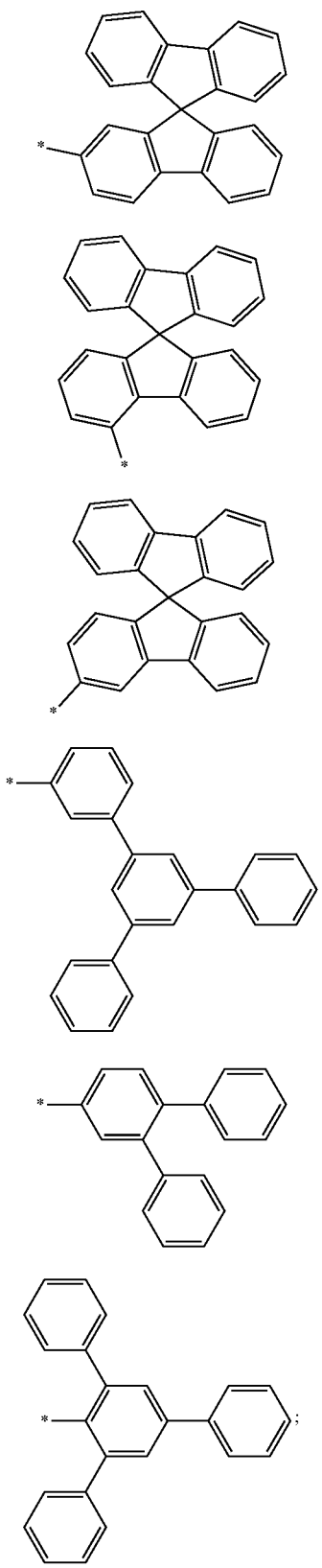

formula (Ar-61)

formula (Ar-62)

formula (Ar-63)

formula (Ar-64)

formula (Ar-65)

formula (Ar-66)

$Ar^3$, $Ar^4$, $Ar^5$, $Ar^6$ on each occurrence, identically or differently, conform to formula (Ar-1), formula (Ar-1)

which is optionally substituted by one or more radicals $R^2$ on the free positions, and where the bond denoted by * represents the bonding position of the respective group;

$R^1$, $R^2$ are selected on each occurrence, identically or differently, from H, D, F, C(=O)$R^3$, $CF_3$, $OCF_3$, CN, Si($R^3$)$_3$, N($R^3$)$_2$, P(=O)($R^3$)$_2$, $OR^3$, S(=O)$R^3$, S(=O)$_2$ $R^3$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms and heteroaromatic ring systems having 5 to 40 aromatic ring atoms; where two or more radicals $R^1$ or $R^2$ is optionally linked to one another and may form a ring; where the said alkyl, alkoxy, alkenyl and alkynyl groups and the said aromatic ring systems and heteroaromatic ring systems may each be substituted by one or more radicals $R^3$; and where one or more $CH_2$ groups in the said alkyl, alkoxy, alkenyl and alkynyl groups is optionally replaced by —$R^3$C=$CR^3$—, —C≡C—, Si($R^3$)$_2$, C=O, C=$NR^3$, —C(=O)O—, —C(=O)$NR^3$—, $NR^3$, P(=O)($R^3$), —O—, —S—, SO or $SO_2$;

$R^3$ is selected on each occurrence, identically or differently, from H, D, F, C(=O)$R^4$, $CF_3$, $OCF_3$, CN, Si($R^4$)$_3$, N($R^4$)$_2$, P(=O)($R^4$)$_2$, $OR^4$, S(=O)$R^4$, S(=O)$_2$ $R^4$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms and heteroaromatic ring systems having 5 to 40 aromatic ring atoms; where two or more radicals $R^3$ is optionally linked to one another and may form a ring; where the said alkyl, alkoxy, alkenyl and alkynyl groups and the said aromatic ring systems and heteroaromatic ring systems may each be substituted by one or more radicals $R^4$; and where one or more $CH_2$ groups in the said alkyl, alkoxy, alkenyl and alkynyl groups is optionally replaced by —$R^4$C=$CR^4$—, —C≡C—, Si($R^4$)$_2$, C=O, C=$NR^4$, —C(=O)O—, —C(=O)$NR^4$—, $NR^4$, P(=O)($R^4$), —O—, —S—, SO or $SO_2$;

$R^4$ is selected on each occurrence, identically or differently, from H, D, F, CN, alkyl groups having 1 to 20 C atoms, aromatic ring systems having 6 to 40 aromatic ring atoms and heteroaromatic ring systems having 5 to 40 aromatic ring atoms; where two or more radicals $R^4$ is optionally linked to one another and may form a ring; and where the said alkyl groups, aromatic ring systems and heteroaromatic ring systems is optionally substituted by F or CN;

a, b, c, d are on each occurrence, identically or differently, 0 or 1; and wherein at least one of the indices a, b, c and d is equal to 1.

2. An oligomer, polymer or dendrimer containing one or more compounds of the formula (I)

formula (I)

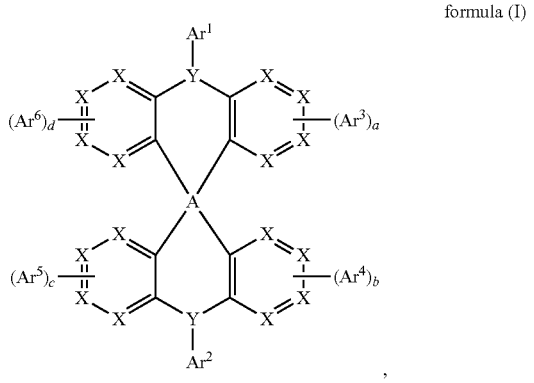

where the following applies to the symbols and indices occurring:
A is C or Si;
Y is on each occurrence, identically or differently, N or P;
X is on each occurrence, identically or differently, CR¹ or N;
Ar¹, Ar² are on each occurrence, identically or differently, an aromatic ring system having 6 to 40 aromatic ring atoms, which is optionally substituted by one or more radicals R², or a heteroaromatic ring system having 5 to 40 aromatic ring atoms, which is optionally substituted by one or more radicals R²;
Ar³, Ar⁴, Ar⁵, Ar⁶ are on each occurrence, identically or differently, an aromatic ring system having 6 to 40 aromatic ring atoms, which is optionally substituted by one or more radicals R², or a heteroaromatic ring system having 5 to 40 aromatic ring atoms, which is optionally substituted by one or more radicals R²;
R¹, R² are selected on each occurrence, identically or differently, from H, D, F, C(=O)R³, CF₃, OCF₃, CN, Si(R³)₃, N(R³)₂, P(=O)(R³)₂, OR³, S(=O)R³, S(=O)₂R³, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms and heteroaromatic ring systems having 5 to 40 aromatic ring atoms; where two or more radicals R¹ or R² is optionally linked to one another and may form a ring; where the said alkyl, alkoxy, alkenyl and alkynyl groups and the said aromatic ring systems and heteroaromatic ring systems may each be substituted by one or more radicals R³; and where one or more CH₂ groups in the said alkyl, alkoxy, alkenyl and alkynyl groups is optionally replaced by —R³C=CR³—, —C≡C—, Si(R³)₂, C=O, C=NR³, —C(=O)O—, —C(=O)NR³—, NR³, P(=O)(R³), —O—, —S—, SO or SO₂;
R³ is selected on each occurrence, identically or differently, from H, D, F, C(=O)R⁴, CF₃, OCF₃, CN, Si(R⁴)₃, N(R⁴)₂, P(=O)(R⁴)₂, OR⁴, S(=O)R⁴, S(=O)₂R⁴, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms and heteroaromatic ring systems having 5 to 40 aromatic ring atoms; where two or more radicals R³ is optionally linked to one another and may form a ring; where the said alkyl, alkoxy, alkenyl and alkynyl groups and the said aromatic ring systems and heteroaromatic ring systems may each be substituted by one or more radicals R⁴; and where one or more Cl₂ groups in the said alkyl, alkoxy, alkenyl and alkynyl groups is optionally replaced by —R⁴C=CR⁴—, —C≡C—, Si(R⁴)₂, C=O, C=NR⁴, —C(=O)O—, —C(=O)NR⁴—, NR⁴, P(=O)(R⁴), —O—, —S—, SO or SO₂,
R⁴ is selected on each occurrence, identically or differently, from H, D, F, CN, alkyl groups having 1 to 20 C atoms, aromatic ring systems having 6 to 40 aromatic ring atoms and heteroaromatic ring systems having 5 to 40 aromatic ring atoms; where two or more radicals R⁴ is optionally linked to one another and may form a ring; and where the said alkyl groups, aromatic ring systems and heteroaromatic ring systems is optionally substituted by F or CN;
a, b, c, d are on each occurrence, identically or differently, 0 or 1;
where at least one of the two groups Ar¹ and Ar² is an aromatic ring system having 12 to 40 aromatic ring atoms, which is optionally substituted by one or more radicals R², or a heteroaromatic ring system having 12 to 40 aromatic ring atoms, which is optionally substituted by one or more radicals R²; and
wherein at least one of the indices a, b, c and d is equal to 1,
where the bond(s) to the polymer, oligomer or dendrimer is optionally localised at any position in formula (I) that are substituted by R¹ or R².

3. A compound of the formula (I)

formula (I)

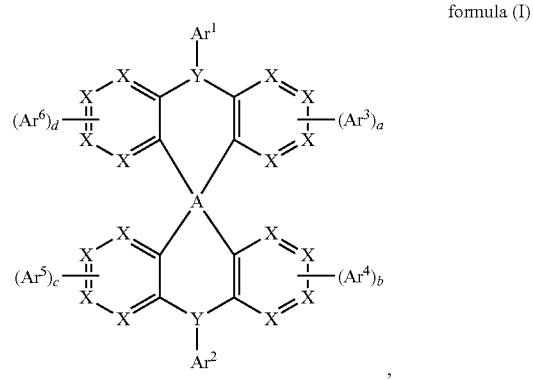

where the following applies to the symbols and indices occurring:
A is C;
Y is N;
X is on each occurrence, identically or differently, CR¹ or N;
Ar¹, Ar² are on each occurrence, identically or differently, selected from the formula (Ar-2) to (Ar-15) and (Ar-18) to (Ar-66)

formula (Ar-2)

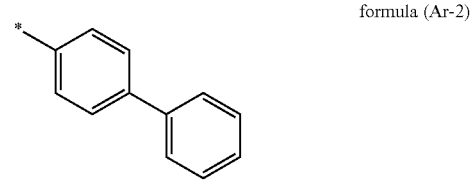

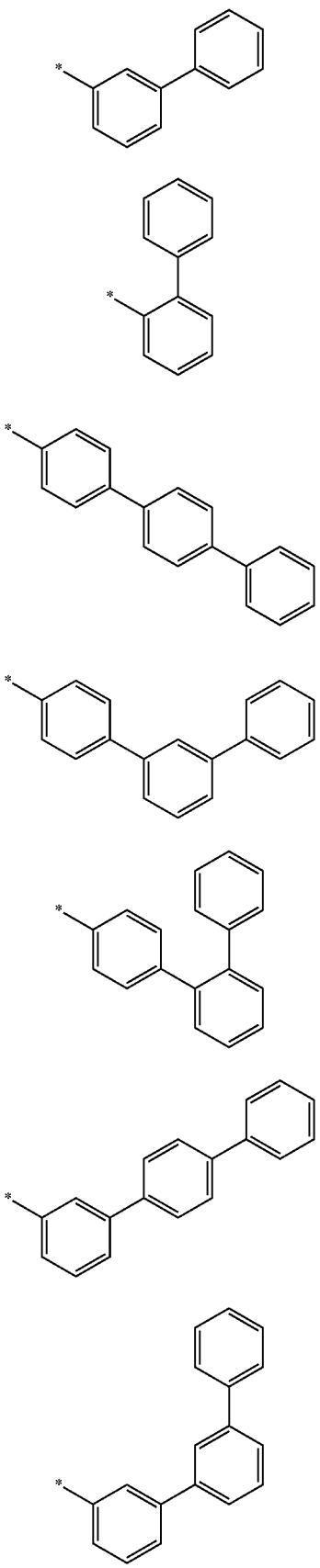
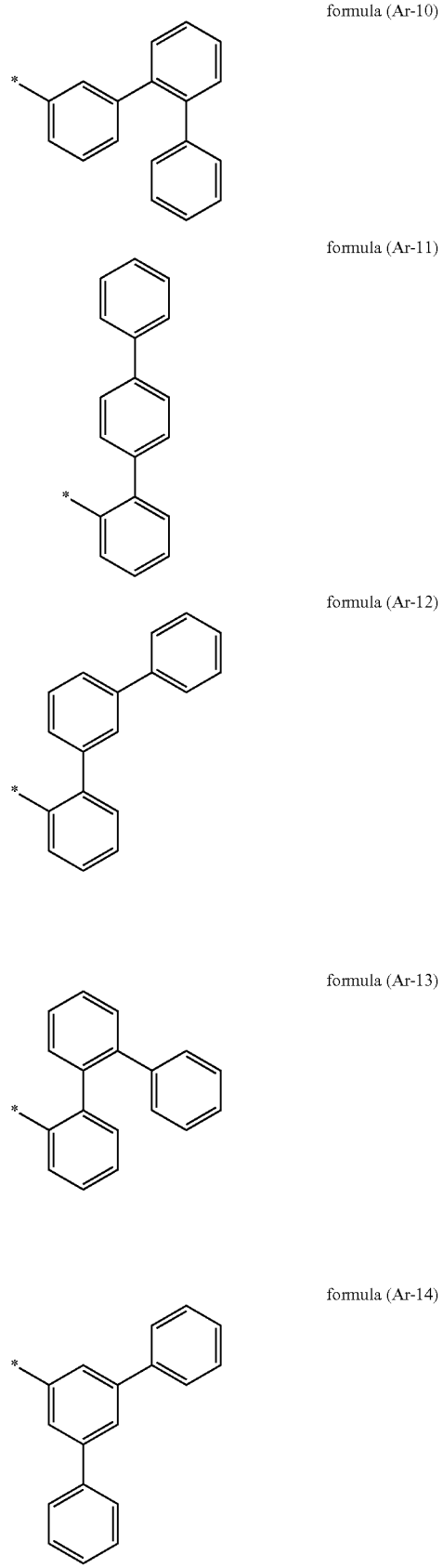

formula (Ar-15)
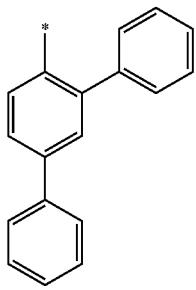
formula (Ar-18)
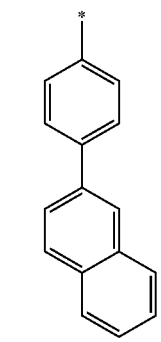
formula (Ar-19)
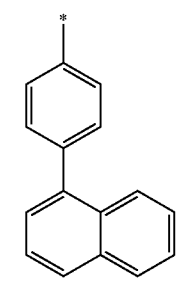
formula (Ar-20)
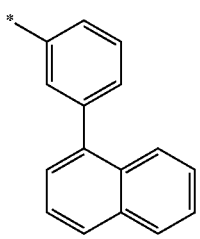
formula (Ar-21)
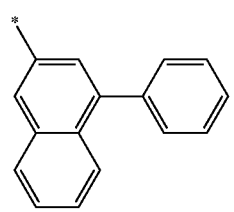
formula (Ar-22)
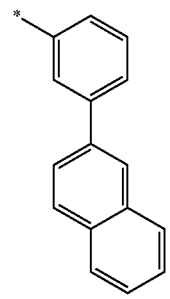
formula (Ar-23)
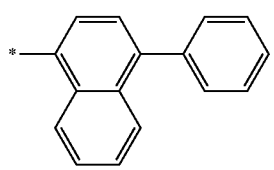
formula (Ar-24)
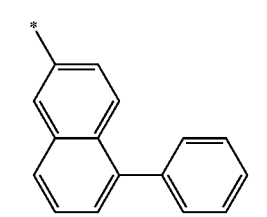
formula (Ar-25)
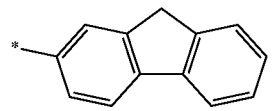
formula (Ar-26)
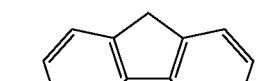
formula (Ar-27)
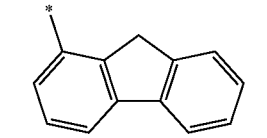
formula (Ar-28)
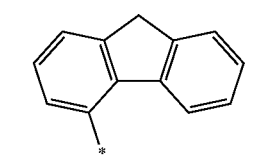
formula (Ar-29)
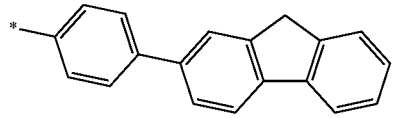
formula (Ar-30)
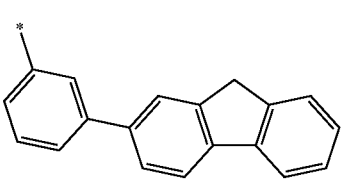

formula (Ar-31)
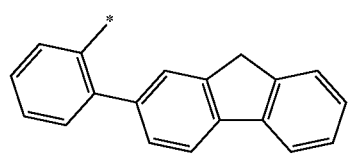
formula (Ar-32)
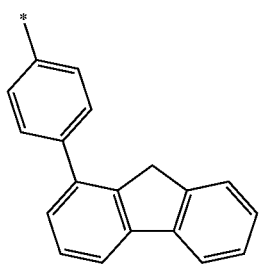
formula (Ar-33)
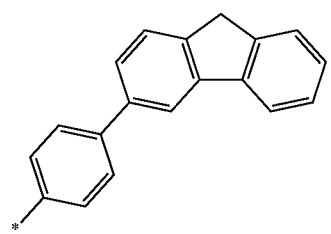
formula (Ar-34)
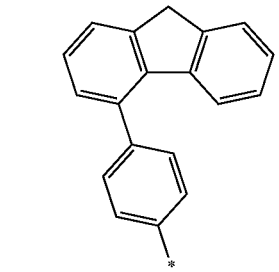
formula (Ar-35)
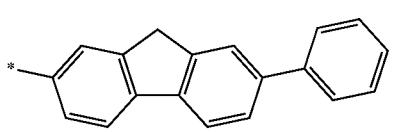
formula (Ar-36)
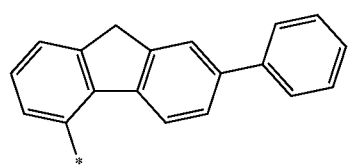
formula (Ar-37)
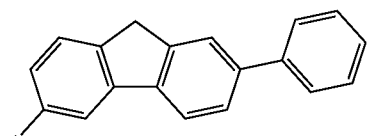
formula (Ar-25-1)
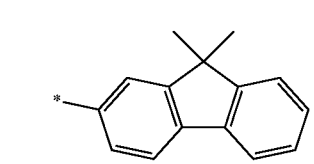
formula (Ar-26-1)
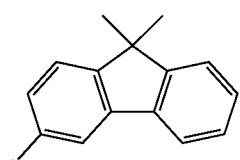
formula (Ar-27-1)
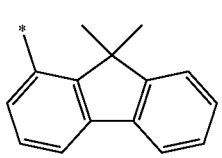
formula (Ar-28-1)
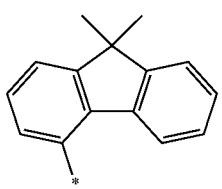
formula (Ar-29-1)
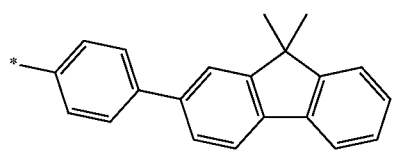
formula (Ar-30-1)
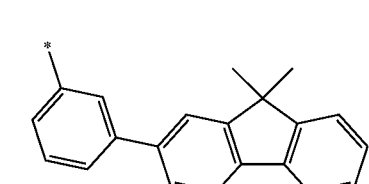
formula (Ar-31-1)
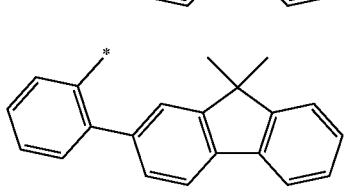
formula (Ar-32-1)
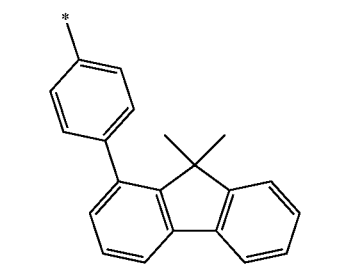
formula (Ar-33-1)
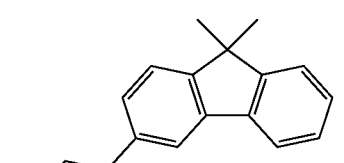

formula (Ar-34-1)
formula (Ar-35-1)
formula (Ar-36-1)
formula (Ar-37-1)
formula (Ar-25-2)
formula (Ar-26-2)
formula (Ar-27-2)
formula (Ar-28-2)
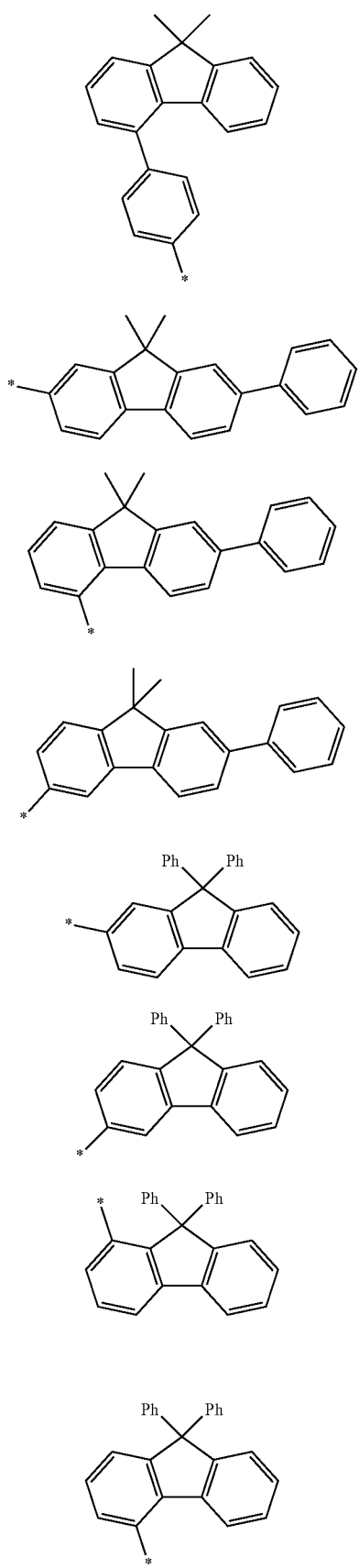
formula (Ar-29-2)
formula (Ar-30-2)
formula (Ar-31-2)
formula (Ar-32-2)
formula (Ar-33-2)
formula (Ar-34-2)
formula (Ar-35-2)
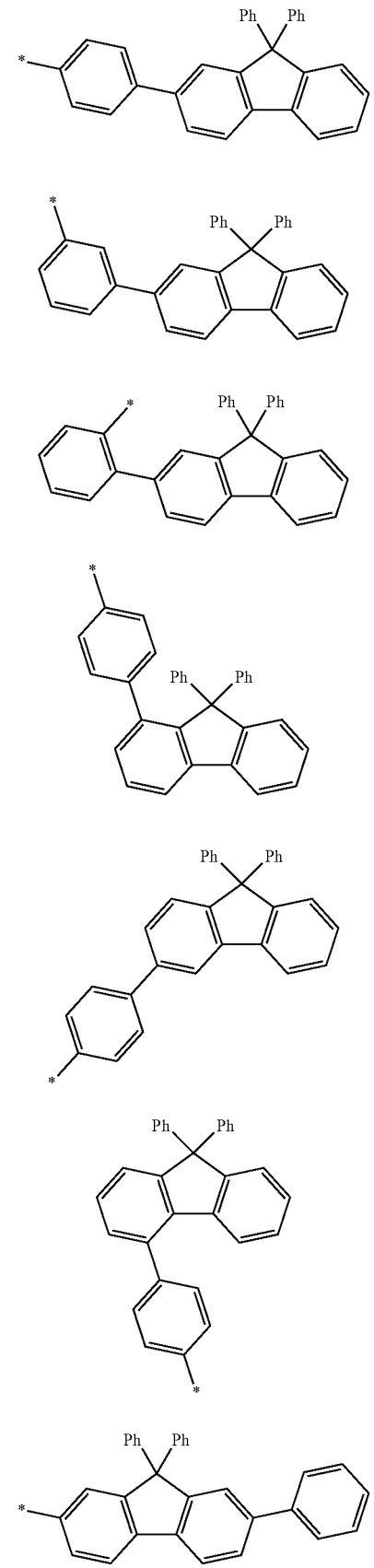

formula (Ar-36-2)
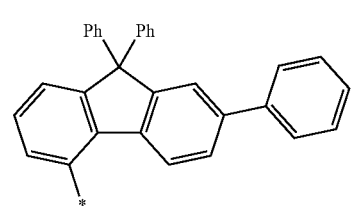
formula (Ar-37-2)
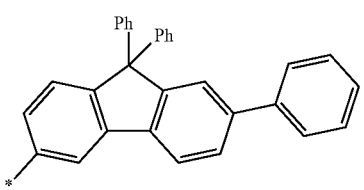
formula (Ar-25-3)
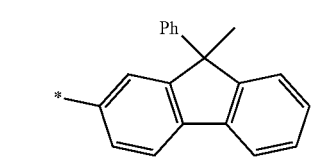
formula (Ar-26-3)
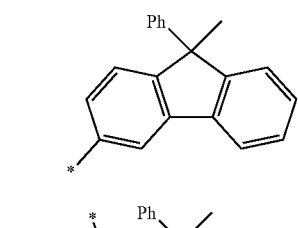
formula (Ar-27-3)
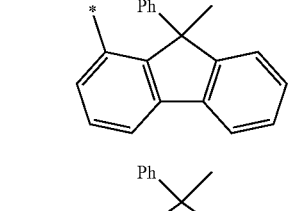
formula (Ar-28-3)
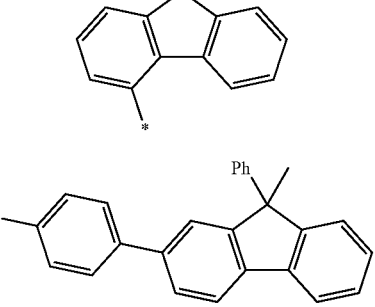
formula (Ar-29-3)
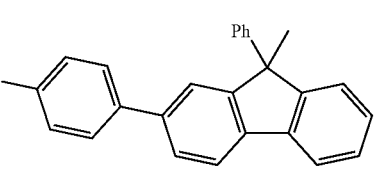
formula (Ar-30-3)
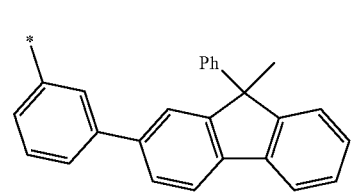
formula (Ar-31-3)
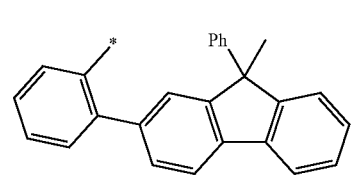
formula (Ar-32-3)
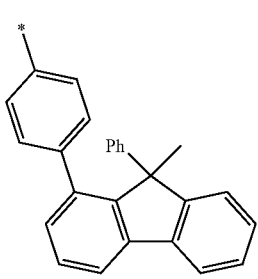
formula (Ar-33-3)
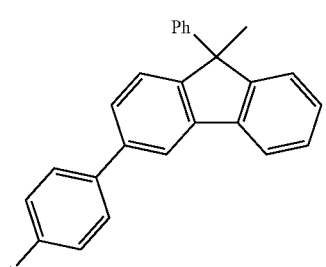
formula (Ar-34-3)
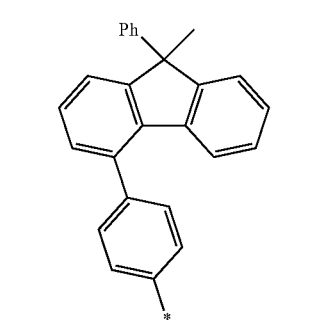
formula (Ar-35-3)
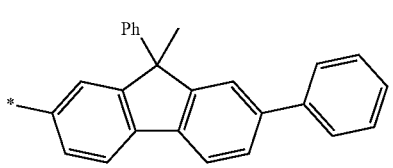
formula (Ar-36-3)
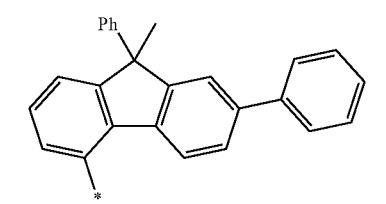
formula (Ar-37-3)
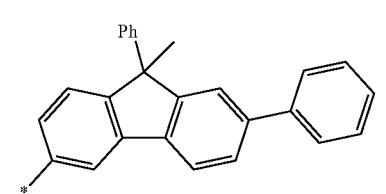
formula (Ar-25-4)
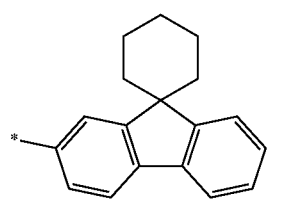

-continued
formula (Ar-26-4)
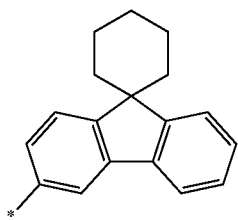
formula (Ar-27-4)
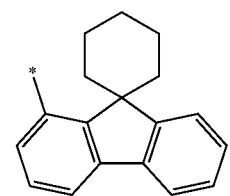
formula (Ar-28-4)
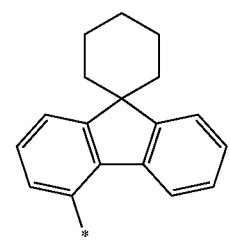
formula (Ar-29-4)
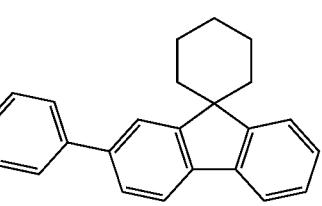
formula (Ar-30-4)
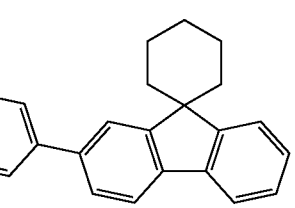
formula (Ar-31-4)
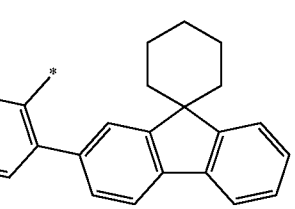
formula (Ar-32-4)
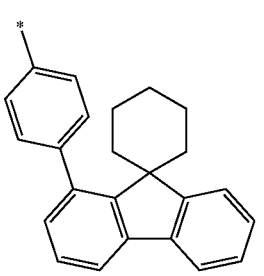
formula (Ar-33-4)
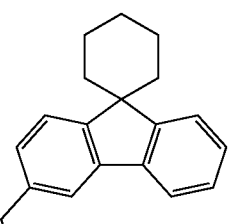
formula (Ar-34-4)
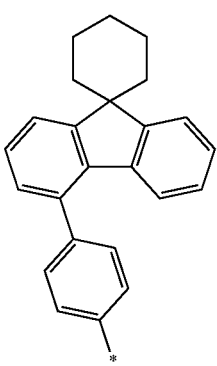
formula (Ar-35-4)
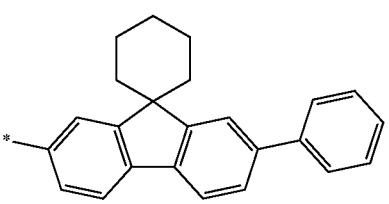
formula (Ar-36-4)
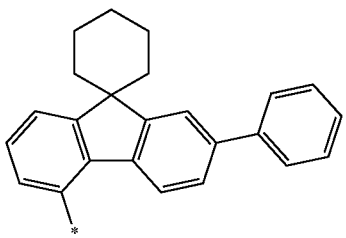
formula (Ar-37-4)
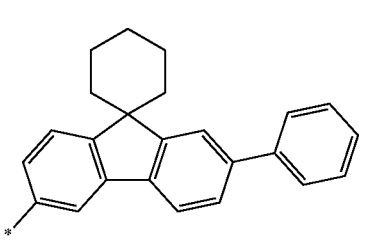
formula (Ar-25-5)
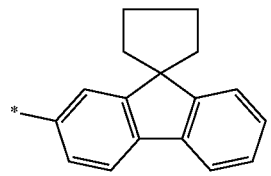

formula (Ar-26-5)
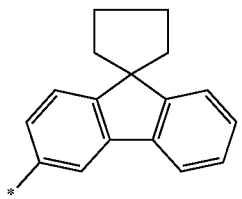
formula (Ar-27-5)
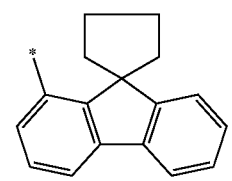
formula (Ar-28-5)
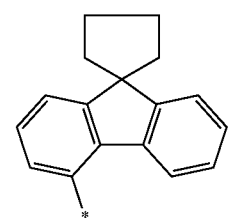
formula (Ar-29-5)
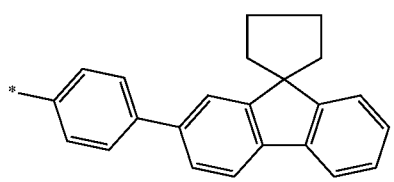
formula (Ar-30-5)
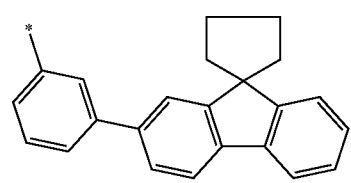
formula (Ar-31-5)
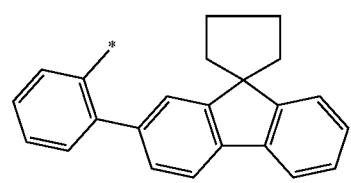
formula (Ar-32-5)
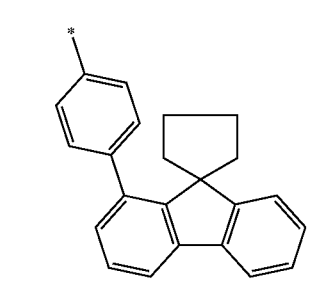
formula (Ar-33-5)
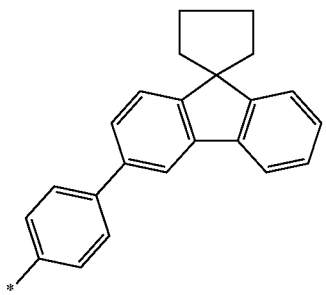
formula (Ar-34-5)
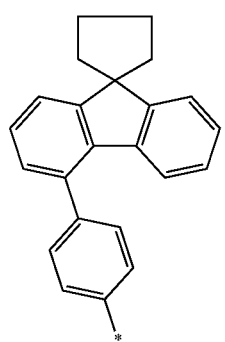
formula (Ar-35-5)
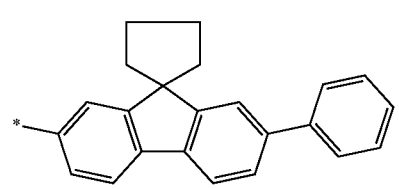
formula (Ar-36-5)
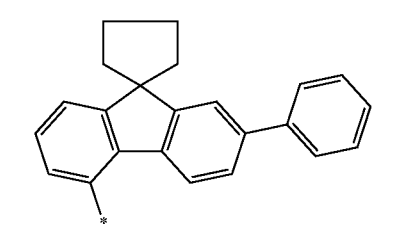
formula (Ar-37-5)
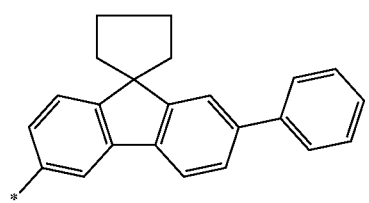
formula (Ar-38)
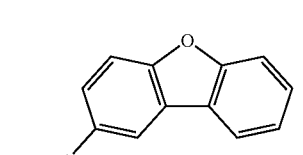
formula (Ar-39)
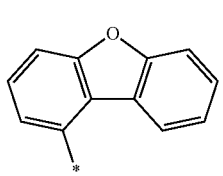

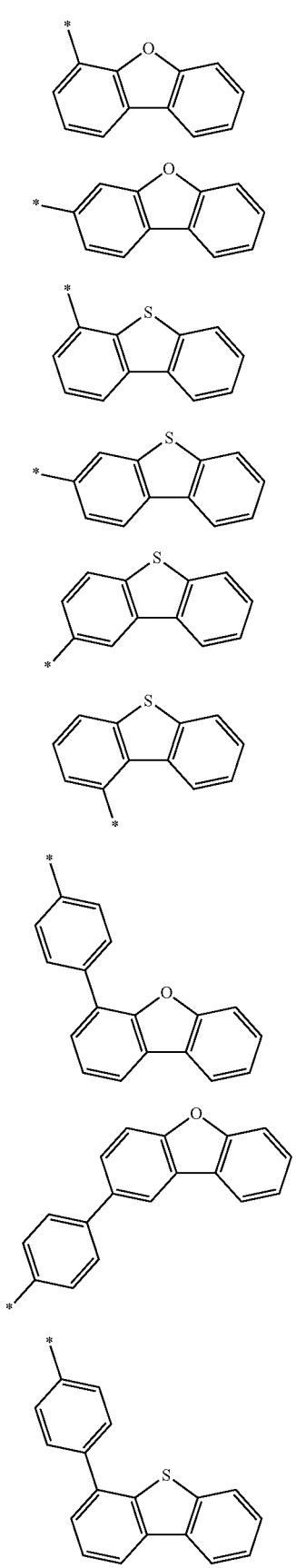
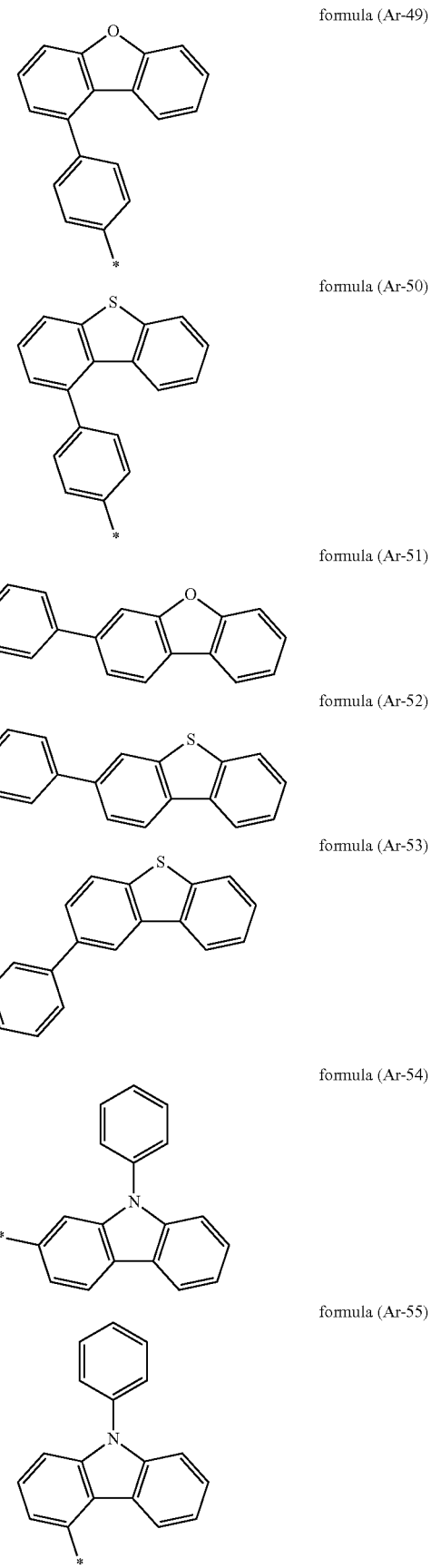

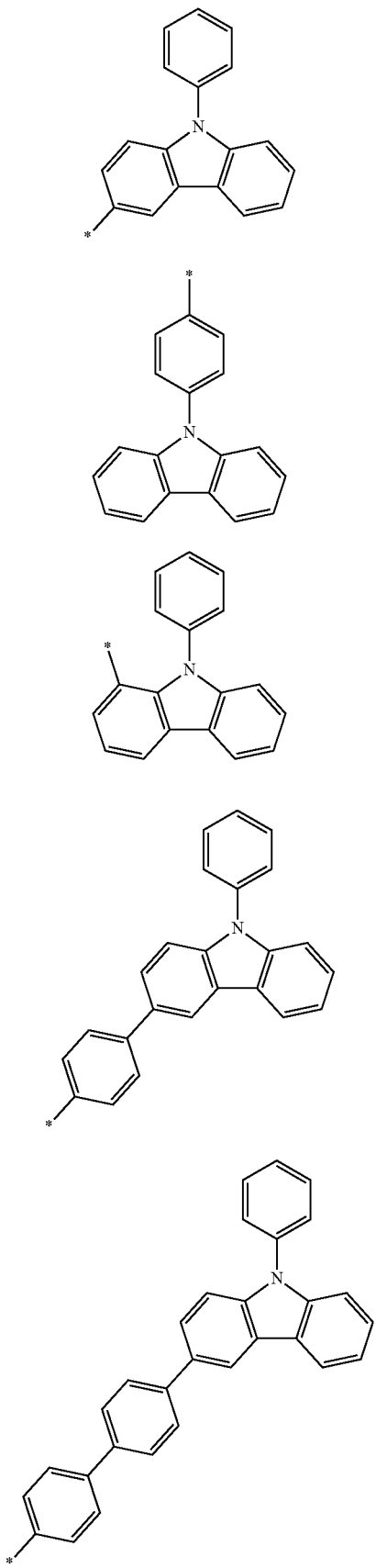
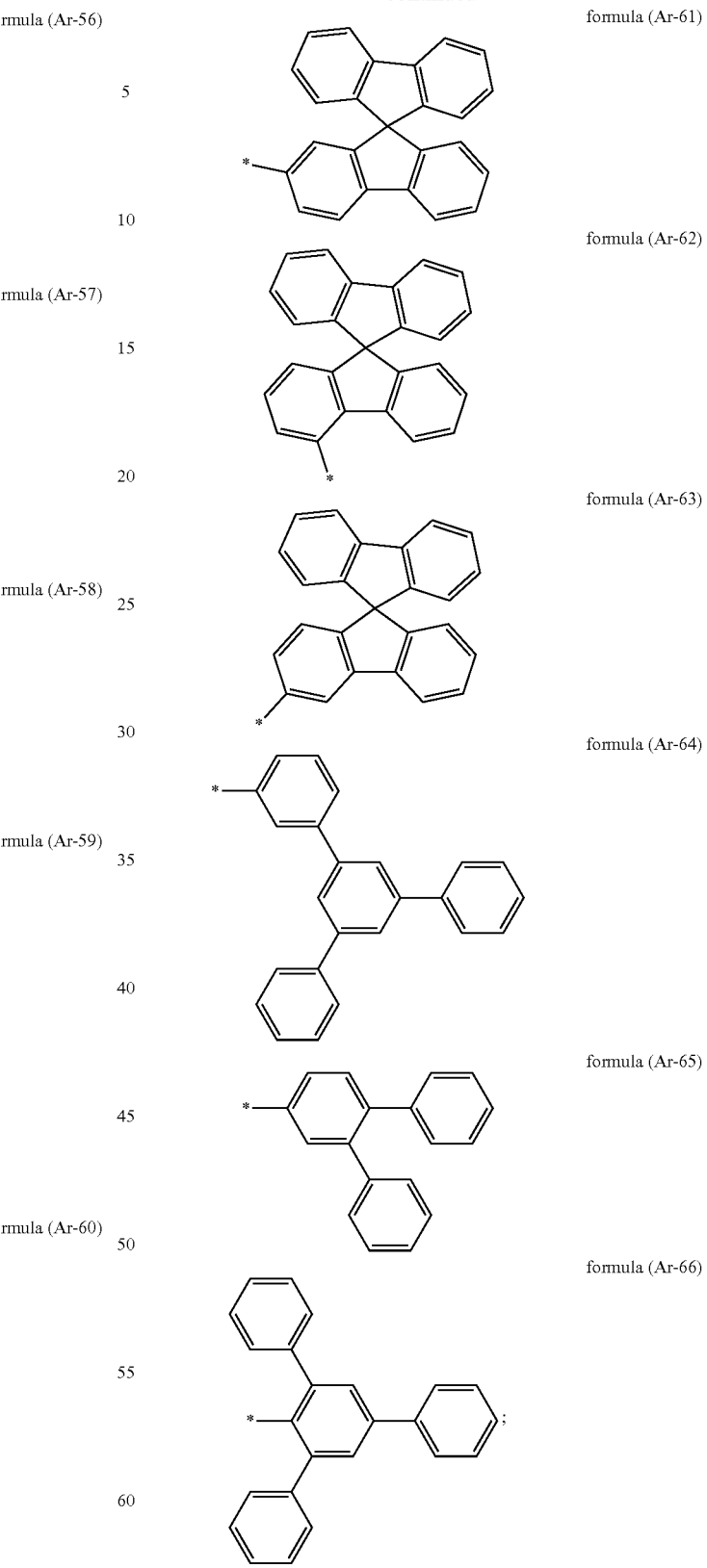
Ar³, Ar⁴, Ar⁵, Ar⁶ are on each occurrence, identically or differently, an aromatic ring system having 6 to 40 aromatic ring atoms, which is optionally substituted by one or more radicals $R^2$, or a heteroaromatic ring system having 5 to 40 aromatic ring atoms, which is optionally substituted by one or more radicals $R^2$;

$R^1$, $R^2$ are selected on each occurrence, identically or differently, from H, D, F, C(=O)$R^3$, $CF_3$, $OCF_3$, CN, Si($R^3$)$_3$, N($R^3$)$_2$, P(=O)($R^3$)$_2$, O$R^3$, S(=O)$R^3$, S(=O)$_2$ $R^3$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms and heteroaromatic ring systems having 5 to 40 aromatic ring atoms; where two or more radicals $R^1$ or $R^2$ is optionally linked to one another and may form a ring; where the said alkyl, alkoxy, alkenyl and alkynyl groups and the said aromatic ring systems and heteroaromatic ring systems may each be substituted by one or more radicals $R^3$; and where one or more $CH_2$ groups in the said alkyl, alkoxy, alkenyl and alkynyl groups is optionally replaced by —$R^3$C=C$R^3$—, —C≡C—, Si($R^3$)$_2$, C=O, C=N$R^3$, —C(=O)O—, —C(=O)N$R^3$—, N$R^3$, P(=O)($R^3$), —O—, —S—, SO or $SO_2$;

$R^3$ is selected on each occurrence, identically or differently, from H, D, F, C(=O)$R^4$, $CF_3$, $OCF_3$, CN, Si($R^4$)$_3$, N($R^4$)$_2$, P(=O)($R^4$)$_2$, O$R^4$, S(=O)$R^4$, S(=O)$_2$ $R^4$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms and heteroaromatic ring systems having 5 to 40 aromatic ring atoms; where two or more radicals $R^3$ is optionally linked to one another and may form a ring; where the said alkyl, alkoxy, alkenyl and alkynyl groups and the said aromatic ring systems and heteararomatic ring systems may each be substituted by one or more radicals $R^4$; and where one or more $CH_2$ groups in the said alkyl, alkoxy, alkenyl and alkynyl groups is optionally replaced by —$R^4$C=C$R^4$—, —C≡C—, Si($R^4$)$_2$, C=O, C=N$R^4$, —C(=O)O—, —C(=O)N$R^4$—, N$R^4$, P(=O)($R^4$), —O—, —S—, SO or $SO_2$;

$R^4$ is selected on each occurrence, identically or differently, from H, D, F, CN, alkyl groups having 1 to 20 C atoms, aromatic ring systems having 6 to 40 aromatic ring atoms and heteroaromatic ring systems having 5 to 40 aromatic ring atoms; where two or more radicals $R^4$ is optionally linked to one another and may form a ring; and where the said alkyl groups, aromatic ring systems and heteroaromatic ring systems is optionally substituted by F or CN;

a, b, c, d are on each occurrence, identically or differently, 0 or 1; and wherein at least one of the indices a, b, c and d is equal to 1.

4. The compound according to claim 3, wherein the compound contains no arylamino group as substituent.

5. The compound according to claim 3, wherein precisely 1, 2 or 3 indices selected from the indices a, b, c and d in formula (I) are equal to 1.

6. The compound according to claim 3, wherein X is equal to $CR^1$.

7. The compound according to claim 3, wherein the groups $Ar^3$, $Ar^4$, $Ar^5$, $Ar^6$ occurring in the compound of the formula (I) are selected identically.

8. The compound according to claim 3, wherein $R^1$ is selected on each occurrence, identically or differently, from H, D, F, CN, Si($R^3$)$_3$, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^3$; and where one or more $CH_2$ groups in the said alkyl or alkoxy groups may be replaced by —C≡C—, —$R^3$C=C$R^3$—, Si($R^3$)$_2$, C=O, C=NR, —N$R^3$—, —O—, —S—, —C(=O)O— or —C(=O)N$R^3$—;

$R^2$ is selected on each occurrence, identically or differently, from H, D, F, CN, Si($R^3$)$_3$, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^3$; and where one or more $CH_2$ groups in the said alkyl or alkoxy groups may be replaced by —C≡C—, —$R^3$C=C$R^{3-}$, Si($R^3$)$_2$, C=O, C=N$R^3$, —N$R^3$—, —O—, —S—, —C(=O)O— or —C(=O)N$R^3$—;

$R^3$ is selected on each occurrence, identically or differently, from H, D, F, CN, Si($R^4$)$_3$, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^4$; and where one or more $CH_2$ groups in the said alkyl or alkoxy groups may be replaced by —C≡C—, —$R^4$C=C$R^4$—, Si($R^4$)$_2$, C=O, C=N$R^4$, —N$R^4$—, —O—, —S—, —C(=O)O— or —C(=O)N$R^4$— and $R^4$ is selected on each occurrence, identically or differently, from H, D, F, CN, alkyl groups having 1 to 20 C atoms, aromatic ring systems having 6 to 40 aromatic ring atoms and heteroaromatic ring systems having 5 to 40 aromatic ring atoms; and where the said alkyl groups, aromatic ring systems and heteroaromatic ring systems is optionally substituted by F or CN.

9. The compound according to claim 3, wherein at least one of the groups $Ar^1$, $Ar^2$, $Ar^3$, $Ar^4$, $Ar^5$ and $Ar^6$ contains at least one heteroaryl group having 5 to 20 aromatic ring atoms.

10. The compound according to claim 3, wherein the compound of the formula (I) conforms to one of the formulae (I-1) to (I-3)

formula (I-1)

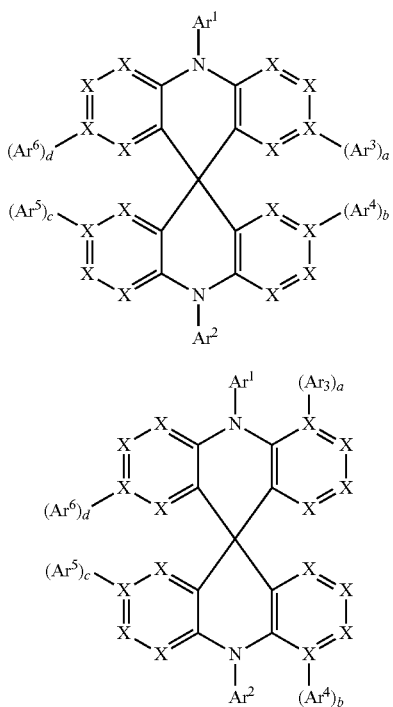

formula (Ar-1)

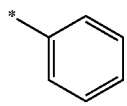

formula (Ar-16)

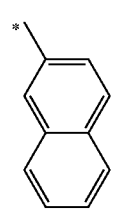

formula (Ar-17)

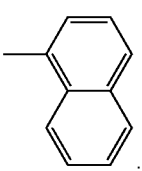

formula (I-2)

13. The compound according to claim 3, wherein Ar¹ and Ar² are of the formula (Ar-2).

14. The compound according to claim 13, wherein Ar³ to Ar⁶ conform to formula (Ar-1), formula (Ar-1)

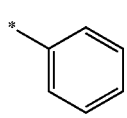

formula (I-3)

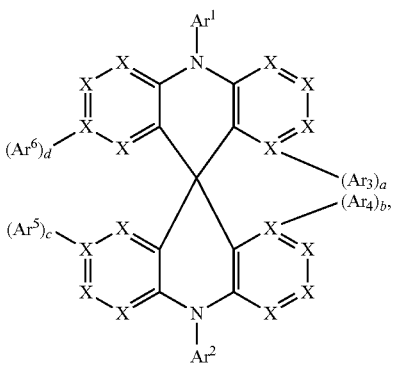

which is substituted by radicals R² at one or more of the free positions, and where the bond denoted by * represents the bonding position of the respective group.

15. The compound according to claim 13 wherein Ar³ to Ar⁶ are identically or differently on each occurrence selected from formulae (Ar-1) to Ar-66) wherein (Ar-1), (Ar-16) (Ar-17) are as follows:

formula (Ar-1)

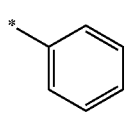

formula (Ar-16)

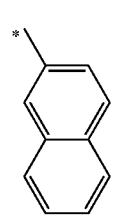

where the symbols and indices occurring are defined in accordance with claim 3.

11. A process for the preparation of the compound according to claim 3, wherein the process comprises the following steps:

1) reacting a halogen-substituted diphenylamine derivative with an acridinone derivative in the presence of an organometallic compound to form an intermediate;

2) ring-closure reacting the intermediate formed in 1) to give a spirobisacridine derivative;

3) introducing an aryl or heteroaryl group on a free nitrogen atom of the spirobisacridine derivative by means of Buchwald coupling.

12. The compound according to claim 3, wherein Ar³ to Ar⁶ are identically or differently on each occurrence selected from formulae (Ar-1) to Ar-66) wherein (Ar-1), (Ar-16) and (Ar-17) are as follows:

formula (Ar-17)

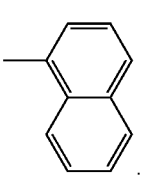

16. The compound according to claim 15, wherein R¹ is selected on each occurrence, identically or differently, from H, D, F, CN, Si(R³)₃, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^3$; and where one or more $CH_2$ groups in the said alkyl or alkoxy groups may be replaced by —C≡C—, —$R^3$C=C$R^3$—, Si($R^3$)$_2$, C=O, C=N$R^3$, —N$R^3$—, —O—, —S—, —C(=O) O— or —C(=O)N$R^3$—;

$R^2$ is selected on each occurrence, identically or differently, from H, D, F, CN, Si($R^3$)$_3$, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^3$; and where one or more $CH_2$ groups in the said alkyl or alkoxy groups may be replaced by —C≡C—, —$R^3$C=C$R^3$—, Si($R^3$)$_2$, C=O, C=N$R^3$, —N$R^3$—, —O—, —S—, —C(=O)O— or —C(=O)N$R^3$—;

$R^3$ is selected on each occurrence, identically or differently, from H, D, F, C, CN, Si($R^4$)$_3$, straight-chain alkyl or alkoxy groups having 1 to 10 C atoms, branched or cyclic alkyl or alkoxy groups having 3 to 10 C atoms, aromatic ring systems having 6 to 24 aromatic ring atoms and heteroaromatic ring systems having 5 to 24 aromatic ring atoms; where the said alkyl and alkoxy groups, the said aromatic ring systems and the said heteroaromatic ring systems may each be substituted by one or more radicals $R^4$; and where one or more $CH_2$ groups in the said alkyl or alkoxy groups may be replaced by —C≡C—, —$R^4$C=C$R^4$—, Si($R^4$)$_2$, C=O, C=N$R^4$, —N$R^4$—, —O—, —S—, —C(=O) O— or —C(=O)N$R^4$— and $R^4$ is selected on each occurrence, identically or differently, from H, D, F, CN, alkyl groups having 1 to 20 C atoms, aromatic ring systems having 6 to 40 aromatic ring atoms and heteroaromatic ring systems having 5 to 40 aromatic ring atoms; and where the said alkyl groups, aromatic ring systems and heteroaromatic ring systems is optionally substituted by F or CN.

17. A formulation comprising at least one compound according to claim 3 and at least one solvent.

18. An electronic device comprising at least one compound according to claim 3.

19. The electronic device according to claim 18, wherein the device is selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

20. An electronic device comprising at least one oligomer, polymer or dendrimer according to claim 2.

21. An organic electroluminescent device comprising at least one compound according to claim 3 is present in a layer selected from hole-transport layers and emitting layers.

22. The organic electroluminescent device according to claim 21, wherein the at least one compound is present in an emitting layer together with one or more phosphorescent emitters.

23. The organic electroluminescent device according to claim 21, wherein the at least one compound is present in a hole-transport layer together with one or more p-dopants.

* * * * *